US012691112B2

(12) United States Patent
Avadhani et al.

(10) Patent No.: US 12,691,112 B2
(45) Date of Patent: Jul. 28, 2026

(54) FGFR TYROSINE KINASE INHIBITORS FOR THE TREATMENT OF UROTHELIAL CARCINOMA

(71) Applicant: Janssen Pharmaceutica NV, Beerse (BE)

(72) Inventors: Anjali Narayan Avadhani, Springhouse, PA (US); Anne Elizabeth O'Hagan, Springhouse, PA (US); Ademi Elena Santiago-Walker, Springhouse, PA (US)

(73) Assignee: Janssen Pharmaceutica NV, Beerse (BE)

( * ) Notice: Subject to any disclaimer, the term of this patent is extended or adjusted under 35 U.S.C. 154(b) by 1196 days.

(21) Appl. No.: 17/599,729

(22) PCT Filed: Mar. 27, 2020

(86) PCT No.: PCT/US2020/025166
§ 371 (c)(1),
(2) Date: Sep. 29, 2021

(87) PCT Pub. No.: WO2020/205493
PCT Pub. Date: Oct. 8, 2020

(65) Prior Publication Data

US 2022/0054484 A1 Feb. 24, 2022

(30) Foreign Application Priority Data

Mar. 29, 2019 (EP) .................................... 19166428
Jul. 30, 2019 (EP) .................................... 19188971

(51) Int. Cl.
*A61K 31/498* (2006.01)
*A61P 35/00* (2006.01)
*C12Q 1/6886* (2018.01)

(52) U.S. Cl.
CPC ............ *A61K 31/498* (2013.01); *A61P 35/00* (2018.01); *C12Q 1/6886* (2013.01); *C12Q 2600/156* (2013.01)

(58) Field of Classification Search
CPC ................ A61K 31/498; C12Q 1/6886; C12Q 2600/156
See application file for complete search history.

(56) References Cited

U.S. PATENT DOCUMENTS 4,666,828 A 5/1987 Gusella
4,683,202 A 7/1987 Mullis
(Continued)

FOREIGN PATENT DOCUMENTS

WO 2006/000420 A1 1/2006
WO 2006/127926 A2 11/2006
(Continued)

OTHER PUBLICATIONS

Moss, T.J. et al. European Urology 72(4):641-649 (Oct. 2017). (Year: 2017).*
(Continued)

*Primary Examiner* — Diana B Johannsen
(74) *Attorney, Agent, or Firm* — BakerHostetler

(57) ABSTRACT

Described here are methods of treating urothelial carcinoma in a patient comprising evaluating a biological sample from the patient for the presence of at least two fibroblast growth factor receptor (FGFR) genetic alterations and treating the patient with an FGFR inhibitor. Also described herein are methods of treating urothelial carcinoma in a patient harboring at least two fibroblast growth factor receptor (FGFR) genetic alterations comprising administering a FGFR inhibitor.

28 Claims, 8 Drawing Sheets

Specification includes a Sequence Listing.

[a]Patients in the selected regimen were further uptitrated to 9 mg/d if they had not reached 5.5 mg/dL serum phosphate level by Day 14 and if they had no TRAEs.

(56) References Cited

U.S. PATENT DOCUMENTS

| | | | |
|---|---|---|---|
| 4,801,531 | A | 1/1989 | Frossard |
| 5,033,252 | A | 7/1991 | Carter |
| 5,052,558 | A | 10/1991 | Carter |
| 5,192,659 | A | 3/1993 | Simons |
| 5,272,057 | A | 12/1993 | Smulson et al. |
| 5,323,907 | A | 6/1994 | Kalvelage |
| 5,882,864 | A | 3/1999 | An et al. |
| 6,218,529 | B1 | 4/2001 | An et al. |
| 2013/0072457 | A1 | 3/2013 | Saxty et al. |
| 2017/0260168 | A1 | 9/2017 | Andrews et al. |

FOREIGN PATENT DOCUMENTS

| | | | |
|---|---|---|---|
| WO | 2008/112408 | A1 | 9/2008 |
| WO | 2011/135376 | A1 | 11/2011 |
| WO | 2014/071419 | A2 | 5/2014 |
| WO | 2014/113729 | A2 | 7/2014 |
| WO | 2015/144803 | A1 | 10/2015 |
| WO | 2015/144804 | A1 | 10/2015 |
| WO | 2015/144808 | A1 | 10/2015 |
| WO | 2016/048833 | A2 | 3/2016 |
| WO | 2016/128411 | A1 | 8/2016 |
| WO | 2016/161239 | A1 | 10/2016 |
| WO | 2017/070708 | A1 | 4/2017 |
| WO | 2018/141921 | A1 | 8/2018 |
| WO | 2018/220206 | A1 | 12/2018 |
| WO | 2020/058432 | A1 | 3/2020 |
| WO | 2020/165181 | A1 | 8/2020 |
| WO | 2020/201138 | A1 | 10/2020 |

OTHER PUBLICATIONS

Loriot, Y. et al. Journal of Clinical Oncology 36(6 suppl):411 (Feb. 26, 2018). (Year: 2018).*

Sethakorn, N. and O'Donnell, P.H. Bju International 118:681-691. (Year: 2016).*

Siefker-Radtke, A.O. et al. Journal of Clinical Oncology 36(15 suppl):4503 (Jun. 1, 2018). (Year: 2018).*

Nicolas-Metral, V. et al. Cancer Research 75(15_Supplement):CT228. Aug. 2015. (Year: 2015).*

Alissa Poh., "Erdafitinib Efficacious in Bladder Cancer : Cancer Discovery," Cancer Discovery Aug. 2018, vol. 8, Issue 8,Jan. 1, 2018. pages 1-5.

Aya Kikuchi et al., "ASP5878, a selective FGFR inhibitor, to treat FGFR3-dependent urothelial cancer with or without chemoresi stance," Cancer Science, vol. 108, No. 2,Feb. 1, 2017, pp. 236-242.

Gopa Iyer et al., "Fibroblast growth factor receptor-3 in urothelial tumorigenesis," Urologic Oncology: Seminars and Original Investigations, vol. 31, No. 3, Apr. 1, 2013, pp. 303-311.

Gust K M et al: "Fibroblast growth factor receptor 3 is a rational therapeutic target in bladder cancer," Molecular Cancer Therapeutics, American Association for Cancer Research, US, vol. 12, No. 7, Jul. 1, 2013, pp. 1245-1254.

Hanna, K.S., "Updates and novel treatments in urothelialcarcinoma," Journal of Oncology Pharmacy Practice, vol. 25, No. 3, Oct. 10, 2018, pp. 648-656.

Josep Tabernero et al., "Phase I Dose-Escalation Study of JNJ-42756493, an Oral Pan-Fibroblast Growth Factor Receptor Inhibitor, in Patients With Advanced Solid Tumors," Journal of Clinical Oncology, vol. 33, No. 30, Oct. 20, 2015, pp. 3401-3408.

Lamont F R et al., "Small molecule FGF receptor inhibitors block FGFR-dependent urothelial carcinoma growth in vitro and in vivo," British Journal of Cancer, Nature Publishing Group, GB, vol. 104, No. 1, Jan. 1, 2011, pp. 75-82.

Lucia Nogova et al., "Evaluation of BGJ398, a Fibroblast Growth Factor Receptor 1-3 Kinase Inhibitor, in Patients With Advanced Solid Tumors Harboring Genetic Alterations in Fibroblast Growth Factor Receptors: Results of a Global Phase 1, Dose-Escalation and Dose-Expansion Study," Journal of Clinical Oncology, vol. 35, No. 2, Jan. 10, 2017, pp. 157-165.

Makito Miyake et al: "1-tert-Butyl-3-[6-(3,5-dimethoxy-phenyl)-2-(4-diethylaminobutylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and G1/G0 Arrest," Journal of Pharmacology and Experimental Therapeutics, vol. 332, No. 3, Dec. 2, 2009, pp. 795-802.

Van Rhijn Bas W G et al., "Molecular grading of urothelial cell carcinoma with fibroblast growth factor receptor 3 and MIB-1 is superior to pathologic grade for the prediction of clinical outcome," Journal of Clinical Oncology : Official Journal of the American Society of Clinical Oncology, May 15, 2003, vol. 21, No. 10, May 15, 2003, pp. 1912-1921.

Angerer et al., "Tissue-Specific Gene Expression: Demonstration of Tissue-Specific Expression by in Situ Hybridization.", Meth. Enzymol., 1987, vol. 152, pp. 649-661.

Ausubel et al., "Informatics for Molecular Biologists", Current Protocols in Molecular Biology, John Wiley & Sons Inc, 2004, pp. 19.0.1-19.0.2.

Bartlett et al., "Technical Overview, Molecular Diagnosis of Cancer, Methods and Protocols", Second Edition, Series: Methods in Molecular Medicine, ISBN: 1-59259-760-2; Mar. 2004, pp. 77-88.

Bello et al., "E-3810 Is a Potent Dual Inhibitor of VEG FR and FGFR that Exerts Antitumor Activity in Multiple Preclinical Models. ", Cancer Res., Feb. 2011, vol. 71, No. 4, pp. 1396-1405.

Deprimo et al. "Expression profiling of blood samples from an SU5416 Phase III metastatic colorectal cancer clinical trial: a novel strategy for biomarker identification," BMC Cancer, vol. 3, 2003, 3, pp. 1-12.

Innis et al., "PCR Protocols: A Guide to Methods and Applications", Academic Press, Inc., 1990, p. 1.

Knights et al., "De-regulated FGF receptors as therapeutic targets in cancer", Pharmacology and Therapeutics, 2010, vol. 125, No. 1, pp. 105-117.

Korc et al., "The Role of Fibroblast Growth Factors in Tumor Growth", Current Cancer Drug Targets, 2009, vol. 9 No. 5, pp. 639-651.

Orre et al., "VEGF, VEGFR-1, VEGFR-2, Microvessel Density and Endothelial Cell Proliferation in Tumours of the Ovary", Int. J. Cancer, 1999, vol. 84, No. 2, pp. 101-108.

Sambrook et al., "Molecular Cloning: A Laboratory Manual", 3rd Ed., Cold Spring Harbor Laboratory Press, 2001, pp. 1-21.

Hallinan et al., "Targeting the fibroblast growth factor receptor family in cancer", Cancer Treat Rev., 2016, vol. 46, pp. 51-62.

Loriot et al., "Erdafitinib compared with vinflunine or docetaxel or pembrolizumab in patients (pts) with metastatic or surgically unresectable (M/UR) urothelial carcinoma (UC) and selected fgfr gene alterations (FGFRalt): The phase III Thor study", Annals of Oncology, vol. 29, No. 8, Oct. 2018, 920TiP, viii327-viii328.

Nassar et al., "Sequential Response to FGFR3 Inhibition with Subsequent Exceptional Response to Atezolizumab in a Patient with FGFR3-TACC3 Fusion-Positive Metastatic Urothelial Carcinoma", JCO Precision Oncology, vol. 2, 2018, pp. 1-6.

Soria et al., "Safety and activity of the pan-fibroblast growth factor receptor (FGFR) inhibitor erdafitinib in phase 1 study patients with advanced urothelial carcinoma," Annals of Oncology, 2016, vol. 27, suppl. 6, p. vi269.

An Efficacy and Safety Study of JNJ-42756493 in Participants With Urothelial Cancer, ClinicalTrials.gov, NCT02365597, retrieved at https://clinicaltrials.gov/ct2/history/NCT02365597?V_32=View, Jan. 21, 2017, 11 pages.

Bahleda et al., "Phase 1 study of JNJ-42756493, a pan-fibroblast growth factor receptor (FGFR) inhibitor, in Patients with advanced solid tumors," Journal of Clinical Oncology, 2014, vol. 32, Issue 15, Suppl; 4 pages.

Dienstmann et al., Genomic aberrations in FGFR pathway: opportunities for targeted therapies in solid tumors, Annals of Oncology, 2013, vol. 25, 552-563.

Heroult et al., "Fibroblast Growth Factor Receptor Signaling in Cancer Biology and Treatment", Current Signal Transduction Therapy, vol. 9, No. 1, 2014, pp. 15-25.

(56) References Cited

OTHER PUBLICATIONS

NCT01703481, "A Study to Evaluate the Safety, Pharmacokinetics, and Pharmacodynamics of JNJ-42756493 in Adult Participants With Advanced or Refractory Solid Tumors or Lymphoma", 2012, ClinicalTrials.gov, 19 pages (Year: 2012).

Tomohiro et al., "Safety pharmacokinetic, and pharmacodynamics of erdafitnib, a pan-fibroblast growth factor receptor (FGFR) tyrosine kinase inhibitor, in patients with advanced or refractory solid tumors," Investigational New Drugs, vol. 36, No. 3, Sep. 30, 2017, pp. 424-434.

* cited by examiner

[a]Patients in the selected regimen were further uptitrated to 9 mg/d if they had not reached 5.5 mg/dL serum phosphate level by Day 14 and if they had no TRAEs.

Median OS = 7.5 months (95% CI, 6.0 to 10.7)

Median OS = 8.6 months (95% CI, 6.5 to 9.7)

SEQUENCE LISTING

```
<160> NUMBER OF SEQ ID NOS: 38

<210> SEQ ID NO 1
<211> LENGTH: 268
<212> TYPE: DNA
<213> ORGANISM: Homo sapiens
<220> FEATURE:
<221> NAME/KEY: source
<222> LOCATION: 1..268
<223> OTHER INFORMATION: /organism="Homo sapiens"
      /mol_type="unassigned DNA"

<400> SEQUENCE: 1

tcggaccgcg gcaactacac ctgcgtcgtg gagaacaagt ttggcagcat ccggcagacg     60

tacacgctgg acgtgctgga gtgctccccg caccggccca tcctgcaggc ggggctgccg    120

gccaaccaga cggcggtgct gggcagcgac gtggagttcc actgcaaggt gtacagtgac    180

gcacagcccc acatccagtg gctcaagcac gtggaggtga atggcagcaa ggtgggcccg    240

gacggcacac cctacgttac cgtgctca                                       268


<210> SEQ ID NO 2
<211> LENGTH: 378
<212> TYPE: DNA
<213> ORGANISM: Homo sapiens
<220> FEATURE:
<221> NAME/KEY: source
<222> LOCATION: 1..378
<223> OTHER INFORMATION: /organism="Homo sapiens"
      /mol_type="unassigned DNA"

<400> SEQUENCE: 2

gaccgcggca actacacctg cgtcgtggag aacaagtttg gcagcatccg gcagacgtac     60

acgctggacg tgctgggtga gggccctggg gcggcgcggg ggtgggggcg gcagtggcgg    120

tggtggtgag ggagggggtg gcccctgagc gtcatctgcc cccacagagc gctgcccgca    180

ccggcccatc ctgcaggcgg ggctgccggc caaccagacg gcggtgctgg gcagcgacgt    240

ggagttccac tgcaaggtgt acagtgacgc acagccccac atccagtggc tcaagcacgt    300

ggaggtgaat ggcagcaagg tgggcccgga cggcacaccc tacgttaccg tgctcaaggt    360

gggccaccgt gtgcacgt                                                  378


<210> SEQ ID NO 3
<211> LENGTH: 234
<212> TYPE: DNA
<213> ORGANISM: Homo sapiens
<220> FEATURE:
<221> NAME/KEY: source
<222> LOCATION: 1..234
<223> OTHER INFORMATION: /organism="Homo sapiens"
```

/mol_type="unassigned DNA"

<400> SEQUENCE: 3
gcgggcaatt ctattgggtt ttctcatcac tctgcgtggc tggtggtgct gccagccgag 60
gaggagctgg tggaggctga cgaggcgtgc agtgtgtatg caggcatcct cagctacggg 120
gtgggcttct tcctgttcat cctggtggtg gcggctgtga cgctctgccg cctgcgcagc 180
ccccccaaga aaggcctggg ctcccccacc gtgcacaaga tctcccgctt cccg 234

<210> SEQ ID NO 4
<211> LENGTH: 301
<212> TYPE: DNA
<213> ORGANISM: Homo sapiens
<220> FEATURE:
<221> NAME/KEY: source
<222> LOCATION: 1..301
<223> OTHER INFORMATION: /organism="Homo sapiens"
/mol_type="unassigned DNA"

<400> SEQUENCE: 4
ctagaggttc tctccttgca caacgtcacc tttgaggacg ccggggagta cacctgcctg 60
gcgggcaatt ctattgggtt ttctcatcac tctgcgtggc tggtggtgct gccagccgag 120
gaggagctgg tggaggctga cgaggcgggc agtgtgtgtg caggcatcct cagctacggg 180
gtgggcttct tcctgttcat cctggtggtg gcggctgtga cgctctgccg cctgcgcagc 240
ccccccaaga aaggcctggg ctcccccacc gtgcacaaga tctcccgctt cccgctcaag 300
c 301

<210> SEQ ID NO 5
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
/note="Description of Artificial Sequence: Synthetic primer"
/mol_type="unassigned DNA"

<400> SEQUENCE: 5
gacctggacc gtgtccttac c 21

<210> SEQ ID NO 6
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
/note="Description of Artificial Sequence: Synthetic primer"
/mol_type="unassigned DNA"

<400> SEQUENCE: 6
cttccccagt tccaggttct t 21

<210> SEQ ID NO 7
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
/note="Description of Artificial Sequence: Synthetic primer"

/mol_type="unassigned DNA"

<400> SEQUENCE: 7
aggacctgga ccgtgtcctt 20

<210> SEQ ID NO 8
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
/note="Description of Artificial Sequence: Synthetic primer"
/mol_type="unassigned DNA"

<400> SEQUENCE: 8
tataggtccg gtggacaggg 20

<210> SEQ ID NO 9
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
/note="Description of Artificial Sequence: Synthetic primer"
/mol_type="unassigned DNA"

<400> SEQUENCE: 9
ctggaccgtg tccttaccgt 20

<210> SEQ ID NO 10
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
/note="Description of Artificial Sequence: Synthetic primer"
/mol_type="unassigned DNA"

<400> SEQUENCE: 10
gcagcccagg attgaactgt 20

<210> SEQ ID NO 11
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /organism="Artificial Sequence"
/note="Description of Artificial Sequence: Synthetic primer"
/mol_type="unassigned DNA"

<400> SEQUENCE: 11
tggatcgaat tctcactctc aca 23

<210> SEQ ID NO 12
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"

-continued

/note="Description of Artificial Sequence: Synthetic primer"
/mol_type="unassigned DNA"

<400> SEQUENCE: 12
gccaagcaat ctgcgtattt g 21

<210> SEQ ID NO 13
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /organism="Artificial Sequence"
/note="Description of Artificial Sequence: Synthetic primer"
/mol_type="unassigned DNA"

<400> SEQUENCE: 13
gctcttcaat acagccctga tca 23

<210> SEQ ID NO 14
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /organism="Artificial Sequence"
/note="Description of Artificial Sequence: Synthetic primer"
/mol_type="unassigned DNA"

<400> SEQUENCE: 14
acttggatcg aattctcact ctca 24

<210> SEQ ID NO 15
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /organism="Artificial Sequence"
/note="Description of Artificial Sequence: Synthetic primer"
/mol_type="unassigned DNA"

<400> SEQUENCE: 15
tggatcgaat tctcactctc aca 23

<210> SEQ ID NO 16
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /organism="Artificial Sequence"
/note="Description of Artificial Sequence: Synthetic primer"
/mol_type="unassigned DNA"

<400> SEQUENCE: 16
gcaaagcctg aattttcttg aataa 25

<210> SEQ ID NO 17
<211> LENGTH: 18
<212> TYPE: DNA
<213> ORGANISM: Artificial Sequence
<220> FEATURE:
<221> NAME/KEY: source
<222> LOCATION: 1..18

<223> OTHER INFORMATION: /organism="Artificial Sequence"
/note="Description of Artificial Sequence: Synthetic primer"
/mol_type="unassigned DNA"

<400> SEQUENCE: 17
gcatccggca gacgtaca 18

<210> SEQ ID NO 18
<211> LENGTH: 15
<212> TYPE: DNA
<213> ORGANISM: Artificial Sequence
<220> FEATURE:
<221> NAME/KEY: source
<222> LOCATION: 1..15
<223> OTHER INFORMATION: /organism="Artificial Sequence"
/note="Description of Artificial Sequence: Synthetic primer"
/mol_type="unassigned DNA"

<400> SEQUENCE: 18
ccccgcctgc aggat 15

<210> SEQ ID NO 19
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /organism="Artificial Sequence"
/note="Description of Artificial Sequence: Synthetic primer"
/mol_type="unassigned DNA"

<400> SEQUENCE: 19
gcatccggca gacgtaca 18

<210> SEQ ID NO 20
<211> LENGTH: 15
<212> TYPE: DNA
<213> ORGANISM: Artificial Sequence
<220> FEATURE:
<221> NAME/KEY: source
<222> LOCATION: 1..15
<223> OTHER INFORMATION: /organism="Artificial Sequence"
/note="Description of Artificial Sequence: Synthetic primer"
/mol_type="unassigned DNA"

<400> SEQUENCE: 20
ccccgcctgc aggat 15

<210> SEQ ID NO 21
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /organism="Artificial Sequence"
/note="Description of Artificial Sequence: Synthetic primer"
/mol_type="unassigned DNA"

<400> SEQUENCE: 21
aggagctggt ggaggctga 19

<210> SEQ ID NO 22
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /organism="Artificial Sequence"
/note="Description of Artificial Sequence: Synthetic primer"
/mol_type="unassigned DNA"

<400> SEQUENCE: 22
ccgtagctga ggatgcctg 19

<210> SEQ ID NO 23
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /organism="Artificial Sequence"
/note="Description of Artificial Sequence: Synthetic primer"
/mol_type="unassigned DNA"

<400> SEQUENCE: 23
ctggtggagg ctgacgag 18

<210> SEQ ID NO 24
<211> LENGTH: 16
<212> TYPE: DNA
<213> ORGANISM: Artificial Sequence
<220> FEATURE:
<221> NAME/KEY: source
<222> LOCATION: 1..16
<223> OTHER INFORMATION: /organism="Artificial Sequence"
/note="Description of Artificial Sequence: Synthetic primer"
/mol_type="unassigned DNA"

<400> SEQUENCE: 24
agcccacccc gtagct 16

<210> SEQ ID NO 25
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
/note="Description of Artificial Sequence: Synthetic primer"
/mol_type="unassigned DNA"

<400> SEQUENCE: 25
gtcgtggaga acaagtttgg c 21

<210> SEQ ID NO 26
<211> LENGTH: 17
<212> TYPE: DNA
<213> ORGANISM: Artificial Sequence
<220> FEATURE:
<221> NAME/KEY: source
<222> LOCATION: 1..17
<223> OTHER INFORMATION: /organism="Artificial Sequence"
/note="Description of Artificial Sequence: Synthetic primer"
/mol_type="unassigned DNA"

<400> SEQUENCE: 26
gtctggttgg ccggcag 17

<210> SEQ ID NO 27
<211> LENGTH: 21
<212> TYPE: DNA
<213> ORGANISM: Artificial Sequence
<220> FEATURE:

```
<221> NAME/KEY: source
<222> LOCATION: 1..21
<223> OTHER INFORMATION: /organism="Artificial Sequence"
      /note="Description of Artificial Sequence: Synthetic primer"
      /mol_type="unassigned DNA"

<400> SEQUENCE: 27

gtcgtggaga acaagtttgg c                                              21


<210> SEQ ID NO 28
<211> LENGTH: 17
<212> TYPE: DNA
<213> ORGANISM: Artificial Sequence
<220> FEATURE:
<221> NAME/KEY: source
<222> LOCATION: 1..17
<223> OTHER INFORMATION: /organism="Artificial Sequence"
      /note="Description of Artificial Sequence: Synthetic primer"
      /mol_type="unassigned DNA"

<400> SEQUENCE: 28

gtctggttgg ccggcag                                                   17


<210> SEQ ID NO 29
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /organism="Artificial Sequence"
      /note="Description of Artificial Sequence: Synthetic primer"
      /mol_type="unassigned DNA"

<400> SEQUENCE: 29

aggagctggt ggaggctga                                                 19


<210> SEQ ID NO 30
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /organism="Artificial Sequence"
      /note="Description of Artificial Sequence: Synthetic primer"
      /mol_type="unassigned DNA"

<400> SEQUENCE: 30

ccgtagctga ggatgcctg                                                 19


<210> SEQ ID NO 31
<211> LENGTH: 16
<212> TYPE: DNA
<213> ORGANISM: Artificial Sequence
<220> FEATURE:
<221> NAME/KEY: source
<222> LOCATION: 1..16
<223> OTHER INFORMATION: /organism="Artificial Sequence"
      /note="Description of Artificial Sequence: Synthetic primer"
      /mol_type="unassigned DNA"

<400> SEQUENCE: 31

gacgaggcgg gcagtg                                                    16


<210> SEQ ID NO 32
<211> LENGTH: 19
<212> TYPE: DNA
<213> ORGANISM: Artificial Sequence
```

<220> FEATURE:
<221> NAME/KEY: source
<222> LOCATION: 1..19
<223> OTHER INFORMATION: /organism="Artificial Sequence"
/note="Description of Artificial Sequence: Synthetic primer"
/mol_type="unassigned DNA"

<400> SEQUENCE: 32
gaagaagccc accccgtag 19

<210> SEQ ID NO 33
<211> LENGTH: 2850
<212> TYPE: DNA
<213> ORGANISM: Homo sapiens
<220> FEATURE:
<221> NAME/KEY: source
<222> LOCATION: 1..2850
<223> OTHER INFORMATION: /organism="Homo sapiens"
/mol_type="unassigned DNA"

<400> SEQUENCE: 33
atgggcgccc ctgcctgcgc cctcgcgctc tgcgtggccg tggccatcgt ggccggcgcc 60
tcctcggagt ccttggggac ggagcagcgc gtcgtggggc gagcggcaga agtcccgggc 120
ccagagcccg gccagcagga gcagttggtc ttcggcagcg gggatgctgt ggagctgagc 180
tgtcccccgc ccgggggtgg tcccatgggg cccactgtct gggtcaagga tggcacaggg 240
ctggtgccct cggagcgtgt cctggtgggg ccccagcggc tgcaggtgct gaatgcctcc 300
cacgaggact ccggggccta cagctgccgg cagcggctca cgcagcgcgt actgtgccac 360
ttcagtgtgc gggtgacaga cgctccatcc tcgggagatg acgaagacgg ggaggacgag 420
gctgaggaca caggtgtgga cacaggggcc ccttactgga cacggcccga gcggatggac 480
aagaagctgc tggccgtgcc ggccgccaac accgtccgct tccgctgccc agccgctggc 540
aaccccactc cctccatctc ctggctgaag aacggcaggg agttccgcgg cgagcaccgc 600
attggaggca tcaagctgcg gcatcagcag tggagcctgg tcatggaaag cgtggtgccc 660
tcggaccgcg gcaactacac ctgcgtcgtg gagaacaagt ttggcagcat ccggcagacg 720
tacacgctgg acgtgctgga gcgctccccg caccggccca tcctgcaggc ggggctgccg 780
gccaaccaga cggcggtgct gggcagcgac gtggagttcc actgcaaggt gtacagtgac 840
gcacagcccc acatccagtg gctcaagcac gtggaggtga atggcagcaa ggtgggcccg 900
gacggcacac cctacgttac cgtgctcaag acggcgggcg ctaacaccac cgacaaggag 960
ctagaggttc tctccttgca caacgtcacc tttgaggacg ccggggagta cacctgcctg 1020
gcgggcaatt ctattgggtt ttctcatcac tctgcgtggc tggtggtgct gccagccgag 1080
gaggagctgg tggaggctga cgaggcgggc agtgtgtatg caggcatcct cagctacggg 1140
gtgggcttct tcctgttcat cctggtggtg gcggctgtga cgctctgccg cctgcgcagc 1200
ccccccaaga aaggcctggg ctcccccacc gtgcacaaga tctcccgctt cccgctcaag 1260
cgacaggtgt ccctggagtc caacgcgtcc atgagctcca acacaccact ggtgcgcatc 1320
gcaaggctgt cctcagggga gggccccacg ctggccaatg tctccgagct cgagctgcct 1380
gccgacccca aatgggagct gtctcgggcc cggctgaccc tgggcaagcc ccttggggag 1440
ggctgcttcg gccaggtggt catggcggag gccatcggca ttgacaagga ccgggccgcc 1500
aagcctgtca ccgtagccgt gaagatgctg aaagacgatg ccactgacaa ggacctgtcg 1560
gacctggtgt ctgagatgga gatgatgaag atgatcggga aacacaaaaa catcatcaac 1620
ctgctgggcg cctgcacgca gggcgggccc ctgtacgtgc tggtggagta cgcggccaag 1680
ggtaacctgc gggagtttct gcgggcgcgg cggcccccgg gcctggacta ctccttcgac 1740
acctgcaagc cgcccgagga gcagctcacc ttcaaggacc tggtgtcctg tgcctaccag 1800
gtggcccggg gcatggagta cttggcctcc cagaagtgca tccacaggga cctggctgcc 1860
cgcaatgtgc tggtgaccga ggacaacgtg atgaagatcg cagacttcgg gctggcccgg 1920
gacgtgcaca acctcgacta ctacaagaag acgaccaacg gccggctgcc cgtgaagtgg 1980
atggcgcctg aggccttgtt tgaccgagtc tacactcacc agagtgacgt ctggtccttt 2040
ggggtcctgc tctgggagat cttcacgctg gggggctccc cgtaccccgg catccctgtg 2100
gaggagctct tcaagctgct gaaggagggc caccgcatgg acaagcccgc caactgcaca 2160
cacgacctgt acatgatcat gcgggagtgc tggcatgccg cgccctccca gaggcccacc 2220
ttcaagcagc tggtggagga cctggaccgt gtccttaccg tgacgtccac cgacgtaaag 2280
gcgacacagg aggagaaccg ggagctgagg agcaggtgtg aggagctcca cgggaagaac 2340
ctggaactgg ggaagatcat ggacaggttc gaagaggttg tgtaccaggc catggaggaa 2400
gttcagaagc agaaggaact ttccaaagct gaaatccaga aagttctaaa agaaaaagac 2460
caacttacca cagatctgaa ctccatggag aagtccttct ccgacctctt caagcgtttt 2520
gagaaacaga aagaggtgat cgagggctac cgcaagaacg aagagtcact gaagaagtgc 2580
gtggaggatt acctggcaag gatcacccag gagggccaga ggtaccaagc cctgaaggcc 2640
cacgcggagg agaagctgca gctggcaaac gaggagatcg cccaggtccg gagcaaggcc 2700
caggcggaag cgttggccct ccaggccagc ctgaggaagg agcagatgcg catccagtcg 2760
ctggagaaga cagtggagca gaagactaaa gagaacgagg agctgaccag gatctgcgac 2820
gacctcatct ccaagatgga gaagatctga 2850

<210> SEQ ID NO 34
<211> LENGTH: 2955
<212> TYPE: DNA
<213> ORGANISM: Homo sapiens
<220> FEATURE:
<221> NAME/KEY: source
<222> LOCATION: 1..2955
<223> OTHER INFORMATION: /organism="Homo sapiens"
/mol_type="unassigned DNA"

<400> SEQUENCE: 34
atgggcgccc ctgcctgcgc cctcgcgctc tgcgtggccg tggccatcgt ggccggcgcc 60
tcctcggagt ccttggggac ggagcagcgc gtcgtggggc gagcggcaga agtcccgggc 120
ccagagcccg gccagcagga gcagttggtc ttcggcagcg gggatgctgt ggagctgagc 180
tgtcccccgc ccgggggtgg tcccatgggg cccactgtct gggtcaagga tggcacaggg 240
ctggtgccct cggagcgtgt cctggtgggg ccccagcggc tgcaggtgct gaatgcctcc 300
cacgaggact ccggggccta cagctgccgg cagcggctca cgcagcgcgt actgtgccac 360
ttcagtgtgc gggtgacaga cgctccatcc tcgggagatg acgaagacgg ggaggacgag 420
gctgaggaca caggtgtgga cacaggggcc ccttactgga cacggcccga gcggatggac 480
aagaagctgc tggccgtgcc ggccgccaac accgtccgct tccgctgccc agccgctggc 540
aaccccactc cctccatctc ctggctgaag aacggcaggg agttccgcgg cgagcaccgc 600
attggaggca tcaagctgcg gcatcagcag tggagcctgg tcatggaaag cgtggtgccc 660
tcggaccgcg gcaactacac ctgcgtcgtg gagaacaagt ttggcagcat ccggcagacg 720
tacacgctgg acgtgctgga gcgctccccg caccggccca tcctgcaggc ggggctgccg 780

```
gccaaccaga cggcggtgct gggcagcgac gtggagttcc actgcaaggt gtacagtgac    840
gcacagcccc acatccagtg gctcaagcac gtggaggtga atggcagcaa ggtgggcccg    900
gacggcacac cctacgttac cgtgctcaag acggcgggcg ctaacaccac cgacaaggag    960
ctagaggttc tctccttgca caacgtcacc tttgaggacg ccggggagta cacctgcctg   1020
gcgggcaatt ctattgggtt ttctcatcac tctgcgtggc tggtggtgct gccagccgag   1080
gaggagctgg tggaggctga cgaggcgggc agtgtgtatg caggcatcct cagctacggg   1140
gtgggcttct tcctgttcat cctggtggtg gcggctgtga cgctctgccg cctgcgcagc   1200
ccccccaaga aaggcctggg ctcccccacc gtgcacaaga tctcccgctt cccgctcaag   1260
cgacaggtgt ccctggagtc caacgcgtcc atgagctcca acacaccact ggtgcgcatc   1320
gcaaggctgt cctcagggga gggccccacg ctggccaatg tctccgagct cgagctgcct   1380
gccgacccca aatgggagct gtctcgggcc cggctgaccc tgggcaagcc ccttggggag   1440
ggctgcttcg gccaggtggt catggcggag gccatcggca ttgacaagga ccgggccgcc   1500
aagcctgtca ccgtagccgt gaagatgctg aaagacgatg ccactgacaa ggacctgtcg   1560
gacctggtgt ctgagatgga gatgatgaag atgatcggga aacacaaaaa catcatcaac   1620
ctgctgggcg cctgcacgca gggcgggccc ctgtacgtgc tggtggagta cgcggccaag   1680
ggtaacctgc gggagtttct gcgggcgcgg cggcccccgg gcctggacta ctccttcgac   1740
acctgcaagc cgcccgagga gcagctcacc ttcaaggacc tggtgtcctg tgcctaccag   1800
gtggcccggg gcatggagta cttggcctcc cagaagtgca tccacaggga cctggctgcc   1860
cgcaatgtgc tggtgaccga ggacaacgtg atgaagatcg cagacttcgg gctggcccgg   1920
gacgtgcaca acctcgacta ctacaagaag acgaccaacg gccggctgcc cgtgaagtgg   1980
atggcgcctg aggccttgtt tgaccgagtc tacactcacc agagtgacgt ctggtccttt   2040
ggggtcctgc tctgggagat cttcacgctg gggggctccc cgtaccccgg catccctgtg   2100
gaggagctct tcaagctgct gaaggagggc caccgcatgg acaagcccgc caactgcaca   2160
cacgacctgt acatgatcat gcgggagtgc tggcatgccg cgccctccca gaggcccacc   2220
ttcaagcagc tggtggagga cctggaccgt gtccttaccg tgacgtccac cgacgtgcca   2280
ggcccacccc caggtgttcc cgcgcctggg ggcccacccc tgtccaccgg acctatagtg   2340
gacctgctcc agtacagcca gaaggacctg gatgcagtgg taaaggcgac acaggaggag   2400
aaccgggagc tgaggagcag gtgtgaggag ctccacggga agaacctgga actggggaag   2460
atcatggaca ggttcgaaga ggttgtgtac caggccatgg aggaagttca gaagcagaag   2520
gaactttcca aagctgaaat ccagaaagtt ctaaaagaaa aagaccaact taccacagat   2580
ctgaactcca tggagaagtc cttctccgac ctcttcaagc gttttgagaa acagaaagag   2640
gtgatcgagg gctaccgcaa gaacgaagag tcactgaaga agtgcgtgga ggattacctg   2700
gcaaggatca cccaggaggg ccagaggtac caagccctga aggcccacgc ggaggagaag   2760
ctgcagctgg caaacgagga gatcgcccag gtccggagca aggcccaggc ggaagcgttg   2820
gccctccagg ccagcctgag gaaggagcag atgcgcatcc agtcgctgga gaagacagtg   2880
gagcagaaga ctaaagagaa cgaggagctg accaggatct gcgacgacct catctccaag   2940
atggagaaga tctga                                                    2955
```

<210> SEQ ID NO 35
<211> LENGTH: 3765
<212> TYPE: DNA

<213> ORGANISM: Homo sapiens
<220> FEATURE:
<221> NAME/KEY: source
<222> LOCATION: 1..3765
<223> OTHER INFORMATION: /organism="Homo sapiens"
/mol_type="unassigned DNA"

<400> SEQUENCE: 35
atgggcgccc ctgcctgcgc cctcgcgctc tgcgtggccg tggccatcgt ggccggcgcc 60
tcctcggagt ccttggggac ggagcagcgc gtcgtggggc gagcggcaga agtcccgggc 120
ccagagcccg gccagcagga gcagttggtc ttcggcagcg gggatgctgt ggagctgagc 180
tgtcccccgc ccgggggtgg tcccatgggg cccactgtct gggtcaagga tggcacaggg 240
ctggtgccct cggagcgtgt cctggtgggg ccccagcggc tgcaggtgct gaatgcctcc 300
cacgaggact ccggggccta cagctgccgg cagcggctca cgcagcgcgt actgtgccac 360
ttcagtgtgc gggtgacaga cgctccatcc tcgggagatg acgaagacgg ggaggacgag 420
gctgaggaca caggtgtgga cacaggggcc ccttactgga cacggcccga gcggatggac 480
aagaagctgc tggccgtgcc ggccgccaac accgtccgct tccgctgccc agccgctggc 540
aaccccactc cctccatctc ctggctgaag aacggcaggg agttccgcgg cgagcaccgc 600
attggaggca tcaagctgcg gcatcagcag tggagcctgg tcatggaaag cgtggtgccc 660
tcggaccgcg gcaactacac ctgcgtcgtg gagaacaagt ttggcagcat ccggcagacg 720
tacacgctgg acgtgctgga gcgctccccg caccggccca tcctgcaggc ggggctgccg 780
gccaaccaga cggcggtgct gggcagcgac gtggagttcc actgcaaggt gtacagtgac 840
gcacagcccc acatccagtg gctcaagcac gtggaggtga atggcagcaa ggtgggcccg 900
gacggcacac cctacgttac cgtgctcaag tcctggatca gtgagagtgt ggaggccgac 960
gtgcgcctcc gcctggccaa tgtgtcggag cgggacgggg gcgagtacct ctgtcgagcc 1020
accaatttca taggcgtggc cgagaaggcc ttttggctga gcgttcacgg gccccgagca 1080
gccgaggagg agctggtgga ggctgacgag gcgggcagtg tgtatgcagg catcctcagc 1140
tacggggtgg gcttcttcct gttcatcctg gtggtggcgg ctgtgacgct ctgccgcctg 1200
cgcagccccc ccaagaaagg cctgggctcc ccccaccgtgc acaagatctc ccgcttcccg 1260
ctcaagcgac aggtgtccct ggagtccaac gcgtccatga gctccaacac accactggtg 1320
cgcatcgcaa ggctgtcctc aggggagggc cccacgctgg ccaatgtctc cgagctcgag 1380
ctgcctgccg accccaaatg ggagctgtct cgggcccggc tgaccctggg caagcccctt 1440
ggggagggct gcttcggcca ggtggtcatg gcggaggcca tcggcattga caaggaccgg 1500
gccgccaagc ctgtcaccgt agccgtgaag atgctgaaag acgatgccac tgacaaggac 1560
ctgtcggacc tggtgtctga gatggagatg atgaagatga tcgggaaaca caaaaacatc 1620
atcaacctgc tgggcgcctg cacgcagggc gggcccctgt acgtgctggt ggagtacgcg 1680
gccaagggta acctgcggga gtttctgcgg gcgcggcggc ccccgggcct ggactactcc 1740
ttcgacacct gcaagccgcc cgaggagcag ctcaccttca aggacctggt gtcctgtgcc 1800
taccaggtgg cccggggcat ggagtacttg gcctcccaga agtgcatcca cagggacctg 1860
gctgcccgca atgtgctggt gaccgaggac aacgtgatga agatcgcaga cttcgggctg 1920
gcccgggacg tgcacaacct cgactactac aagaagacga ccaacggccg gctgcccgtg 1980
aagtggatgg cgcctgaggc cttgtttgac cgagtctaca ctcaccagag tgacgtctgg 2040
tcctttgggg tcctgctctg ggagatcttc acgctggggg gctccccgta ccccggcatc 2100

```
cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca agcagctggt ggaggacctg gaccgtgtcc ttaccgtgac gtccaccgac   2280
aatgttatgg aacagttcaa tcctgggctg cgaaatttaa taaacctggg gaaaaattat   2340
gagaaagctg taaacgctat gatcctggca ggaaaagcct actacgatgg agtggccaag   2400
atcggtgaga ttgccactgg gtcccccgtg tcaactgaac tgggacatgt cctcatagag   2460
atttcaagta cccacaagaa actcaacgag agtcttgatg aaaattttaa aaaattccac   2520
aaagagatta tccatgagct ggagaagaag atagaacttg acgtgaaata tatgaacgca   2580
actctaaaaa gataccaaac agaacacaag aataaattag agtctttgga gaaatcccaa   2640
gctgagttga agaagatcag aaggaaaagc caaggaagcc gaaacgcact caaatatgaa   2700
cacaaagaaa ttgagtatgt ggagaccgtt acttctcgtc agagtgaaat ccagaaattc   2760
attgcagatg gttgcaaaga ggctctgctt gaagagaaga ggcgcttctg ctttctggtt   2820
gataagcact gtggctttgc aaaccacata cattattatc acttacagtc tgcagaacta   2880
ctgaattcca agctgcctcg gtggcaggag acctgtgttg atgccatcaa agtgccagag   2940
aaaatcatga atatgatcga agaaataaag accccagcct ctacccccgt gtctggaact   3000
cctcaggctt cacccatgat cgagagaagc aatgtggtta ggaaagatta cgacaccctt   3060
tctaaatgct caccaaagat gcccccccgct ccttcaggca gagcatatac cagtcccttg   3120
atcgatatgt ttaataaccc agccacggct gccccgaatt cacaaagggt aaataattca   3180
acaggtactt ccgaagatcc cagtttacag cgatcagttt cggttgcaac gggactgaac   3240
atgatgaaga agcagaaagt gaagaccatc ttcccgcaca ctgcgggctc caacaagacc   3300
ttactcagct ttgcacaggg agatgtcatc acgctgctca tccccgagga gaaggatggc   3360
tggctctatg gagaacacga cgtgtccaag gcgaggggtt ggttcccgtc gtcgtacacg   3420
aagttgctgg aagaaaatga gacagaagca gtgaccgtgc ccacgccaag ccccacacca   3480
gtgagaagca tcagcaccgt gaacttgtct gagaatagca gtgttgtcat ccccccaccc   3540
gactacttgg aatgcttgtc catgggggca gctgccgaca ggagagcaga ttcggccagg   3600
acgacatcca cctttaaggc cccagcgtcc aagcccgaga ccgcggctcc taacgatgcc   3660
aacgggactg caaagccgcc ttttctcagc ggagaaaacc cctttgccac tgtgaaactc   3720
cgcccgactg tgacgaatga tcgctcggca cccatcattc gatga                    3765
```

<210> SEQ ID NO 36
<211> LENGTH: 4989
<212> TYPE: DNA
<213> ORGANISM: Homo sapiens
<220> FEATURE:
<221> NAME/KEY: source
<222> LOCATION: 1..4989
<223> OTHER INFORMATION: /organism="Homo sapiens"
/mol_type="unassigned DNA"

<400> SEQUENCE: 36

```
atggtcagct ggggtcgttt catctgcctg gtcgtggtca ccatggcaac cttgtccctg     60
gcccggccct ccttcagttt agttgaggat accacattag agccagaaga gccaccaacc    120
aaataccaaa tctctcaacc agaagtgtac gtggctgcgc caggggagtc gctagaggtg    180
cgctgcctgt tgaaagatgc cgccgtgatc agttggacta aggatggggt gcacttgggg    240
cccaacaata ggacagtgct tattggggag tacttgcaga taaagggcgc cacgcctaga    300
```

-continued

```
gactccggcc tctatgcttg tactgccagt aggactgtag acagtgaaac ttggtacttc    360
atggtgaatg tcacagatgc catctcatcc ggagatgatg aggatgacac cgatggtgcg    420
gaagattttg tcagtgagaa cagtaacaac aagagagcac catactggac caacacagaa    480
aagatggaaa agcggctcca tgctgtgcct gcggccaaca ctgtcaagtt tcgctgccca    540
gccgggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagg ccgccggtgt taacaccacg    960
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg gaagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320
aacaccccgc tggtgaggat aacaacacgc ctctcttcaa cggcagacac ccccatgctg   1380
gcaggggtct ccgagtatga acttccagag gacccaaaat gggagtttcc aagagataag   1440
ctgacactgg gcaagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga aatgttttgg taacagaaaa caatgtgatg   1920
aaaatagcag actttggact cgccagagat atcaacaata tagactatta caaaaagacc   1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaacttttta agctgctgaa ggaaggacac   2160
agaatggata agccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga gatcatggag gaaacaaata cgcagattgc ttggccatca   2340
aaactgaaga tcggagccaa atccaagaaa gatccccata ttaaggtttc tggaaagaaa   2400
gaagatgtta aagaagccaa ggaaatgatc atgtctgtct tagacacaaa aagcaatcga   2460
gtcacactga agatggatgt ttcacataca gaacattcac atgtaatcgg caaaggtggc   2520
aacaatatta aaaaagtgat ggaagaaacc ggatgccata tccactttcc agattccaac   2580
aggaataacc aagcagaaaa aagcaaccag gtatctatag cgggacaacc agcaggagta   2640
gaatctgccc gagttagaat tcgggagctg cttcctttgg tgctgatgtt tgagctacca   2700
```

-continued

```
attgctggaa ttcttcaacc ggttcctgat cctaattccc cctctattca gcatatatca   2760
caaacgtaca atatttcagt atcatttaaa cagcgttccc gaatgtatgg tgctactgtc   2820
atagtacgag ggtctcagaa taacactagt gctgtgaagg aaggaactgc catgctgtta   2880
gaacatcttg ctgggagctt agcatcagct attcctgtga gcacacaact agatattgca   2940
gctcaacatc atctctttat gatgggtcga aatgggagca acatcaaaca tatcatgcag   3000
agaacaggtg ctcagatcca ctttcctgat cccagtaatc cacaaaagaa atctaccgtc   3060
tacctccagg gcaccattga gtctgtctgt cttgcaaggc aatatctcat gggttgtctt   3120
cctcttgtgt tgatgtttga tatgaaggaa gaaattgaag tagatccaca attcattgcg   3180
cagttgatgg aacagcttga tgtcttcatc agtattaaac caaagcccaa acagccaagc   3240
aagtctgtga ttgtgaaaag tgttgagcga aatgccttaa atatgtatga agcaaggaaa   3300
tgtctcctcg gacttgaaag cagtggggtt accatagcaa ccagtccatc cccagcatcc   3360
tgccctgccg gcctggcatg tcccagcctg gatatcttag cttcagcagg ccttggactc   3420
actggactag gtcttttggg acccaccacc ttatctctga acacttcaac aaccccaaac   3480
tcactcttga atgctcttaa tagctcagtc agtcctttgc aaagtccaag ttctggtaca   3540
cccagcccca cattatgggc acccccactt gctaatactt caagtgccac aggtttttct   3600
gctataccac accttatgat tccatctact gcccaagcca cattaactaa tattttgttg   3660
tctggagtgc ccacctatgg gcacacagct ccatctcccc ctcctggctt gactcctgtt   3720
gatgtccata tcaacagtat gcagaccgaa ggcaaaaaaa tctctgctgc tttaaatgga   3780
catgcacagt ctccagatat aaaatatggt gcaatatcca cttcatcact tggagaaaaa   3840
gtgctgagtg caaatcacgg ggatccgtcc atccagacaa gtgggtctga gcagacatct   3900
cccaaatcaa gccccactga aggttgtaat gatgcttttg ttgaagtagg catgcctcga   3960
agtccttccc attctgggaa tgctggtgac ttgaaacaga tgatgtgtcc ctccaaggtt   4020
tcctgtgcca aaaggcagac agtggaacta ttgcaaggca cgaaaaactc acacttacac   4080
agcactgaca ggttgctctc agaccctgaa ctgagtgcta ccgaaagccc tttggctgac   4140
aagaaggctc cagggagtga gcgcgctgca gagagggcag cagctgccca gcaaaactcc   4200
gaaagggccc accttgctcc acggtcatca tatgtcaaca tgcaggcatt tgactatgaa   4260
cagaagaagc tattagccac caaagctatg ttaaagaaac cagtggtgac ggaggtcaga   4320
acgcccacaa atacctggag tggcctgggt ttttctaaat ccatgccagc tgaaactatc   4380
aaggagttga gaagggccaa tcatgtgtcc tataagccca caatgacaac cacttatgag   4440
ggctcatcca tgtccctttc acggtccaac agtcgtgagc acttgggagg tggaagcgaa   4500
tctgataact ggagagaccg aaatggaatt ggacctggaa gtcatagtga atttgcagct   4560
tctattggca gccctaagcg taaacaaaac aaatcaacgg aacactatct cagcagtagc   4620
aattacatgg actgcatttc ctcgctgaca ggaagcaatg gctgtaactt aaatagctct   4680
ttcaaaggtt ctgacctccc tgagctcttc agcaaactgg gcctgggcaa atacacagat   4740
gttttccagc aacaagagat cgatcttcag acattcctca ctctcacaga tcaggatctg   4800
aaggagctgg gaataactac ttttggtgcc aggaggaaaa tgctgcttgc aatttcagaa   4860
ctaaataaaa accgaagaaa gctttttgaa tcgccaaatg cacgcacctc tttcctggaa   4920
ggtggagcga gtggaaggct accccgtcag tatcactcag acattgctag tgtcagtggc   4980
cgctggtag                                                           4989
```

<210> SEQ ID NO 37
<211> LENGTH: 3213
<212> TYPE: DNA
<213> ORGANISM: Homo sapiens
<220> FEATURE:
<221> NAME/KEY: source
<222> LOCATION: 1..3213
<223> OTHER INFORMATION: /organism="Homo sapiens"
/mol_type="unassigned DNA"

<400> SEQUENCE: 37
atggtcagct ggggtcgttt catctgcctg gtcgtggtca ccatggcaac cttgtccctg 60
gcccggccct ccttcagttt agttgaggat accacattag agccagaaga gccaccaacc 120
aaataccaaa tctctcaacc agaagtgtac gtggctgcgc caggggagtc gctagaggtg 180
cgctgcctgt tgaaagatgc cgccgtgatc agttggacta aggatggggt gcacttgggg 240
cccaacaata ggacagtgct tattggggag tacttgcaga taaagggcgc cacgcctaga 300
gactccggcc tctatgcttg tactgccagt aggactgtag acagtgaaac ttggtacttc 360
atggtgaatg tcacagatgc catctcatcc ggagatgatg aggatgacac cgatggtgcg 420
gaagattttg tcagtgagaa cagtaacaac aagagagcac catactggac caacacagaa 480
aagatggaaa agcggctcca tgctgtgcct gcggccaaca ctgtcaagtt tcgctgccca 540
gccgggggga acccaatgcc aaccatgcgg tggctgaaaa acgggaagga gtttaagcag 600
gagcatcgca ttggaggcta caaggtacga aaccagcact ggagcctcat tatggaaagt 660
gtggtcccat ctgacaaggg aaattatacc tgtgtagtgg agaatgaata cgggtccatc 720
aatcacacgt accacctgga tgttgtggag cgatcgcctc accggcccat cctccaagcc 780
ggactgccgg caaatgcctc cacagtggtc ggaggagacg tagagtttgt ctgcaaggtt 840
tacagtgatg cccagcccca catccagtgg atcaagcacg tggaaaagaa cggcagtaaa 900
tacgggcccg acgggctgcc ctacctcaag gttctcaagg ccgccggtgt taacaccacg 960
gacaaagaga ttgaggttct ctatattcgg aatgtaactt ttgaggacgc tggggaatat 1020
acgtgcttgg cgggtaattc tattgggata tcctttcact ctgcatggtt gacagttctg 1080
ccagcgcctg gaagagaaaa ggagattaca gcttccccag actacctgga gatagccatt 1140
tactgcatag gggtcttctt aatcgcctgt atggtggtaa cagtcatcct gtgccgaatg 1200
aagaacacga ccaagaagcc agacttcagc agccagccgg ctgtgcacaa gctgaccaaa 1260
cgtatccccc tgcggagaca ggtaacagtt tcggctgagt ccagctcctc catgaactcc 1320
aacaccccgc tggtgaggat aacaacacgc ctctcttcaa cggcagacac ccccatgctg 1380
gcaggggtct ccgagtatga acttccagag gacccaaaat gggagtttcc aagagataag 1440
ctgacactgg gcaagcccct gggagaaggt tgctttgggc aagtggtcat ggcggaagca 1500
gtgggaattg acaaagacaa gcccaaggag gcggtcaccg tggccgtgaa gatgttgaaa 1560
gatgatgcca cagagaaaga cctttctgat ctggtgtcag agatggagat gatgaagatg 1620
attgggaaac acaagaatat cataaatctt cttggagcct gcacacagga tgggcctctc 1680
tatgtcatag ttgagtatgc ctctaaaggc aacctccgag aatacctccg agcccggagg 1740
ccacccggga tggagtactc ctatgacatt aaccgtgttc ctgaggagca gatgaccttc 1800
aaggacttgg tgtcatgcac ctaccagctg gccagaggca tggagtactt ggcttcccaa 1860
aaatgtattc atcgagattt agcagccaga aatgttttgg taacagaaaa caatgtgatg 1920
aaaatagcag actttggact cgccagagat atcaacaata tagactatta caaaaagacc 1980

-continued

```
accaatgggc ggcttccagt caagtggatg gctccagaag ccctgtttga tagagtatac   2040

actcatcaga gtgatgtctg gtccttcggg gtgttaatgt gggagatctt cactttaggg   2100

ggctcgccct acccagggat tcccgtggag gaacttttta agctgctgaa ggaaggacac   2160

agaatggata agccagccaa ctgcaccaac gaactgtaca tgatgatgag ggactgttgg   2220

catgcagtgc cctcccagag accaacgttc aagcagttgg tagaagactt ggatcgaatt   2280

ctcactctca caaccaatga gatggcagat gatcagggct gtattgaaga gcagggggtt   2340

gaggattcag caaatgaaga ttcagtggat gctaagccag accggtcctc gtttgtaccg   2400

tccctcttca gtaagaagaa gaaaaatgtc accatgcgat ccatcaagac cacccgggac   2460

cgagtgccta catatcagta caacatgaat tttgaaaagc tgggcaaatg catcataata   2520

aacaacaaga actttgataa agtgacaggt atgggcgttc gaaacggaac agacaaagat   2580

gccgaggcgc tcttcaagtg cttccgaagc ctgggttttg acgtgattgt ctataatgac   2640

tgctcttgtg ccaagatgca agatctgctt aaaaaagctt ctgaagagga ccatacaaat   2700

gccgcctgct tcgcctgcat cctcttaagc catggagaag aaaatgtaat ttatgggaaa   2760

gatggtgtca caccaataaa ggatttgaca gcccacttta ggggggatag atgcaaaacc   2820

cttttagaga aacccaaact cttcttcatt caggcttgcc gagggaccga gcttgatgat   2880

ggcatccagg ccgactcggg gcccatcaat gacacagatg ctaatcctcg atacaagatc   2940

ccagtggaag ctgacttcct cttcgcctat tccacggttc caggctatta ctcgtggagg   3000

agcccaggaa gaggctcctg gtttgtgcaa gccctctgct ccatcctgga ggagcacgga   3060

aaagacctgg aaatcatgca gatcctcacc agggtgaatg acagagttgc caggcacttt   3120

gagtctcagt ctgatgaccc acacttccat gagaagaagc agatcccctg tgtggtctcc   3180

atgctcacca aggaactcta cttcagtcaa tag                                3213


<210> SEQ ID NO 38
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /organism="Artificial Sequence"
      /note="Description of Artificial Sequence: Synthetic
      oligonucleotide"
      /mol_type="unassigned DNA"

<400> SEQUENCE: 38

tttttttttt tttttttttt tttt                                            24
```

FGFR TYROSINE KINASE INHIBITORS FOR THE TREATMENT OF UROTHELIAL CARCINOMA

CROSS-REFERENCE TO RELATED APPLICATIONS

This application is the National Stage of International Patent Application No. PCT/US2020/025166, filed Mar. 27, 2020, which claims priority to European Patent Application No. 19166428.3, filed Mar. 29, 2019 and European Patent Application No. 19188971.6, filed Jul. 30, 2019. The foregoing applications are incorporated herein by reference in their entireties for any and all purposes.

TECHNICAL FIELD

Disclosed here are methods of treating urothelial carcinoma in a patient comprising evaluating a biological sample from the patient for the presence of at least two fibroblast growth factor receptor (FGFR) genetic alterations and treating the patient with an FGFR inhibitor if the at least two fibroblast growth factor receptor (FGFR) genetic alterations are present in the sample. Also disclosed herein are methods of treating urothelial carcinoma in a patient harboring at least two fibroblast growth factor receptor (FGFR) genetic alterations comprising administering a FGFR inhibitor.

BACKGROUND

The identification of genetic abnormalities can be useful in selecting the appropriate therapeutic(s) for cancer patients. This is also useful for cancer patients failing the main therapeutic option (front-line therapy) for that cancer type, particularly if there is no accepted standard of care for second and subsequent-line therapy. Fibroblast growth factor receptors (FGFRs) are a family of receptor tyrosine kinases involved in regulating cell survival, proliferation, migration and differentiation. FGFR alterations including FGFR mutations and FGFR fusions or translocations have been observed in some cancers.

To date, there are no approved therapies with an FGFR inhibitor that are efficacious in patients with FGFR alterations.

SUMMARY

Described here are methods of treating urothelial carcinoma in a patient comprising, consisting of, or consisting essentially of (a) evaluating a biological sample from the patient for the presence of at least two FGFR genetic alterations, wherein: (i) two or more of the at least two FGFR genetic alterations are FGFR2 fusions; (ii) one or more of the at least two FGFR genetic alterations is an FGFR2 fusion and one or more of the at least two FGFR genetic alterations is an FGFR3 fusion; (iii) two or more of the at least two FGFR genetic alterations are FGFR3 mutations; (iv) one or more of the at least two FGFR genetic alterations is an FGFR3 mutation and one or more of the at least two FGFR genetic alterations is an FGFR2 fusion; or (v) one or more of the at least two FGFR genetic alterations is an FGFR3 mutation and one or more of the at least two FGFR genetic alterations is an FGFR3 fusion; and (b) treating the patient with an FGFR inhibitor if the at least two FGFR genetic alterations are present in the sample. Also described herein are methods of treating urothelial carcinoma in a patient harboring at least two FGFR genetic alterations comprising, consisting of, or consisting essentially of administering a FGFR inhibitor to the patient, wherein: (a) two or more of the at least two FGFR genetic alterations are FGFR2 fusions; (b) one or more of the at least two FGFR genetic alterations is an FGFR2 fusion and one or more of the at least two FGFR genetic alterations is an FGFR3 fusion; (c) two or more of the at least two FGFR genetic alterations are FGFR3 mutations; (d) one or more of the at least two FGFR genetic alterations is an FGFR3 mutation and one or more of the at least two FGFR genetic alterations is an FGFR2 fusion; or (e) one or more of the at least two FGFR genetic alterations is an FGFR3 mutation and one or more of the at least two FGFR genetic alterations is an FGFR3 fusion. In certain embodiments, the methods of treating urothelial carcinoma in a patient harboring at least two FGFR genetic alterations further comprise evaluating a biological sample from the patient for the presence of the at least two FGFR genetic alterations prior to administration of the FGFR inhibitor.

In certain embodiments of the methods of treating urothelial carcinoma disclosed herein, two or more of the at least two FGFR genetic alterations are FGFR2 fusions. In some embodiments, two or more FGFR genetic alterations comprise FGFR2-BICC1 and FGFR2-CASP7.

In certain embodiments of the methods of treating urothelial carcinoma disclosed herein, one or more of the at least two FGFR genetic alterations is an FGFR2 fusion and one or more of the at least two FGFR genetic alterations is an FGFR3 fusion. In some embodiments, two or more FGFR genetic alterations comprise FGFR2-CASP7 and FGFR3-BAIAP2L1; FGFR2-CASP7 and FGFR3-TACC3 V1; or FGFR2-CASP7 and FGFR3-TACC3 V3.

In certain embodiments of the methods of treating urothelial carcinoma disclosed herein, two or more of the at least two FGFR genetic alterations are FGFR3 mutations. In some embodiments, two or more FGFR genetic alterations comprise FGFR3 G370C and FGFR3 S249C; FGFR3 R248C and FGFR3 Y373C; or FGFR3 S249C and FGFR3 Y373C.

In certain embodiments of the methods of treating urothelial carcinoma disclosed herein, one or more of the at least two FGFR genetic alterations is an FGFR3 mutation and one or more of the at least two FGFR genetic alterations is an FGFR2 fusion. In some embodiments, two or more FGFR genetic alterations comprise FGFR3 G370C/FGFR2-BICC1; or FGFR3 S249C, FGFR3 Y373C, FGFR2-CASP7, FGFR3-BAIAP2L1, FGFR3-TACC3 V1 and FGFR3_TACC3 V3.

In certain embodiments of the methods of treating urothelial carcinoma disclosed herein, one or more of the at least two FGFR genetic alterations is an FGFR3 mutation and one or more of the at least two FGFR genetic alterations is an FGFR3 fusion. In some embodiments, the two or more FGFR genetic alterations are FGFR3 G370C and FGFR3-TACC3 V1; FGFR3 R248C and FGFR3-TACC3 V1; FGFR3 S249C and FGFR3-BAIAP2L1; FGFR3 R248C, FGFR3 S249 and FGFR3-TACC3 V1; or FGFR3 S249C, FGFR3 Y373C, FGFR2-CASP7, FGFR3-BAIAP2L1, FGFR3-TACC3 V1 and FGFR3-TACC3 V3.

In certain embodiments of the methods of treating urothelial carcinoma disclosed herein, the urothelial carcinoma is locally advanced or metastatic.

In further embodiments of the methods of treating urothelial carcinoma disclosed herein, the biological sample is blood, lymph fluid, bone marrow, a solid tumor sample, or any combination thereof.

In some embodiments, the FGFR inhibitor is erdafitinib. In further embodiments, erdafitinib is administered daily, in particular once daily. In still further embodiments, erdafitinib is administered orally. In certain embodiments, erdafitinib is administered orally on a continuous daily dosing schedule. In some embodiments, erdafitinib is administered orally at a dose of about 8 mg once daily. In some embodiments, erdafitinib is administered orally at a dose of about 8 mg once daily on a continuous daily dosing schedule. In further embodiments, the dose of erdafitinib is increased from 8 mg once daily to 9 mg once daily at 14 to 21 days after initiating treatment if: (a) the patient exhibits a serum phosphate ($PO_4$) level that is less than about 5.5 mg/dL at 14-21 days after initiating treatment; and (b) administration of erdafitinib at 8 mg once daily resulted in no ocular disorder or (c) administration of erdafitinib at 8 mg once daily resulted in no Grade 2 or greater adverse reaction.

In certain embodiments of the methods of treating urothelial carcinoma disclosed herein, erdafitinib is present in a solid dosage form. In some embodiments, the solid dosage form is a tablet.

BRIEF DESCRIPTION OF THE DRAWINGS

The summary, as well as the following detailed description, is further understood when read in conjunction with the appended drawings. For the purpose of illustrating the disclosed methods, the drawings show exemplary embodiments of the methods; however, the methods are not limited to the specific embodiments disclosed. In the drawings:

FIG. 3, which comprises

FIG. 6, which comprises

DETAILED DESCRIPTION OF ILLUSTRATIVE EMBODIMENTS

Figure 1:
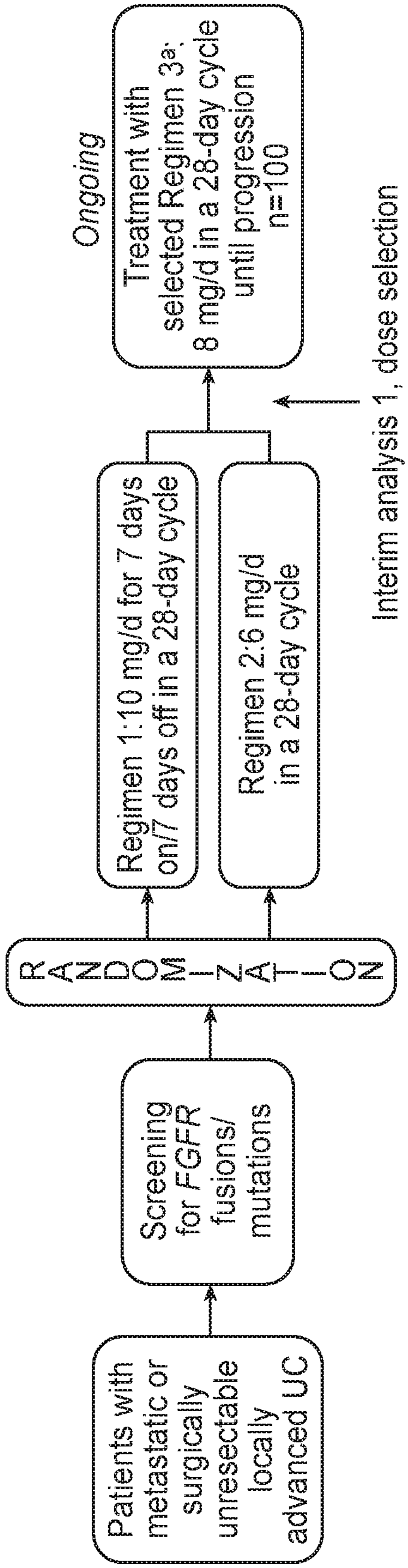
FIG. 1 represents the study scheme for the Phase 2, multicenter, open-label study to evaluate the efficacy and safety of erdafitinib in subjects with metastatic or surgically unresectable urothelial cancer harboring selected FGFR (fibroblast growth factor receptor) genetic alterations (FGFR translocations or mutations).

It is to be appreciated that certain features of the invention which are, for clarity, described herein in the context of separate embodiments may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, although an embodiment may be described as part of a series of steps or part of a more general structure, each said step may also be considered an independent embodiment in itself, combinable with others.

Certain Terminology

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of excludes any element, step, or ingredient not specified in the claim; and (iii) "consisting essentially of limits the scope of a claim to the specified materials or steps "and those that do not materially affect the basic and novel characteristic(s)" of the claimed invention. More specifically, the basic and novel characteristics relates to the ability of the method to provide at least one of the benefits described herein, including but not limited to the ability to improve the survivability of the human population relative to the survivability of the comparative human population described elsewhere herein. Embodiments described in terms of the phrase "comprising" (or its equivalents), also provide, as embodiments, those which are independently described in terms of "consisting of and "consisting essentially of."

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

If not otherwise specified, the term "about" signifies a variance of 10% of the associated value, but additional embodiments include those where the variance may be ±5%, ±15%, ±20%, ±25%, or ±50%.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." As used herein, the singular forms "a," "an," and "the" include the plural.

The following abbreviations are used throughout the disclosure: FGFR (fibroblast growth factor receptor); FGFR3-TACC3 v1 (fusion between genes encoding FGFR3 and transforming acidic coiled-coil containing protein 3 variant 1, also referred to herein as FGFR3-TACC3 V1); FGFR3-TACC3 v3 (fusion between genes encoding FGFR3 and transforming acidic coiled-coil containing protein 3 variant 3, also referred to herein as FGFR3-TACC3_V2); FGFR3-BAIAP2L1 (fusion between genes encoding FGFR3 and brain-specific angiogenesis inhibitor 1-associated protein 2-like protein 1); FGFR2-BICC1 (fusion between genes encoding FGFR2 and bicaudal C homolog 1); FGFR2-CASP7 (fusion between genes encoding FGFR2 and caspase 7).

As used herein, "patient" is intended to mean any animal, in particular, mammals. Thus, the methods are applicable to human and nonhuman animals, although most preferably with humans. The terms "patient" and "subject" and "human" may be used interchangeably.

The terms "treat" and "treatment" refer to the treatment of a patient afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "cancer" as used herein refers to an abnormal growth of cells which tend to proliferate in an uncontrolled way and, in some cases, to metastasize (spread).

The terms "co-administration" or the like, as used herein, encompass administration of the selected therapeutic agents to a single patient, and are intended to include treatment regimens in which the agents are administered by the same or different route of administration or at the same or different time.

The term "pharmaceutical combination" as used herein, means a product that results from the mixing or combining of more than one active ingredient and includes both fixed and non-fixed combinations of the active ingredients. The term "fixed combination" means that the active ingredients, e.g., erdafitinib and a co-agent, are both administered to a patient simultaneously in the form of a single unit or single dosage form. The term "non-fixed combination" means that the active ingredients, e.g., erdafitinib and a co-agent, are administered to a patient as separate units or separate dosage forms, either simultaneously, concurrently or sequentially with no specific intervening time limits, wherein such administration provides safe and effective levels of the two active ingredients in the body of the human patient. The latter also applies to cocktail therapy, e.g., the administration of three or more active ingredients.

The term "continuous daily dosing schedule" refers to the administration of a particular therapeutic agent without any drug holidays from the particular therapeutic agent. In some embodiments, a continuous daily dosing schedule of a particular therapeutic agent comprises administration of a particular therapeutic agent every day at roughly the same time each day.

The term "progression-free survival" is defined as the time from first dose to date of documented evidence of disease progression or death, whichever comes first.

The term "duration of response" is defined as the time from initial documentation of response to the date of documented evidence of disease progression or death.

The term "overall survival" is defined as the time from first dose to the date of death. Data for patients who are alive or have unknown status is censored at the last date on which the patient is known to be alive.

The term "placebo" as used herein means administration of a pharmaceutical composition that does not include an FGFR inhibitor.

The term "randomization" as it refers to a clinical trial refers to the time when the patient is confirmed eligible for the clinical trial and gets assigned to a treatment arm.

The terms "kit" and "article of manufacture" are used as synonyms.

"Biological samples" refers to any sample for a patient in which cancerous cells can be obtained and detection of a FGFR genetic alteration is possible. Suitable biological samples include, but are not limited to, blood, lymph fluid, bone marrow, a solid tumor sample, or any combination thereof. In some embodiments, the biological sample can be formalin-fixed paraffin-embedded tissue (FFPET).

FGFR Genetic Alterations

Described here are methods of treating urothelial carcinoma in a patient comprising, consisting of, or consisting essentially of: (a) evaluating a biological sample from the patient for the presence of at least two FGFR genetic alterations, wherein: (i) two or more of the at least two FGFR genetic alterations are FGFR2 fusions; (ii) one or more of the at least two FGFR genetic alterations is an FGFR2 fusion and one or more of the at least two FGFR genetic alterations is an FGFR3 fusion; (iii) two or more of the at least two FGFR genetic alterations are FGFR3 mutations; (iv) one or more of the at least two FGFR genetic alterations is an FGFR3 mutation and one or more of the at least two FGFR genetic alterations is an FGFR2 fusion; or (v) one or more of the at least two FGFR genetic alterations is an FGFR3 mutation and one or more of the at least two FGFR genetic alterations is an FGFR3 fusion; and (b) treating the patient with an FGFR inhibitor if the at least two FGFR genetic alterations are present in the sample.

Also described herein are methods of treating urothelial carcinoma in a patient harboring at least two FGFR genetic alterations comprising, consisting of, or consisting essentially of administering a FGFR inhibitor to the patient, wherein: (a) two or more of the at least two FGFR genetic alterations are FGFR2 fusions; (b) one or more of the at least two FGFR genetic alterations is an FGFR2 fusion and one or more of the at least two FGFR genetic alterations is an FGFR3 fusion; (c) two or more of the at least two FGFR genetic alterations are FGFR3 mutations; (d) one or more of the at least two FGFR genetic alterations is an FGFR3 mutation and one or more of the at least two FGFR genetic alterations is an FGFR2 fusion; or (e) one or more of the at least two FGFR genetic alterations is an FGFR3 mutation and one or more of the at least two FGFR genetic alterations is an FGFR3 fusion.

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signaling molecules which act as autocrine as well as paracrine factors. Autocrine FGF signaling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Knights et al., *Pharmacology and Therapeutics* 2010 125:1 (105-117); Korc M. et al *Current Cancer Drug Targets* 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

In certain embodiments, the urothelial carcinoma is susceptible to an FGFR2 genetic alteration or an FGFR3 genetic alteration. In further embodiments, the urothelial carcinoma is susceptible to at least two FGFR genetic alterations. In certain embodiments, the urothelial carcinoma is susceptible to at least two FGFR genetic alterations wherein: (i) two or more of the at least two FGFR genetic alterations are FGFR2 fusions; (ii) one or more of the at least two FGFR genetic alterations is an FGFR2 fusion and one or more of the at least two FGFR genetic alterations is an FGFR3 fusion; (iii) two or more of the at least two FGFR genetic alterations are FGFR3 mutations; (iv) one or more of the at least two FGFR genetic alterations is an FGFR3 mutation and one or more of the at least two FGFR genetic alterations is an FGFR2 fusion; or (v) one or more of the at least two FGFR genetic alterations is an FGFR3 mutation and one or more of the at least two FGFR genetic alterations is an FGFR3 fusion As used herein, "FGFR genetic alteration" refers to an alteration in the wild type FGFR gene, including, but not limited to, FGFR fusion genes, FGFR mutations, FGFR amplifications, or any combination thereof. The terms "variant" and "alteration" are used interchangeably herein.

In certain embodiments, the FGFR genetic alteration is an FGFR gene fusion. "FGFR fusion" or "FGFR gene fusion" refers to a gene encoding a portion of FGFR (e.g., FGRF2 or FGFR3) and one of the herein disclosed fusion partners, or a portion thereof, created by a translocation between the two genes. The terms "fusion" and "translocation" are used interchangeable herein. The presence of one or more of the following FGFR fusion genes in a biological sample from a patient can be determined using the disclosed methods: FGFR3-TACC3, FGFR3-BAIAP2L1, FGFR2-BICC1, FGFR2-CASP7, or any combination thereof. In certain embodiments, FGFR-TACC3 is FGFR-TACC3 variant 1 (FGFR-TACC3 v1) or FGFR-TACC3 variant 3 (FGFR-TACC3 v3). Table 1 provides the FGFR fusion genes and the FGFR and fusion partner exons that are fused. The sequences of the individual FGFR fusion genes are disclosed in Table 1.

TABLE 1

| Fusion Gene | FGFR Exon | Partner Exon |
|---|---|---|
| FGFR2 | | |
| FGFR2-BICC1 | 19 | 3 |
| FGFR2-CASP7 | 19 | 4 |
| FGFR3 | | |
| FGFR3-BAIAP2L1 | 18 | 2 |
| FGFR3-TACC3 v1 | 18 | 11 |
| FGFR3-TACC3 v3 | 18 | 10 |

FGFR genetic alterations include FGFR single nucleotide polymorphism (SNP). "FGFR single nucleotide polymorphism" (SNP) refers to a FGFR2 or FGFR3 gene in which a single nucleotide differs among individuals. In certain embodiments, the FGFR2 or FGFR3 genetic alteration is an FGFR3 gene mutation. In particular, FGFR single nucleotide polymorphism" (SNP) refers to a FGFR3 gene in which a single nucleotide differs among individuals. The presence of one or more of the following FGFR SNPs in a biological sample from a patient can be determined by methods known to those of ordinary skill in the art or methods disclosed in WO 2016/048833, FGFR3 R248C, FGFR3 S249C, FGFR3 G370C, FGFR3 Y373C, or any combination thereof. The sequences of the FGFR SNPs are provided in Table 2.

TABLE 2

| FGFR3 mutant | Sequence |
|---|---|
| FGFR3 R248C | TCGGACCGCGGCAACTACACCTGCGTCGTGGAGAACAAGTTTGGCA<br>GCATCCGGCAGACGTACACGCTGGACGTGCTGGAG(**T**)GCTCCCCGC<br>ACCGGCCCATCCTGCAGGCGGGGCTGCCGGCCAACCAGACGGCGGT<br>GCTGGGCAGCGACGTGGAGTTCCACTGCAAGGTGTACAGTGACGCA<br>CAGCCCCACATCCAGTGGCTCAAGCACGTGGAGGTGAATGGCAGCA<br>AGGTGGGCCCGGACGGCACACCCTACGTTACCGTGCTCA<br>(SEQ ID NO: 1) |
| FGFR3 S249C | GACCGCGGCAACTACACCTGCGTCGTGGAGAACAAGTTTGGCAGCA<br>TCCGGCAGACGTACACGCTGGACGTGCTGGGTGAGGGCCCTGGGGC<br>GGCGCGGGGGTGGGGGCGGCAGTGGCGGTGGTGGTGAGGGAGGGG<br>GTGGCCCCTGAGCGTCATCTGCCCCCACAGAGCGCT(**G**)CCCGCACC<br>GGCCCATCCTGCAGGCGGGGCTGCCGGCCAACCAGACGGCGGTGCT<br>GGGCAGCGACGTGGAGTTCCACTGCAAGGTGTACAGTGACGCACAG<br>CCCCACATCCAGTGGCTCAAGCACGTGGAGGTGAATGGCAGCAAGG<br>TGGGCCCGGACGGCACACCCTACGTTACCGTGCTCAAGGTGGGCCA<br>CCGTGTGCACGT<br>(SEQ ID NO: 2) |
| FGFR3 G370C | GCGGGCAATTCTATTGGGTTTTCTCATCACTCTGCGTGGCTGGTGGT<br>GCTGCCAGCCGAGGAGGAGCTGGTGGAGGCTGACGAGGCG(**T**)GCA<br>GTGTGTATGCAGGCATCCTCAGCTACGGGGTGGGCTTCTTCCTGTTC<br>ATCCTGGTGGTGGCGGCTGTGACGCTCTGCCGCCTGCGCAGCCCCCC<br>CAAGAAAGGCCTGGGCTCCCCCACCGTGCACAAGATCTCCCGCTTC<br>CCG<br>(SEQ ID NO: 3) |

TABLE 2-continued

| FGFR3 mutant | Sequence |
|---|---|
| FGFR3 Y373C* | CTAGAGGTTCTCTCCTTGCACAACGTCACCTTTGAGGACGCCGGGGA GTACACCTGCCTGGCGGGCAATTCTATTGGGTTTTCTCATCACTCTG CGTGGCTGGTGGTGCTGCCAGCCGAGGAGGAGCTGGTGGAGGCTGA CGAGGCGGGCAGTGTGT(**G**)TGCAGGCATCCTCAGCTACGGGGTGGG CTTCTTCCTGTTCATCCTGGTGGTGGCGGCTGTGACGCTCTGCCGCC TGCGCAGCCCCCCCAAGAAAGGCCTGGGCTCCCCCACCGTGCACAA GATCTCCCGCTTCCCGCTCAAGC (SEQ ID NO: 4) |

Sequences correspond to nucleotides 920-1510 of FGFR3 (Genebank ID # NM_000142.4).

Nucleotides in bold underline represent the SNP.

*Sometimes mistakenly referred to as Y375C in the literature.

In certain embodiments, the urothelial carcinoma is susceptible to at least two FGFR genetic alterations. In some embodiments, the FGFR alterations can be one or more FGFR fusion genes. In some embodiments, the FGFR alterations can be one or more FGFR mutations. In some embodiments, the FGFR alterations can be one or more FGFR amplifications. In some embodiments, a combination of the one or more FGFR alterations can be present in the biological sample from the patient.

In some embodiments, one or more of the at least two FGFR genetic alterations is an FGFR mutation. In further embodiments, one or more of the at least two FGFR genetic alterations is an FGFR2 mutation. In still further embodiments, one or more of the at least two FGFR genetic alterations is an FGFR3 mutation. In some embodiments, the FGFR3 mutation is FGFR3 R248C, FGFR3 S249C, FGFR3 G370C, FGFR3 Y373C, or any combination thereof.

In some embodiments, one or more of the at least two FGFR genetic alterations is an FGFR fusion. In further embodiments, one or more of the at least two FGFR genetic alterations is an FGFR3 fusion. In still further embodiments, the FGFR3 fusion is FGFR3-BAIAP2L1, FGFR3-TACC3 v1, FCFR3-TACC3 v3, or any combination thereof. In further embodiments, one or more of the at least two FGFR genetic alterations is an FGFR2 fusion. In still further embodiments, the FGFR2 fusion is FGFR2-BICC1, FGFR2-CASP7, or any combination thereof.

In certain embodiments, two or more of the at least two FGFR genetic alterations are FGFR2 fusions. In some embodiments, two or more FGFR genetic alterations comprise FGFR2-BICC1 and FGFR2-CASP7.

In certain embodiments, one or more of the at least two FGFR genetic alterations is an FGFR2 fusion and one or more of the at least two FGFR genetic alterations is an FGFR3 fusion. In some embodiments, two or more FGFR genetic alterations comprise FGFR2-CASP7 and FGFR3-BAIAP2L1; FGFR2-CASP7 and FGFR3-TACC3 V1; or FGFR2-CASP7 and FGFR3-TACC3 V3.

In certain embodiments, two or more of the at least two FGFR genetic alterations are FGFR3 mutations. In some embodiments, two or more FGFR genetic alterations comprise FGFR3 G370C and FGFR3 S249C; FGFR3 R248C and FGFR3 Y373C; or FGFR3 S249C and FGFR3 Y373C.

In certain embodiments, one or more of the at least two FGFR genetic alterations is an FGFR3 mutation and one or more of the at least two FGFR genetic alterations is an FGFR2 fusion. In some embodiments, two or more FGFR genetic alterations comprise FGFR3 G370C/FGFR2-BICC1; or FGFR3 S249C, FGFR3 Y373C, FGFR2-CASP7, FGFR3-BAIAP2L1, FGFR3-TACC3 V1 and FGFR3-TACC3 V3.

In certain embodiments, one or more of the at least two FGFR genetic alterations is an FGFR3 mutation and one or more of the at least two FGFR genetic alterations is an FGFR3 fusion. In some embodiments, two or more FGFR genetic alterations comprise FGFR3 G370C and FGFR3-TACC3 V1; FGFR3 R248C and FGFR3-TACC3 V1; FGFR3 S249C and FGFR3-BAIAP2L1; FGFR3 R248C, FGFR3 S249 and FGFR3-TACC3 V1; or FGFR3 S249C, FGFR3 Y373C, FGFR2-CASP7, FGFR3-BAIAP2L1, FGFR3-TACC3 V1 and FGFR3-TACC3 V3.

As used herein, "FGFR mutant gene panel" includes one or more of the above listed FGFR mutants. In some embodiments, the FGFR mutant gene panel is dependent upon the patient's cancer type.

The FGFR mutant panel that is used in the evaluating step of the disclosed methods is based, in part, on the patient's cancer type. For patients with urothelial carcinoma, a suitable FGFR mutant gene panel can comprise FGFR3-TACC3_V1, FGFR3-TACC3 V3, FGFR3-BAIAP2L1, FGFR2-BICC1, FGFR2-CASP7, FGFR3 R248C, FGFR3 S249C, FGFR3 G370C, or FGFR3 Y373C, or any combination thereof.

FGFR inhibitors for use in the disclosed methods or uses Suitable FGFR inhibitors for use in the disclosed methods are provided herein.

In some embodiments, if one or more FGFR mutants are present in the sample, the urothelial carcinoma patient can be treated with a FGFR inhibitor disclosed in U.S. Publication No. 2013/0072457 A1 (incorporated herein by reference), including any tautomeric or stereochemically isomeric form thereof, and a N-oxide thereof, a pharmaceutically acceptable salt thereof, or a solvate thereof (suitable R groups are also disclosed in U.S. Publication No. 2013/0072457 A1).

In some aspects, for example, the patient may be treated with N-(3,5-dimethoxy-phenyl)-N'-(1-methylethyl)-N-[3-(1-methyl-1H-pyrazol-4-yl)quinoxalin-6-yl]ethane-1,2-diamine (referred to herein "JNJ-42756493" or "JNJ493" or erdafitinib), including any tautomeric form thereof, N-oxides thereof, pharmaceutically acceptable salts thereof, or solvates thereof. In some embodiments, the FGFR inhibitor can be the compound of formula (I):

(I)

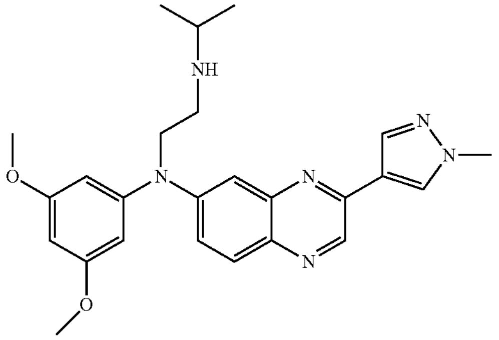

or a pharmaceutically acceptable salt thereof. In some aspects, the pharmaceutically acceptable salt is a HCl salt. In preferred aspects, erdafitinib base is used.

In some embodiments, the urothelial carcinoma patient can be treated with a FGFR inhibitor wherein the FGFR inhibitor is N-[5-[2-(3,5-Dimethoxyphenyl)ethyl]-2H-pyrazol-3-yl]-4-(3,5-diemthylpiperazin-1-yl)benzamide (AZD4547), as described in Gavine, P. R., et al., AZD4547: An Orally Bioavailable, Potent, and Selective Inhibitor of the Fibroblast Growth Factor Receptor Tyrosine Kinase Family, Cancer Res. Apr. 15, 2012 72; 2045:

(II)

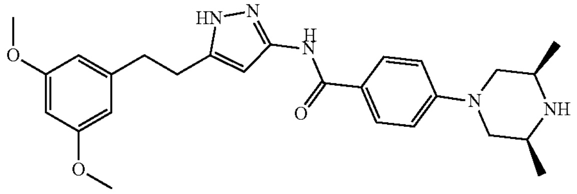

including, when chemically possible, any tautomeric or stereochemically isomeric form thereof, and a N-oxide thereof, a pharmaceutically acceptable salt thereof, or a solvate thereof In some embodiments, the urothelial carcinoma patient can be treated with a FGFR inhibitor wherein the FGFR inhibitor is 3-(2,6-Dichloro-3,5-dimethoxy-phenyl)-1-{6-[4-(4-ethyl-piperazin-1-yl)-phenylamino]-pyrimid-4-yl}-methyl-urea (NVP-BGJ398) as described in Int'l Publ. No. WO2006/000420:

(III)

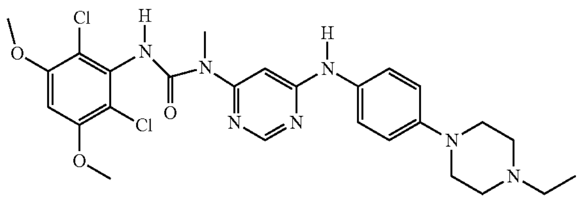

including, when chemically possible, any tautomeric or stereochemically isomeric form thereof, and a N-oxide thereof, a pharmaceutically acceptable salt thereof, or a solvate thereof.

In some embodiments, the urothelial carcinoma patient can be treated with a FGFR inhibitor wherein the FGFR inhibitor is 4-amino-5-fluoro-3-[6-(4-methylpiperazin-1-yl)-lH-benzimidazol-2-yl]-lH-quinolin-2-one (dovitinib) as described in Int't Publ. No.

(IV)

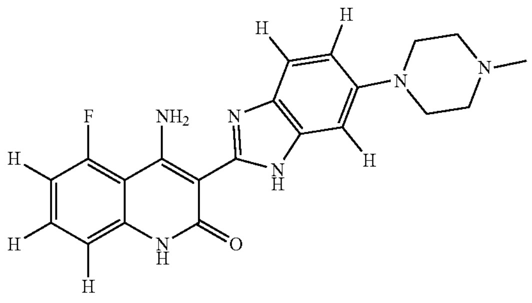

including, when chemically possible, any tautomeric or stereochemically isomeric form thereof, and a N-oxide thereof, a pharmaceutically acceptable salt thereof, or a solvate thereof.

In some embodiments, the urothelial carcinoma patient can be treated with a FGFR inhibitor wherein the FGFR inhibitor is 6-(7-((1-Aminocyclopropyl)-methoxy)-6-methoxyquinolin-4-yloxy)-N-methyl-1-naphthamide (AL3810) (lucitanib; E-3810), as described in Bello, E. et al., E-3810 Is a Potent Dual Inhibitor of VEGFR and FGFR that Exerts Antitumor Activity in Multiple Preclinical Models, Cancer Res Feb. 15, 2011 71(A)1396-1405 and Int'l Publ. No. WO2008/112408:

(V)

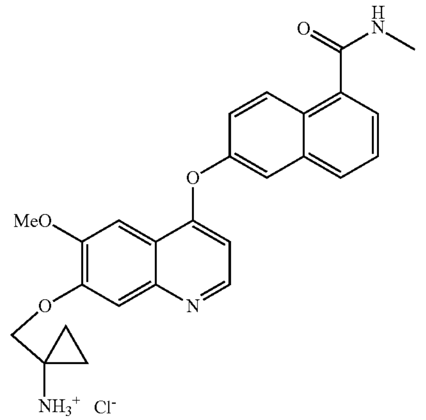

including, when chemically possible, any tautomeric or stereochemically isomeric form thereof, and a N-oxide thereof, a pharmaceutically acceptable salt thereof, or a solvate thereof.

Additional suitable FGFR inhibitors include BAY1163877 (Bayer), BAY1179470 (Bayer), TAS-120 (Taiho), ARQ087 (ArQule), ASP5878 (Astellas), FF284 (Chugai), FP-1039 (GSK/FivePrime), Blueprint, LY-2874455 (Lilly), RG-7444 (Roche), or any combination thereof, including, when chemically possible, any tautomeric or stereochemical isomeric forms thereof, N-oxides thereof, pharmaceutically acceptable salts thereof, or solvates thereof.

In an embodiment the FGFR inhibitor generally, and erdafitinib more specifically, is administered as a pharmaceutically acceptable salt. In a preferred embodiment the FGFR inhibitor generally, is administered in base form. In an embodiment the FGFR inhibitor generally, and erdafitinib more specifically, is administered as a pharmaceutically acceptable salt in an amount corresponding to 8 mg base equivalent or corresponding to 9 mg base equivalent. In an embodiment the FGFR inhibitor generally, and erdafitinib more specifically, is administered in base form in an amount of 8 mg or 9 mg.

The salts can be prepared by for instance reacting the FGFR inhibitor generally, and erdafitinib more specifically, with an appropriate acid in an appropriate solvent.

Acid addition salts may be formed with acids, both inorganic and organic. Examples of acid addition salts include salts formed with an acid selected from the group consisting of acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

In an embodiment, the FGFR inhibitor generally, and erdafitinib more specifically, is administered in the form of a solvate. As used herein, the term "solvate" means a physical association of erdafitinib with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. The term "solvate" is intended to encompass both solution-phase and isolatable solvates. Non-limiting examples of solvents that may form solvates include water, isopropanol, ethanol, methanol, DMSO, ethyl acetate, acetic acid or ethanolamine and the like.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid-State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallization conditions that include an amount of the solvent required for the particular solvate. Thereafter the standard methods described above, can be used to establish whether solvates had formed. Also encompassed are any complexes (e.g. inclusion complexes or clathrates with compounds such as cyclodextrins, or complexes with metals).

Furthermore, the compound may have one or more polymorph (crystalline) or amorphous forms.

The compounds include compounds with one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. The isotopes may be radioactive or nonradioactive. In one embodiment, the compounds contain no radioactive isotopes. Such compounds are preferred for therapeutic use. In another embodiment, however, the compound may contain one or more radioisotopes. Compounds containing such radioisotopes may be useful in a diagnostic context.

Methods of Treatment/Compounds for Use

Described here are methods of treating urothelial carcinoma in a patient comprising, consisting of, or consisting essentially of: (a) evaluating a biological sample from the patient for the presence of at least two FGFR genetic alterations, wherein: (i) two or more of the at least two FGFR genetic alterations are FGFR2 fusions; (ii) one or more of the at least two FGFR genetic alterations is an FGFR2 fusion and one or more of the at least two FGFR genetic alterations is an FGFR3 fusion; (iii) two or more of the at least two FGFR genetic alterations are FGFR3 mutations; (iv) one or more of the at least two FGFR genetic alterations is an FGFR3 mutation and one or more of the at least two FGFR genetic alterations is an FGFR2 fusion; or (v) one or more of the at least two FGFR genetic alterations is an FGFR3 mutation and one or more of the at least two FGFR genetic alterations is an FGFR3 fusion; and (b) treating the patient with an FGFR inhibitor if the at least two FGFR genetic alterations are present in the sample.

Also described herein are FGFR inhibitors for use in the treatment of urothelial carcinoma, said treatment comprising, consisting of, or consisting essentially of: (a) evaluating a biological sample from the patient for the presence of at least two FGFR genetic alterations, wherein: (i) two or more of the at least two FGFR genetic alterations are FGFR2 fusions; (ii) one or more of the at least two FGFR genetic alterations is an FGFR2 fusion and one or more of the at least two FGFR genetic alterations is an FGFR3 fusion; (iii) two or more of the at least two FGFR genetic alterations are FGFR3 mutations; (iv) one or more of the at least two FGFR genetic alterations is an FGFR3 mutation and one or more of the at least two FGFR genetic alterations is an FGFR2 fusion; or (v) one or more of the at least two FGFR genetic alterations is an FGFR3 mutation and one or more of the at least two FGFR genetic alterations is an FGFR3 fusion; and (b) administering to the patient an FGFR inhibitor if the at least two FGFR genetic alterations are present in the sample.

Also described herein are uses of FGFR inhibitors in the manufacture of a medicament for the treatment of urothelial carcinoma, said treatment comprising, consisting of, or consisting essentially of: (a) evaluating a biological sample from the patient for the presence of at least two FGFR genetic alterations, wherein: (i) two or more of the at least two FGFR genetic alterations are FGFR2 fusions; (ii) one or more of the at least two FGFR genetic alterations is an FGFR2 fusion and one or more of the at least two FGFR genetic alterations is an FGFR3 fusion; (iii) two or more of the at least two FGFR genetic alterations are FGFR3 mutations; (iv) one or more of the at least two FGFR genetic alterations is an FGFR3 mutation and one or more of the at least two FGFR genetic alterations is an FGFR2 fusion; or (v) one or more of the at least two FGFR genetic alterations is an FGFR3 mutation and one or more of the at least two FGFR genetic alterations is an FGFR3 fusion; and (b)

administering to the patient an FGFR inhibitor if the at least two FGFR genetic alterations are present in the sample.

Also described herein are methods of treating urothelial carcinoma in a patient harboring at least two FGFR genetic alterations comprising, consisting of, or consisting essentially of administering a FGFR inhibitor to the patient, wherein: (a) two or more of the at least two FGFR genetic alterations are FGFR2 fusions; (b) one or more of the at least two FGFR genetic alterations is an FGFR2 fusion and one or more of the at least two FGFR genetic alterations is an FGFR3 fusion; (c) two or more of the at least two FGFR genetic alterations are FGFR3 mutations; (d) one or more of the at least two FGFR genetic alterations is an FGFR3 mutation and one or more of the at least two FGFR genetic alterations is an FGFR2 fusion; or (e) one or more of the at least two FGFR genetic alterations is an FGFR3 mutation and one or more of the at least two FGFR genetic alterations is an FGFR3 fusion.

Also described herein are FGFR inhibitors for use in the treatment of urothelial carcinoma in a patient harboring at least two FGFR genetic alterations, said treatment comprising, consisting of, or consisting essentially of administering a FGFR inhibitor to the patient, wherein: (a) two or more of the at least two FGFR genetic alterations are FGFR2 fusions; (b) one or more of the at least two FGFR genetic alterations is an FGFR2 fusion and one or more of the at least two FGFR genetic alterations is an FGFR3 fusion; (c) two or more of the at least two FGFR genetic alterations are FGFR3 mutations; (d) one or more of the at least two FGFR genetic alterations is an FGFR3 mutation and one or more of the at least two FGFR genetic alterations is an FGFR2 fusion; or (e) one or more of the at least two FGFR genetic alterations is an FGFR3 mutation and one or more of the at least two FGFR genetic alterations is an FGFR3 fusion.

Also described herein are uses of an FGFR inhibitors in the manufacture of a medicament for the treatment of urothelial carcinoma in a patient harboring at least two FGFR genetic alterations, said treatment comprising, consisting of, or consisting essentially of administering a FGFR inhibitor to the patient, wherein: (a) two or more of the at least two FGFR genetic alterations are FGFR2 fusions; (b) one or more of the at least two FGFR genetic alterations is an FGFR2 fusion and one or more of the at least two FGFR genetic alterations is an FGFR3 fusion; (c) two or more of the at least two FGFR genetic alterations are FGFR3 mutations; (d) one or more of the at least two FGFR genetic alterations is an FGFR3 mutation and one or more of the at least two FGFR genetic alterations is an FGFR2 fusion; or (e) one or more of the at least two FGFR genetic alterations is an FGFR3 mutation and one or more of the at least two FGFR genetic alterations is an FGFR3 fusion.

In certain embodiments, the urothelial carcinoma is locally advanced or metastatic. In certain embodiments, the patient is a high-risk patient, in particular a high-risk patient with metastatic or surgically unresectable urothelial cancer, in particular metastatic or surgically unresectable urothelial cancer harboring select FGFR genetic alterations (FGFR translocations or mutations), in particular FGFR genetic alterations as defined herein. A high-risk patient is a patient meeting one or more of the following criteria: age ≥75 years; ECOG PS 2; hemoglobin <10 g/dL; visceral metastases, in particular of the liver, lung and/or bone; and 2 or 3 Bellmunt risk factors. In an embodiment the hemoglobin level is measured in whole blood.

In certain embodiments, administration of the FGFR inhibitor provides improved anti-tumor activity as measured by objective response rate, progression-free survival, duration of response, or overall survival relative to a patient with urothelial carcinoma that is not receiving treatment with an FGFR inhibitor. In certain embodiments, administration of the FGFR inhibitor provides improved anti-tumor activity as measured by objective response rate or duration of response relative to a patient with urothelial carcinoma that is not receiving treatment with an FGFR inhibitor. In certain embodiments, administration of the FGFR inhibitor provides improved anti-tumor activity as measured by objective response rate relative to a patient with urothelial carcinoma that is not receiving treatment with an FGFR inhibitor. In certain embodiments, administration of the FGFR inhibitor provides improved anti-tumor activity as measured by progression-free survival relative to a patient with urothelial carcinoma that is not receiving treatment with an FGFR inhibitor. In certain embodiments, administration of the FGFR inhibitor provides improved anti-tumor activity as measured by duration of response relative to a patient with urothelial carcinoma that is not receiving treatment with an FGFR inhibitor. In certain embodiments, administration of the FGFR inhibitor provides improved anti-tumor activity as measured by overall survival relative to a patient with urothelial carcinoma that is not receiving treatment with an FGFR inhibitor.

In certain embodiments, the improvement in anti-tumor activity is relative to treatment with placebo. In certain embodiments, the improvement in anti-tumor activity is relative to no treatment. In certain embodiments, the improvement in anti-tumor activity is relative to standard of care.

To assess objective response rate or future progression, it is necessary to estimate the overall tumor burden at baseline and use this as a comparator for subsequent measurements. Measurable disease is defined by the presence of at least one measurable lesion.

In some embodiments, administration of the FGFR inhibitor results in no more than a grade 2 adverse event. In other embodiments, administration of the FGFR inhibitor results in no more than a grade 3 adverse event. In some embodiments, administration of the FGFR inhibitor results in no more than a grade 4 adverse event.

In certain embodiments, the methods of treating urothelial carcinoma or the use in the treatment of urothelial carcinoma in a patient harboring at least two FGFR genetic alterations further comprise evaluating a biological sample from the patient for the presence of the at least two FGFR genetic alterations prior to administration of the FGFR inhibitor.

In certain embodiments of the methods of treating urothelial carcinoma or the use in the treatment of urothelial carcinoma as disclosed herein, two or more of the at least two FGFR genetic alterations are FGFR2 fusions. In some embodiments, two or more FGFR genetic alterations comprise FGFR2-BICC1 and FGFR2-CASP7.

In certain embodiments of the methods of treating urothelial carcinoma or the use in the treatment of urothelial carcinoma as disclosed herein, one or more of the at least two FGFR genetic alterations is an FGFR2 fusion and one or more of the at least two FGFR genetic alterations is an FGFR3 fusion. In some embodiments, two or more FGFR genetic alterations comprise FGFR2-CASP7 and FGFR3-BAIAP2L1; FGFR2-CASP7 and FGFR3-TACC3 V1; or FGFR2-CASP7 and FGFR3-TACC3 V3.

In certain embodiments of the methods of treating urothelial carcinoma or the use in the treatment of urothelial carcinoma as disclosed herein, two or more of the at least two FGFR genetic alterations are FGFR3 mutations. In some embodiments, two or more FGFR genetic alterations comprise FGFR3 G370C and FGFR3 S249C; FGFR3 R248C and FGFR3 Y373C; or FGFR3 S249C and FGFR3 Y373C.

In certain embodiments of the methods of treating urothelial carcinoma or the use in the treatment of urothelial carcinoma as disclosed herein, one or more of the at least two FGFR genetic alterations is an FGFR3 mutation and one or more of the at least two FGFR genetic alterations is an FGFR2 fusion. In some embodiments, two or more FGFR genetic alterations comprise FGFR3 G370C/FGFR2-BICC1; or FGFR3 S249C, FGFR3 Y373C, FGFR2-CASP7, FGFR3-BAIAP2L1, FGFR3-TACC3 V1 and FGFR3_TACC3 V3.

In certain embodiments of the methods of treating urothelial carcinoma or the use in the treatment of urothelial carcinoma as disclosed herein, one or more of the at least two FGFR genetic alterations is an FGFR3 mutation and one or more of the at least two FGFR genetic alterations is an FGFR3 fusion. In some embodiments, two or more FGFR genetic alterations comprise FGFR3 G370C and FGFR3-TACC3 V1; FGFR3 R248C and FGFR3-TACC3 V1; FGFR3 S249C and FGFR3-BAIAP2L1; FGFR3 R248C, FGFR3 S249 and FGFR3-TACC3 V1; or FGFR3 S249C, FGFR3 Y373C, FGFR2-CASP7, FGFR3-BAIAP2L1, FGFR3-TACC3 V1 and FGFR3-TACC3 V3.

In certain embodiments of the methods of treating urothelial carcinoma or the use in the treatment of urothelial carcinoma as disclosed herein, the at least two FGFR genetic alterations comprise FGFR3 G370C and FGFR3 S249C; or FGFR3 R248C and FGFR3 Y373C.

In certain embodiments of the methods of treating urothelial carcinoma or the use in the treatment of urothelial carcinoma as disclosed herein, the at least two FGFR genetic alterations comprise FGFR3 G370C and FGFR2-BICC1; FGFR3 G370C and FGFR3-TACC3 V1; FGFR3 R248C and FGFR3-TACC3 V1; or FGFR3 R248C, FGFR3 S249 and FGFR3-TACC3 V1.

In certain embodiments of the methods of treating urothelial carcinoma or the use in the treatment of urothelial carcinoma as disclosed herein, the at least two FGFR genetic alterations comprise FGFR3 G370C and FGFR3 S249C; FGFR3 R248C and FGFR3 Y373C; FGFR3 G370C and FGFR2-BICC1; FGFR3 G370C and FGFR3-TACC3 V1; FGFR3 R248C and FGFR3-TACC3 V1; or FGFR3 R248C, FGFR3 S249 and FGFR3-TACC3 V1.

Evaluating a Sample for the Presence of at Least Two FGFR Genetic Alterations Also described herein are methods of treating urothelial carcinoma in a patient harboring at least two FGFR genetic alterations comprising, consisting of, or consisting essentially of administering a FGFR inhibitor to the patient, wherein: (a) two or more of the at least two FGFR genetic alterations are FGFR2 fusions; (b) one or more of the at least two FGFR genetic alterations is an FGFR2 fusion and one or more of the at least two FGFR genetic alterations is an FGFR3 fusion; (c) two or more of the at least two FGFR genetic alterations are FGFR3 mutations; (d) one or more of the at least two FGFR genetic alterations is an FGFR3 mutation and one or more of the at least two FGFR genetic alterations is an FGFR2 fusion; or (e) one or more of the at least two FGFR genetic alterations is an FGFR3 mutation and one or more of the at least two FGFR genetic alterations is an FGFR3 fusion. In certain embodiments, the methods of treating urothelial carcinoma in a patient harboring at least two FGFR genetic alterations further comprise evaluating a biological sample from the patient for the presence of the at least two FGFR genetic alterations prior to administration of the FGFR inhibitor.

The following methods for evaluating a biological sample for the presence of at least two FGFR genetic alterations apply equally to any of the above disclosed methods of treatment and uses.

The disclosed methods are suitable for treating cancer in a patient if at least two FGFR genetic alterations are present in a biological sample from the patient. In some embodiments, the FGFR genetic alterations can be one or more FGFR fusion genes. In some embodiments, the FGFR genetic alterations can be one or more FGFR mutations. In some embodiments, the FGFR genetic alterations can be one or more FGFR amplifications. In some embodiments, a combination of the one or more FGFR genetic alterations can be present in the biological sample from the patient. For example, in some embodiments, the FGFR genetic alterations can be one or more FGFR fusion genes and one or more FGFR amplifications.

In some embodiments, the FGFR genetic alterations can be one or more FGFR fusion genes and one or more FGFR mutations. In some embodiments, the FGFR alterations can be one or more FGFR mutations and one or more FGFR amplifications. In yet other embodiments, the FGFR alterations can be one or more FGFR fusion genes, mutations, and amplifications. Exemplary FGFR fusion genes are provided in Table 1 and include, but are not limited to, FGFR2-BICC1; FGFR2-CASP7; FGFR3-BAIAP2L1; FGFR3-TACC3 V1; FGFR3-TACC3 V3; or any combination thereof. Exemplary FGFR3 mutations are provided in Table 2 and include, but are not limited to, FGFR3 R248C, FGFR3 S249C, FGFR3 G370C, FGFR3 Y373C, or any combination thereof Exemplary combinations of FGFR genetic alterations are provided in Table 3.

TABLE 3

Exemplary FGFR genetic alterations

| FGFR Genetic Alteration(s) 1 | FGFR Genetic Alteration(s) 2 |
|---|---|
| FGFR2 or FGFR3 fusion | |
| FGFR2-BICC1 | FGFR2-CASP7 |
| FGFR2-CASP7 | FGFR3-BAIAP 2L1 |
| FGFR2-CASP7 | FGFR3-TACC3 V1 |
| FGFR2-CASP7 | FGFR3-TACC3 V3 |
| FGFR3 mutation | |
| FGFR3 G370C | FGFR3 S249C |
| FGFR3 R48C | FGFR3 Y373C |
| FGFR3 S249C | FGFR3 Y373C |
| FGFR2/3 fusions and mutations | |
| FGFR3 G370C | FGFR2-BICC1 |
| FGFR3 G370C | FGFR3-TACC3 V1 |
| FGFR3 R248C | FGFR3-TACC3 V1 |
| FGFR3 S249C | FGFR3-BAIAP 2L1 |
| FGFR3 R248C & S249 | FGFR3-TACC3 VI |
| FGFR3 S249C & Y373C | FGFR2-CASP7/ FGFR3-BAIAP2L1/ FGFR3-TACC3V1/ FGFR3-TACC3 V3 |

Suitable methods for evaluating a biological sample for the presence of at least two FGFR genetic alterations are described in the methods section herein and in WO 2016/048833, which are incorporated herein in their entirety. For example, and without intent to be limiting, evaluating a biological sample for the presence of one or more FGFR variants can comprise any combination of the following steps: isolating RNA from the biological sample; synthesizing cDNA from the RNA; and amplifying the cDNA (preamplified or non-preamplified). In some embodiments, evaluating a biological sample for the presence of one or more FGFR variants can comprise: amplifying cDNA from the patient with a pair of primers that bind to and amplify one or more FGFR variants; and determining whether the one or more FGFR variants are present in the sample. In some aspects, the cDNA can be pre-amplified. In some aspects, the evaluating step can comprise isolating RNA from the sample, synthesizing cDNA from the isolated RNA, and pre-amplifying the cDNA.

Suitable primer pairs for performing an amplification step include, but are not limited to, those disclosed in WO 2016/048833, as exemplified below:

particular over-expression of FGFR1, or gain-of-function genetic alterations of FGFR2 or FGFR3 may be particularly sensitive to FGFR inhibitors.

The methods, compounds, and uses can further comprise evaluating the presence of at least two FGFR genetic alterations in the biological sample before the administering step.

The diagnostic tests and screens are typically conducted on a biological sample selected from tumor biopsy samples, blood samples (isolation and enrichment of shed tumor cells), stool biopsies, sputum, chromosome analysis, pleural fluid, peritoneal fluid, buccal spears, biopsy, circulating DNA, or urine. In certain embodiments, the biological sample is blood, lymph fluid, bone marrow, a solid tumor sample, or any combination thereof. In certain embodiments, the biological sample is a solid tumor sample.

TABLE 4

| Target | Forward Primer | Reverse Primer 5'-3' |
|---|---|---|
| FGFR3-TACC3 V1 | GACCTGGACCGTGTCCTTACC (SEQ ID NO: 5) | CTTCCCCAGTTCCAGGTTCTT (SEQ ID NO: 6) |
| FGFR3-TACC3 V3 | AGGACCTGGACCGTGTCCTT (SEQ ID NO: 7) | TATAGGTCCGGTGGACAGGG (SEQ ID NO: 8) |
| FGFR3-BAIAP2L1 | CTGGACCGTGTCCTTACCGT (SEQ ID NO: 9) | GCAGCCCAGGATTGAACTGT (SEQ ID NO: 10) |
| FGFR2-BICC1 | TGGATCGAATTCTCACTCTCACA (SEQ ID NO: 11) | GCCAAGCAATCTGCGTATTTG (SEQ ID NO: 12) |
| FGFR2-CASP7 | GCTCTTCAATACAGCCCTGATCA (SEQ ID NO: 13) | ACTTGGATCGAATTCTCACTCTCA (SEQ ID NO: 14) |
| FGFR2-CCDC6 | TGGATCGAATTCTCACTCTCACA (SEQ ID NO: 15) | GCAAAGCCTGAATTTTCTTGAATAA (SEQ ID NO: 16) |
| FGFR3 R248C | GCATCCGGCAGACGTACA (SEQ ID NO: 17) | CCCCGCCTGCAGGAT (SEQ ID NO: 18) |
| FGFR3 S249C | GCATCCGGCAGACGTACA (SEQ ID NO: 19) | CCCCGCCTGCAGGAT (SEQ ID NO: 20) |
| FGFR3 G370C | AGGAGCTGGTGGAGGCTGA (SEQ ID NO: 21) | CCGTAGCTGAGGATGCCTG (SEQ ID NO: 22) |
| FGFR3 Y373C | CTGGTGGAGGCTGACGAG (SEQ ID NO: 23) | AGCCCACCCCGTAGCT (SEQ ID NO: 24) |
| FGFR3 R248C | GTCGTGGAGAACAAGTTTGGC (SEQ ID NO: 25) | GTCTGGTTGGCCGGCAG (SEQ ID NO: 26) |
| FGFR3 S249C | GTCGTGGAGAACAAGTTTGGC (SEQ ID NO: 27) | GTCTGGTTGGCCGGCAG (SEQ ID NO: 28) |
| FGFR3 G370C | AGGAGCTGGTGGAGGCTGA (SEQ ID NO: 29) | CCGTAGCTGAGGATGCCTG (SEQ ID NO: 30) |
| FGFR3 Y373C | GACGAGGCGGGCAGTG (SEQ ID NO: 31) | GAAGAAGCCCACCCCGTAG (SEQ ID NO: 32) |

The presence of the at least two FGFR genetic alterations can be evaluated at any suitable time point including upon diagnosis, following tumor resection, following first-line therapy, during clinical treatment, or any combination thereof For example, a biological sample taken from a patient may be analyzed to determine whether a condition or disease, such as cancer, that the patient is or may be suffering from is one which is characterized by a genetic abnormality or abnormal protein expression which leads to up-regulation of the levels or activity of FGFR or to sensitization of a pathway to normal FGFR activity, or to upregulation of these growth factor signaling pathways such as growth factor ligand levels or growth factor ligand activity or to upregulation of a biochemical pathway downstream of FGFR activation.

Examples of such abnormalities that result in activation or sensitization of the FGFR signal include loss of, or inhibition of apoptotic pathways, up-regulation of the receptors or ligands, or presence of genetic alterations of the receptors or ligands e.g. PTK variants. Tumors with genetic alterations of FGFR1, FGFR2 or FGFR3 or FGFR4 or up-regulation, in Methods of identification and analysis of genetic alterations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying an FGFR genetic alteration may mean that the patient would be particularly suitable for treatment with erdafitinib. Tumors may preferentially be screened for presence of a FGFR genetic alteration prior to treatment. The screening process will typically involve direct sequencing, oligonucleotide microarray analysis, or a mutant specific antibody. In addition, diagnosis of tumor with such genetic alterations could be performed using techniques known to a person skilled in the art and as described herein such as RT-PCR and FISH.

In addition, mutant forms of, for example FGFR, can be identified by direct sequencing of, for example, tumor biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumor is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), 3rd Ed, Molecular Cloning: A Laboratory Manual, Cold Spring Harbor Laboratory Press. Alternatively, a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridization technique for assessing mRNA expression would be fluorescence in-situ hybridization (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer,* 3:3). Briefly, the protocol is as follows: double-stranded cDNA is synthesized from total RNA Using a (dT)24 oligomer (SEQ ID NO: 38: ttttttttt ttttttttt tttt) for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, CA, USA), and then hybridized overnight on Human Genome Arrays.

Alternatively, the protein products expressed from the mRNAs may be assayed by immunohistochemistry of tumor samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site-specific antibodies. The skilled person will recognize that all such well-known techniques for detection of upregulation of FGFR, and/or VEGFR, or detection of FGFR, and/or VEGFR variants or mutants could be applicable in the present case.

Abnormal levels of proteins such as FGFR can be measured using standard enzyme assays, for example, those assays described herein. Activation or overexpression could also be detected in a tissue sample, for example, a tumor tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR including the isoforms thereof, include the measurement of microvessel density. This can for example be measured using methods described by Orre and Rogers (Int J Cancer (1999), 84(2) 101-8). Assay methods also include the use of markers.

Therefore, all of these techniques could also be used to identify tumors particularly suitable for treatment with the compounds of the invention.

Erdafitinib is in particular useful in treatment of a patient having at least two FGFR genetic alterations. In certain embodiments, erdafitinib is useful in treating a patient having at least two FGFR genetic alterations, wherein: a) two or more of the at least two FGFR genetic alterations are FGFR2 fusions; (b) one or more of the at least two FGFR genetic alterations is an FGFR2 fusion and one or more of the at least two FGFR genetic alterations is an FGFR3 fusion; (c) two or more of the at least two FGFR genetic alterations are FGFR3 mutations; (d) one or more of the at least two FGFR genetic alterations is an FGFR3 mutation and one or more of the at least two FGFR genetic alterations is an FGFR2 fusion; or (e) one or more of the at least two FGFR genetic alterations is an FGFR3 mutation and one or more of the at least two FGFR genetic alterations is an FGFR3 fusion.

Pharmaceutical Compositions and Routes of Administration

In view of its useful pharmacological properties, the FGFR inhibitor generally, and erdafitinib more specifically, may be formulated into various pharmaceutical forms for administration purposes.

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions, an effective amount of the FGFR inhibitor generally and erdafitinib more specifically, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intravaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

The pharmaceutical compositions of the invention, in particular capsules and/or tablets, may include one or more pharmaceutically acceptable excipients (pharmaceutically acceptable carrier) such as disintegrants, diluents, fillers, binders, buffering agents, lubricants, glidants, thickening agents, sweetening agents, flavors, colorants, preservatives and the like. Some excipients can serve multiple purposes.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose sodium (crosslinked sodium carboxymethylcellulose). The amount of disintegrant in the tablets according to the present invention may conveniently range from about 2.5 to about 15% w/w and preferably range from about 2.5 to 7% w/w, in particular range from about 2.5 to 5% w/w. Because disintegrants by their nature yield sustained release formulations when employed in bulk, it is advantageous to dilute them with an inert substance called a diluent or filler.

A variety of materials may be used as diluents or fillers. Examples are lactose monohydrate, anhydrous lactose, sucrose, dextrose, mannitol, sorbitol, starch, cellulose (e.g. micro-crystalline cellulose (Avicel™), silicified microcrystalline cellulose), dihydrated or anhydrous dibasic calcium phosphate, and others known in the art, and mixtures thereof (e.g. spray-dried mixture of lactose monohydrate (75%) with microcrystalline cellulose (25%) which is commercially available as Microcelac™). Preferred are microcrystalline cellulose and mannitol. The total amount of diluent or filler in the pharmaceutical compositions of the present invention may conveniently range from about 20% to about 95% w/w and preferably ranges from about 55% to about 95% w/w, or from about 70% to about 95% w/w, or from about 80% to about 95% w/w, or from about 85% to about 95%.

Lubricants and glidants can be employed in the manufacture of certain dosage forms, and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, colloidal anhydrous silica talc, mixtures thereof, and others known in the art. Interesting lubricants are magnesium stearate, and mixtures of magnesium stearate with colloidal silica, magnesium stearate being preferred. A preferred glidant is colloidal anhydrous silica.

If present, glidants generally comprise 0.2 to 7.0% w/w of the total composition weight, in particular 0.5 to 1.5% w/w, more in particular 1 to 1.5% w/w.

If present, lubricants generally comprise 0.2 to 7.0% w/w of the total composition weight, in particular 0.2 to 2% w/w, or 0.5 to 2% w/w, or 0.5 to 1.75% w/w, or 0.5 to 1.5% w/w.

Binders can optionally be employed in the pharmaceutical compositions of the present invention. Suitable binders are water-soluble polymers, such as alkylcelluloses such as methylcellulose; hydroxyalkylcelluloses such as hydroxymethylcellulose, hydroxyethylcellulose, hydroxypropylcellulose and hydroxybutylcellulose; hydroxyalkyl alkylcelluloses such as hydroxyethyl methylcellulose and hydroxypropyl methylcellulose; carboxyalkylcelluloses such as carboxymethylcellulose; alkali metal salts of carboxyalkylcelluloses such as sodium carboxymethylcellulose; carboxyalkylalkylcelluloses such as carboxymethylethylcellulose; carboxyalkylcellulose esters; starches; pectines such as sodium carboxymethylamylopectine; chitin derivates such as chitosan; di-, oligo- and polysaccharides such as trehalose, cyclodextrins and derivatives thereof, alginic acid, alkali metal and ammonium salts thereof, carrageenans, galactomannans, tragacanth, agar agar, gummi arabicum, guar gummi and xanthan gummi; polyacrylic acids and the salts thereof; polymethacrylic acids, the salts and esters thereof, methacrylate copolymers; polyvinylpyrrolidone (PVP), polyvinylalcohol (PVA) and copolymers thereof, e.g. PVP-VA. Preferably, the water-soluble polymer is a hydroxyalkyl alkylcelluloses, such as for example hydroxypropylmethyl cellulose, e.g. hydroxypropylmethyl cellulose 15 cps.

Other excipients such as coloring agents and pigments may also be added to the compositions of the invention. Coloring agents and pigments include titanium dioxide and dyes suitable for food. A coloring agent or a pigment is an optional ingredient in the formulation of the invention, but when used the coloring agent can be present in an amount up to 3.5% w/w based on the total composition weight.

Flavors are optional in the composition and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, *eucalyptus*, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth. The amount of flavor may depend on a number of factors including the organoleptic effect desired. Generally, the flavor will be present in an amount from about 0% to about 3% (w/w).

Formaldehyde scavengers are compounds that are capable of absorbing formaldehyde. They include compounds comprising a nitrogen center that is reactive with formaldehyde, such as to form one or more reversible or irreversible bonds between the formaldehyde scavenger and formaldehyde. For example, the formaldehyde scavenger comprises one or more nitrogen atoms/centers that are reactive with formaldehyde to form a schiff base imine that is capable of subsequently binding with formaldehyde. For example, the formaldehyde scavenger comprises one or more nitrogen centers that are reactive with formaldehyde to form one or more 5-8 membered cyclic rings. The formaldehyde scavenger preferably comprises one or more amine or amide groups. For example, the formaldehyde scavenger can be an amino acid, an amino sugar, an alpha amine compound, or a conjugate or derivative thereof, or a mixture thereof. The formaldehyde scavenger may comprise two or more amines and/or amides.

Formaldehyde scavengers include, for example, glycine, alanine, serine, threonine, cysteine, valine, lecuine, isoleucine, methionine, phenylalanine, tyrosine, aspartic acid, glutamic acid, arginine, lysine, ornithine, citrulline, taurine pyrrolysine, meglumine, histidine, aspartame, proline, tryptophan, citrulline, pyrrolysine, asparagine, glutamine, or a conjugate or mixture thereof; or, whenever possible, pharmaceutically acceptable salts thereof.

In an aspect of the invention, the formaldehyde scavenger is meglumine or a pharmaceutically acceptable salt thereof, in particular meglumine base.

It is another object of the invention to provide a process of preparing a pharmaceutical composition as described herein, in particular in the form of a tablet or a capsule, characterized by blending a formaldehyde scavenger, in particular meglumine, and erdafitinib, a pharmaceutically acceptable salt thereof or a solvate thereof, in particular erdafitinib base, with a pharmaceutically acceptable carrier and compressing said blend into tablets or filling said blend in capsules.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof Preferred forms are tablets and capsules.

In certain embodiments, the FGFR inhibitor, or erdafitinib specifically, is present in a solid unit dosage form, and a solid unit dosage form suitable for oral administration. The unit dosage form may contain about 1, 2, 3, 4, 5, 6, 7, 8, 9, or 10 mg of the FGFR inhibitor per unit dose form or an amount in a range bounded by two of these values, in particular 3, 4 or 5 mg per unit dose.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

Tablets or capsules of the present invention may further be film-coated e.g. to improve taste, to provide ease of swallowing and an elegant appearance. Polymeric film-coating materials are known in the art. Preferred film coatings are water-based film coatings opposed to solvent based film coatings because the latter may contain more traces of aldehydes. A preferred film-coating material is Opadry® II aqueous film coating system, e.g. Opadry® II 85F, such as Opadry® II 85F92209. Further preferred film coatings are water-based film coatings that protects from environmental moisture, such as Readilycoat® (e.g. Readilycoat® D), AquaPolish® MS, Opadry® amb, Opadry® amb II, which are aqueous moisture barrier film coating systems. A preferred film-coating is Opadry® amb II, a high performance moisture barrier film coating which is a PVA-based immediate release system, without polyethylene glycol.

In tablets according to the invention, the film coat in terms of weight preferably accounts for about 4% (w/w) or less of the total tablet weight.

For capsules according to the present invention, hypromellose (HPMC) capsules are preferred over gelatin capsules.

In an aspect of the invention, the pharmaceutical compositions as described herein, in particular in the form of a capsule or a tablet, comprise from 0.5 mg to 20 mg base equivalent, or from 2 mg to 20 mg base equivalent, or from 0.5 mg to 12 mg base equivalent, or from 2 mg to 12 mg base equivalent, or from 2 mg to 10 mg base equivalent, or from 2 mg to 6 mg base equivalent, or 2 mg base equivalent, 3 mg base equivalent, 4 mg base equivalent, 5 mg base equivalent, 6 mg base equivalent, 7 mg base equivalent, 8 mg base equivalent, 9 mg base equivalent, 10 mg base equivalent, 11 mg base equivalent or 12 mg base equivalent of erdafitinib, a pharmaceutically acceptable salt thereof or a solvate thereof. In particular, the pharmaceutical compositions as described herein comprise 3 mg base equivalent, 4 mg base equivalent or 5 mg base equivalent of erdafitinib, a pharmaceutically acceptable salt thereof or a solvate thereof.

In an aspect of the invention, the pharmaceutical compositions as described herein, in particular in the form of a capsule or a tablet, comprise from 0.5 mg to 20 mg, or from 2 mg to 20 mg, or from 0.5 mg to 12 mg, or from 2 mg to 12 mg, or from 2 mg to 10 mg, or from 2 mg to 6 mg, or 2 mg, 3 mg, 4 mg, 5 mg, 6 mg, 7 mg, 8 mg, 9 mg, 10 mg, 11 mg or 12 mg of erdafitinib base. In particular, the pharmaceutical compositions as described herein comprise 3 mg, 4 mg or 5 mg of erdafitinib base. In particular, the pharmaceutical compositions as described herein comprise 3 mg, 4 mg or 5 mg of erdafitinib base and from about 0.5 to about 5% w/w, from about 0.5 to about 3% w/w, from about 0.5 to about 2% w/w, from about 0.5 to about 1.5% w/w, or from about 0.5 to about 1% w/w of a formaldehyde scavenger, in particular meglumine. In particular, the pharmaceutical compositions as described herein comprise 3 mg, 4 mg or 5 mg of erdafitinib base and from about 0.5 to about 1.5% w/w or from about 0.5 to about 1% w/w of a formaldehyde scavenger, in particular meglumine.

In an aspect of the invention, more than one, e.g. two, pharmaceutical compositions as described herein can be administered in order to obtain a desired dose, e.g. a daily dose.

The amount of formaldehyde scavenger, in particular meglumine, in the pharmaceutical compositions according to the present invention may range from about 0.1 to about 10% w/w, about 0.1 to about 5% w/w, from about 0.1 to about 3% w/w, from about 0.1 to about 2% w/w, from about 0.1 to about 1.5% w/w, from about 0.1 to about 1% w/w, from about 0.5 to about 5% w/w, from about 0.5 to about 3% w/w, from about 0.5 to about 2% w/w, from about 0.5 to about 1.5% w/w, from about 0.5 to about 1% w/w.

Studies that look at safety also seek to identify any potential adverse effects that may result from exposure to the drug. Efficacy is often measured by determining whether an active pharmaceutical ingredient demonstrates a health benefit over a placebo or other intervention when tested in an appropriate situation, such as a tightly controlled clinical trial.

The term "acceptable" with respect to a formulation, composition or ingredient, as used herein, means that the beneficial effects of that formulation, composition or ingredient on the general health of the human being treated substantially outweigh its detrimental effects, to the extent any exist.

All formulations for oral administration are in dosage form suitable for such administration.

Methods of Dosing and Treatment Regimens

The FGFR inhibitor generally, and erdafitinib specifically, is administered in an amount sufficient to exert its anti-tumor activity. Those skilled in the art could easily determine the effective amount from the test results presented hereinafter. In general, it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

In one aspect, described herein are methods of treating urothelial carcinoma or use for the treatment of urothelial carcinoma comprising, consisting of, or consisting essentially of administering a safe and effective amount of an FGFR inhibitor to a patient with urothelial carcinoma, wherein the FGFR inhibitor is administered orally. In some embodiments, the FGFR inhibitor generally, and erdafitinib specifically, is administered daily, in particular once daily. In some embodiments, the FGFR inhibitor generally, and erdafitinib specifically, is administered twice-a-day. In some embodiments, the FGFR inhibitor generally, and erdafitinib specifically, is administered three times a day. In some embodiments, the FGFR inhibitor generally, and erdafitinib specifically, is administered four times a day. In some embodiments, the FGFR inhibitor generally, and erdafitinib specifically, is administered every other day. In some embodiments, the FGFR inhibitor generally, and erdafitinib specifically, is administered weekly. In some embodiments, the FGFR inhibitor generally, and erdafitinib specifically, is administered twice a week. In some embodiments, the FGFR inhibitor generally, and erdafitinib specifically, is administered every other week. In some embodiments, the FGFR inhibitor generally, and erdafitinib specifically, is administered orally on a continuous daily dosage schedule.

In general, doses of the FGFR inhibitor, and erdafitinib specifically, employed for treatment of the diseases or conditions described herein in humans are typically in the range of about 1 to 20 mg per day. In some embodiments, the FGFR inhibitor, and erdafitinib specifically, is administered orally to the human at a dose of about 1 mg per day, about 2 mg per day, about 3 mg per day, about 4 mg per day, about 5 mg per day, about 6 mg per day, about 7 mg per day, about 8 mg per day, about 9 mg per day, about 10 mg per day, about 11 mg per day, about 12 mg per day, about 13 mg per day, about 14 mg per day, about 15 mg per day, about 16 mg per day, about 17 mg per day, about 18 mg per day, about 19 mg per day or about 20 mg per day.

In certain embodiments, erdafitinib is administered orally at a dose of about 6 mg once daily.

In certain embodiments, erdafitinib is administered orally at a dose of about 8 mg once daily. In some embodiments, erdafitinib is administered orally at a dose of about 8 mg once daily on a continuous daily dosing schedule. In further embodiments, the dose of erdafitinib is increased from 8 mg once daily to 9 mg once daily at 14 to 21 days after initiating treatment if: (a) the patient exhibits a serum phosphate ($PO_4$) level that is less than about 5.5 mg/dL at 14-21 days after initiating treatment; and (b) administration of erdafitinib at 8 mg once daily resulted in no ocular disorder; or (c) administration of erdafitinib at 8 mg once daily resulted in no Grade 2 or greater adverse reaction.

In certain embodiments, the dose of erdafitinib is increased from 8 mg once daily to 9 mg once daily at 14 days after initiating treatment. In certain embodiments, the dose of erdafitinib is increased from 8 mg once daily to 9 mg once daily at 15 days after initiating treatment. In certain embodiments, the dose of erdafitinib is increased from 8 mg once daily to 9 mg once daily at 16 days after initiating treatment. In certain embodiments, the dose of erdafitinib is increased from 8 mg once daily to 9 mg once daily at 17 days after initiating treatment. In certain embodiments, the dose of erdafitinib is increased from 8 mg once daily to 9 mg once daily at 18 days after initiating treatment. In certain embodiments, the dose of erdafitinib is increased from 8 mg once daily to 9 mg once daily at 19 days after initiating treatment. In certain embodiments, the dose of erdafitinib is increased from 8 mg once daily to 9 mg once daily at 20 days after initiating treatment.

In an embodiment, erdafitinib is administered at a dose of 10 mg. In an embodiment, erdafitinib is administered at a dose of 10 mg intermittently. In an embodiment, erdafitinib is administered at a dose of 10 mg intermittently 7 days on/7 days off.

In an embodiment, erdafitinib is administered at a dose of 8 mg, in particular 8 mg once daily. In an embodiment, erdafitinib is administered at a dose of 8 mg, in particular 8 mg once daily, with an option to uptitrate to 9 mg depending on serum phosphate levels (e.g. serum phosphate levels are <5.5 mg/dL, or are <7 mg/dL or range from and include 7 mg/dL to ≤9 mg/dL or are ≤9 mg/dL), and depending on treatment-related adverse events observed. In an embodiment, the levels of serum phosphate for determining whether or not to up-titrate are measured on a treatment day during the first cycle of erdafitinib treatment, in particular on day 14±2 days, more in particular on day 14, of erdafitinib administration.

In an embodiment, the treatment cycle as used herein is a 28-day cycle.

In one embodiment, the desired dose is conveniently presented in a single dose or in divided doses administered simultaneously (or over a short period of time) or at appropriate intervals, for example as two, three, four or more sub-doses per day. In some embodiments, the FGFR inhibitor is conveniently presented in divided doses that are administered simultaneously (or over a short period of time) once a day. In some embodiments, the FGFR inhibitor is conveniently presented in divided doses that are administered in equal portions twice-a-day. In some embodiments, the FGFR inhibitor is conveniently presented in divided doses that are administered in equal portions three times a day. In some embodiments, the FGFR inhibitor is conveniently presented in divided doses that are administered in equal portions four times a day.

In certain embodiments, the desired dose may be delivered in 1, 2, 3, 4, 5, 6, 7, 8, 9, or 10 fractional unit dosages throughout the course of the day, such that the total amount of FGFR inhibitor delivered by the fractional unit dosages over the course of the day provides the total daily dosage.

In some embodiments, the amount of the FGFR inhibitor that is given to the human varies depending upon factors such as, but not limited to, condition and severity of the disease or condition, and the identity (e.g., weight) of the human, and the particular additional therapeutic agents that are administered (if applicable).

In further embodiments, the patient received at least one prior therapy for the treatment of urothelial carcinoma. In some embodiments, the at least one prior therapy for the treatment of urothelial carcinoma is platinum-containing chemotherapy. In certain embodiments, the urothelial carcinoma progressed during or following at least one line of the platinum-containing chemotherapy. In further embodiments, the platinum-containing chemotherapy is neoadjuvant platinum-containing chemotherapy or adjuvant platinum-containing chemotherapy. In still further embodiments, the urothelial carcinoma progressed during or within 12 months following at least one line of the neoadjuvant platinum-containing chemotherapy or adjuvant platinum-containing chemotherapy.

Kits Articles of Manufacture

For use in the methods of use described herein, kits and articles of manufacture are also described. Such kits include a package or container that is compartmentalized to receive one or more dosages of the pharmaceutical compositions disclosed herein. Suitable containers include, for example, bottles. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert.

In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Nucleotide Sequences of FGFR Fusion Genes

The nucleotide sequences for the FGFR fusion cDNA are provided in Table 5. The underlined sequences correspond to either FGFR3 or FGFR2, the sequences in black represent the fusion partners and the sequence in italic fonts represent the intron sequence of the FGFR3 gene.

TABLE 5

| | |
|---|---|
| FGFR3-TACC3 v1<br>(2850 base pairs)<br>(SEQ ID NO: 33) | >ATGGGCGCCCCTGCCTGCGCCCTCGCGCTCTGCGTGGCCGTGGCCATCGTG<br>GCCGGCGCCTCCTCGGAGTCCTTGGGGACGGAGCAGCGCGTCGTGGGGCG<br>AGCGGCAGAAGTCCCGGGCCCAGAGCCCGGCCAGCAGGAGCAGTTGGTCT<br>TCGGCAGCGGGGATGCTGTGGAGCTGAGCTGTCCCCCGCCCGGGGGTGGTC<br>CCATGGGGCCCACTGTCTGGGTCAAGGATGGCACAGGGCTGGTGCCCTCGG<br>AGCGTGTCCTGGTGGGGCCCCAGCGGCTGCAGGTGCTGAATGCCTCCCACG<br>AGGACTCCGGGGCCTACAGCTGCCGGCAGCGGCTCACGCAGCGCGTACTGT<br>GCCACTTCAGTGTGCGGGTGACAGACGCTCCATCCTCGGGAGATGACGAAG<br>ACGGGGAGGACGAGGCTGAGGACACAGGTGTGGACACAGGGGCCCCTTAC<br>TGGACACGGCCCGAGCGGATGGACAAGAAGCTGCTGGCCGTGCCGGCCGC<br>CAACACCGTCCGCTTCCGCTGCCCAGCCGCTGGCAACCCCACTCCCTCCATC<br>TCCTGGCTGAAGAACGGCAGGGAGTTCCGCGGCGAGCACCGCATTGGAGG<br>CATCAAGCTGCGGCATCAGCAGTGGAGCCTGGTCATGGAAAGCGTGGTGCC<br>CTCGGACCGCGGCAACTACACCTGCGTCGTGGAGAACAAGTTTGGCAGCAT<br>CCGGCAGACGTACACGCTGGACGTGCTGGAGCGCTCCCCGCACCGGCCCAT<br>CCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGC<br>TCAAGCACGTGGAGGTGAATGGCAGCAAGGTGGGCCCGGACGGCACACCC<br>TACGTTACCGTGCTCAAGACGGCGGGCGCTAACACCACCGACAAGGAGCT<br>AGAGGTTCTCTCCTTGCACAACGTCACCTTTGAGGACGCCGGGGAGTACAC<br>CTGCCTGGCGGGCAATTCTATTGGGTTTTCTCATCACTCTGCGTGGCTGGTG<br>GTGCTGCCAGCCGAGGAGGAGCTGGTGGAGGCTGACGAGGCGGGCAGTGT<br>GTATGCAGGCATCCTCAGCTACGGGGTGGGCTTCTTCCTGTTCATCCTGGTG<br>GTGGCGGCTGTGACGCTCTGCCGCCTGCGCAGCCCCCCCAAGAAAGGCCTG<br>GGCTCCCCCACCGTGCACAAGATCTCCCGCTTCCCGCTCAAGCGACAGGTG<br>TCCCTGGAGTCCAACGCGTCCATGAGCTCCAACACACCACTGGTGCGCATC<br>GCAAGGCTGTCCTCAGGGGAGGGCCCCACGCTGGCCAATGTCTCCGAGCTC<br>GAGCTGCCTGCCGACCCCAAATGGGAGCTGTCTCGGGCCCGGCTGACCCTG |

TABLE 5-continued

| | |
|---|---|
| | GGCAAGCCCCTTGGGGAGGGCTGCTTCGGCCAGGTGGTCATGGCGGAGGC<br>CATCGGCATTGACAAGGACCGGGCCGCCAAGCCTGTCACCGTAGCCGTGAA<br>GATGCTGAAAGACGATGCCACTGACAAGGACCTGTCGGACCTGGTGTCTGA<br>GATGGAGATGATGAAGATGATCGGGAAACACAAAAACATCATCAACCTGC<br>TGGGCGCCTGCACGCAGGGCGGGCCCCTGTACGTGCTGGTGGAGTACGCGG<br>CCAAGGGTAACCTGCGGGAGTTTCTGCGGGCGCGGCGGCCCCCGGGCCTGG<br>ACTACTCCTTCGACACCTGCAAGCCGCCCGAGGAGCAGCTCACCTTCAAGG<br>ACCTGGTGTCCTGTGCCTACCAGGTGGCCCGGGGCATGGAGTACTTGGCCT<br>CCCAGAAGTGCATCCACAGGGACCTGGCTGCCCGCAATGTGCTGGTGACCG<br>AGGACAACGTGATGAAGATCGCAGACTTCGGGCTGGCCCGGGACGTGCAC<br>AACCTCGACTACTACAAGAAGACGACCAACGGCCGGCTGCCCGTGAAGTG<br>GATGGCGCCTGAGGCCTTGTTTGACCGAGTCTACACTCACCAGAGTGACGT<br>CTGGTCCTTTGGGGTCCTGCTCTGGGAGATCTTCACGCTGGGGGGCTCCCCG<br>TACCCCGGCATCCCTGTGGAGGAGCTCTTCAAGCTGCTGAAGGAGGGCCAC<br>CGCATGGACAAGCCCGCCAACTGCACACACGACCTGTACATGATCATGCGG<br>GAGTGCTGGCATGCCGCGCCCTCCCAGAGGCCCACCTTCAAGCAGCTGGTG<br>GAGGACCTGGACCGTGTCCTTACCGTGACGTCCACCGACGTAAAGGCGACA<br>CAGGAGGAGAACCGGGAGCTGAGGAGCAGGTGTGAGGAGCTCCACGGGA<br>AGAACCTGGAACTGGGGAAGATCATGGACAGGTTCGAAGAGGTTGTGTAC<br>CAGGCCATGGAGGAAGTTCAGAAGCAGAAGGAACTTTCCAAAGCTGAAAT<br>CCAGAAAGTTCTAAAAGAAAAAGACCAACTTACCACAGATCTGAACTCCAT<br>GGAGAAGTCCTTCTCCGACCTCTTCAAGCGTTTTGAGAAACAGAAAGAGGT<br>GATCGAGGGCTACCGCAAGAACGAAGAGTCACTGAAGAAGTGCGTGGAGG<br>ATTACCTGGCAAGGATCACCCAGGAGGGCCAGAGGTACCAAGCCCTGAAG<br>GCCCACGCGGAGGAGAAGCTGCAGCTGGCAAACGAGGAGATCGCCCAGGT<br>CCGGAGCAAGGCCCAGGCGGAAGCGTTGGCCCTCCAGGCCAGCCTGAGGA<br>AGGAGCAGATGCGCATCCAGTCGCTGGAGAAGACAGTGGAGCAGAAGACT<br>AAAGAGAACGAGGAGCTGACCAGGATCTGCGACGACCTCATCTCCAAGAT<br>GGAGAAGATCTGA |
| FGFR3-TACC3 v3<br>(2955 base pairs)<br>(SEQ ID NO: 34) | >ATGGGCGCCCCTGCCTGCGCCCTCGCGCTCTGCGTGGCCGTGGCCATCGTG<br>GCCGGCGCCTCCTCGGAGTCCTTGGGGACGGAGCAGCGCGTCGTGGGGCG<br>AGCGGCAGAAGTCCCGGGCCCAGAGCCCGGCCAGCAGGAGCAGTTGGTCT<br>TCGGCAGCGGGGATGCTGTGGAGCTGAGCTGTCCCCCGCCCGGGGGTGGTC<br>CCATGGGGCCCACTGTCTGGGTCAAGGATGGCACAGGGCTGGTGCCCTCGG<br>AGCGTGTCCTGGTGGGGCCCCAGCGGCTGCAGGTGCTGAATGCCTCCCACG<br>AGGACTCCGGGGCCTACAGCTGCCGGCAGCGGCTCACGCAGCGCGTACTGT<br>GCCACTTCAGTGTGCGGGTGACAGACGCTCCATCCTCGGGAGATGACGAAG<br>ACGGGGAGGACGAGGCTGAGGACACAGGTGTGGACACAGGGGCCCCTTAC<br>TGGACACGGCCCGAGCGGATGGACAAGAAGCTGCTGGCCGTGCCGGCCGC<br>CAACACCGTCCGCTTCCGCTGCCCAGCCGCTGGCAACCCCACTCCCTCCATC<br>TCCTGGCTGAAGAACGGCAGGGAGTTCCGCGGCGAGCACCGCATTGGAGG<br>CATCAAGCTGCGGCATCAGCAGTGGAGCCTGGTCATGGAAAGCGTGGTGCC<br>CTCGGACCGCGGCAACTACACCTGCGTCGTGGAGAACAAGTTTGGCAGCAT<br>CCGGCAGACGTACACGCTGGACGTGCTGGAGCGCTCCCCGCACCGGCCCAT<br>CCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGC<br>TCAAGCACGTGGAGGTGAATGGCAGCAAGGTGGGCCCGGACGGCACACCC<br>TACGTTACCGTGCTCAAGACGGCGGGCGCTAACACCACCGACAAGGAGCT<br>AGAGGTTCTCTCCTTGCACAACGTCACCTTTGAGGACGCCGGGGAGTACAC<br>CTGCCTGGCGGGCAATTCTATTGGGTTTTCTCATCACTCTGCGTGGCTGGTG<br>GTGCTGCCAGCCGAGGAGGAGCTGGTGGAGGCTGACGAGGCGGGCAGTGT<br>GTATGCAGGCATCCTCAGCTACGGGGTGGGCTTCTTCCTGTTCATCCTGGTG<br>GTGGCGGCTGTGACGCTCTGCCGCCTGCGCAGCCCCCCCAAGAAAGGCCTG<br>GGCTCCCCCACCGTGCACAAGATCTCCCGCTTCCCGCTCAAGCGACAGGTG<br>TCCCTGGAGTCCAACGCGTCCATGAGCTCCAACACACCACTGGTGCGCATC<br>GCAAGGCTGTCCTCAGGGGAGGGCCCCACGCTGGCCAATGTCTCCGAGCTC<br>GAGCTGCCTGCCGACCCCAAATGGGAGCTGTCTCGGGCCCGGCTGACCCTG<br>GGCAAGCCCCTTGGGGAGGGCTGCTTCGGCCAGGTGGTCATGGCGGAGGC<br>CATCGGCATTGACAAGGACCGGGCCGCCAAGCCTGTCACCGTAGCCGTGAA<br>GATGCTGAAAGACGATGCCACTGACAAGGACCTGTCGGACCTGGTGTCTGA<br>GATGGAGATGATGAAGATGATCGGGAAACACAAAAACATCATCAACCTGC<br>TGGGCGCCTGCACGCAGGGCGGGCCCCTGTACGTGCTGGTGGAGTACGCGG<br>CCAAGGGTAACCTGCGGGAGTTTCTGCGGGCGCGGCGGCCCCCGGGCCTGG<br>ACTACTCCTTCGACACCTGCAAGCCGCCCGAGGAGCAGCTCACCTTCAAGG<br>ACCTGGTGTCCTGTGCCTACCAGGTGGCCCGGGGCATGGAGTACTTGGCCT<br>CCCAGAAGTGCATCCACAGGGACCTGGCTGCCCGCAATGTGCTGGTGACCG<br>AGGACAACGTGATGAAGATCGCAGACTTCGGGCTGGCCCGGGACGTGCAC<br>AACCTCGACTACTACAAGAAGACGACCAACGGCCGGCTGCCCGTGAAGTG<br>GATGGCGCCTGAGGCCTTGTTTGACCGAGTCTACACTCACCAGAGTGACGT<br>CTGGTCCTTTGGGGTCCTGCTCTGGGAGATCTTCACGCTGGGGGGCTCCCCG<br>TACCCCGGCATCCCTGTGGAGGAGCTCTTCAAGCTGCTGAAGGAGGGCCAC<br>CGCATGGACAAGCCCGCCAACTGCACACACGACCTGTACATGATCATGCGG<br>GAGTGCTGGCATGCCGCGCCCTCCCAGAGGCCCACCTTCAAGCAGCTGGTG<br>GAGGACCTGGACCGTGTCCTTACCGTGACGTCCACCGACGTGCCAGGCCCA<br>CCCCCAGGTGTTCCCGCGCCTGGGGGCCCACCCCTGTCCACCGGACCTATA<br>GTGGACCTGCTCCAGTACAGCCAGAAGGACCTGGATGCAGTGGTAAAGGC<br>GACACAGGAGGAGAACCGGGAGCTGAGGAGCAGGTGTGAGGAGCTCCACG<br>GGAAGAACCTGGAACTGGGGAAGATCATGGACAGGTTCGAAGAGGTTGTG<br>TACCAGGCCATGGAGGAAGTTCAGAAGCAGAAGGAACTTTCCAAAGCTGA |

TABLE 5-continued

| | |
|---|---|
| | AATCCAGAAAGTTCTAAAAGAAAAAGACCAACTTACCACAGATCTGAACT<br>CCATGGAGAAGTCCTTCTCCGACCTCTTCAAGCGTTTTGAGAAACAGAAAG<br>AGGTGATCGAGGGCTACCGCAAGAACGAAGAGTCACTGAAGAAGTGCGTG<br>GAGGATTACCTGGCAAGGATCACCCAGGAGGGCCAGAGGTACCAAGCCCT<br>GAAGGCCCACGCGGAGGAGAAGCTGCAGCTGGCAAACGAGGAGATCGCCC<br>AGGTCCGGAGCAAGGCCCAGGCGGAAGCGTTGGCCCTCCAGGCCAGCCTG<br>AGGAAGGAGCAGATGCGCATCCAGTCGCTGGAGAAGACAGTGGAGCAGAA<br>GACTAAAGAGAACGAGGAGCTGACCAGGATCTGCGACGACCTCATCTCCA<br>AGATGGAGAAGATCTGA |
| FGFR3-BAIAP2L1<br>(3765 base pairs)<br>(SEQ ID NO: 35) | >ATGGGCGCCCCTGCCTGCGCCCTCGCGCTCTGCGTGGCCGTGGCCATCGTG<br>GCCGGCGCCTCCTCGGAGTCCTTGGGGACGGAGCAGCGCGTCGTGGGGCG<br>AGCGGCAGAAGTCCCGGGCCCAGAGCCCGGCCAGCAGGAGCAGTTGGTCT<br>TCGGCAGCGGGGATGCTGTGGAGCTGAGCTGTCCCCCGCCCGGGGGTGGTC<br>CCATGGGGCCCACTGTCTGGGTCAAGGATGGCACAGGGCTGGTGCCCTCGG<br>AGCGTGTCCTGGTGGGGCCCCAGCGGCTGCAGGTGCTGAATGCCTCCCACG<br>AGGACTCCGGGGCCTACAGCTGCCGGCAGCGGCTCACGCAGCGCGTACTGT<br>GCCACTTCAGTGTGCGGGTGACAGACGCTCCATCCTCGGGAGATGACGAAG<br>ACGGGGAGGACGAGGCTGAGGACACAGGTGTGGACACAGGGGCCCCTTAC<br>TGGACACGGCCCGAGCGGATGGACAAGAAGCTGCTGGCCGTGCCGGCCGC<br>CAACACCGTCCGCTTCCGCTGCCCAGCCGCTGGCAACCCCACTCCCTCCATC<br>TCCTGGCTGAAGAACGGCAGGGAGTTCCGCGGCGAGCACCGCATTGGAGG<br>CATCAAGCTGCGGCATCAGCAGTGGAGCCTGGTCATGGAAAGCGTGGTGCC<br>CTCGGACCGCGGCAACTACACCTGCGTCGTGGAGAACAAGTTTGGCAGCAT<br>CCGGCAGACGTACACGCTGGACGTGCTGGAGCGCTCCCCGCACCGGCCCAT<br>CCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGC<br>TCAAGCACGTGGAGGTGAATGGCAGCAAGGTGGGCCCGGACGGCACACCC<br>TACGTTACCGTGCTCAAGTCCTGGATCAGTGAGAGTGTGGAGGCCGACGTG<br>CGCCTCCGCCTGGCCAATGTGTCGGAGCGGGACGGGGGCGAGTACCTCTGT<br>CGAGCCACCAATTTCATAGGCGTGGCCGAGAAGGCCTTTTGGCTGAGCGTT<br>CACGGGCCCCGAGCAGCCGAGGAGGAGCTGGTGGAGGCTGACGAGGCGGG<br>CAGTGTGTATGCAGGCATCCTCAGCTACGGGGTGGGCTTCTTCCTGTTCATC<br>CTGGTGGTGGCGGCTGTGACGCTCTGCCGCCTGCGCAGCCCCCCCAAGAAA<br>GGCCTGGGCTCCCCCACCGTGCACAAGATCTCCCGCTTCCCGCTCAAGCGA<br>CAGGTGTCCCTGGAGTCCAACGCGTCCATGAGCTCCAACACACCACTGGTG<br>CGCATCGCAAGGCTGTCCTCAGGGGAGGGCCCCACGCTGGCCAATGTCTCC<br>GAGCTCGAGCTGCCTGCCGACCCCAAATGGGAGCTGTCTCGGGCCCGGCTG<br>ACCCTGGGCAAGCCCCTTGGGGAGGGCTGCTTCGGCCAGGTGGTCATGGCG<br>GAGGCCATCGGCATTGACAAGGACCGGGCCGCCAAGCCTGTCACCGTAGC<br>CGTGAAGATGCTGAAAGACGATGCCACTGACAAGGACCTGTCGGACCTGG<br>TGTCTGAGATGGAGATGATGAAGATGATCGGGAAACACAAAAACATCATC<br>AACCTGCTGGGCGCCTGCACGCAGGGCGGGCCCCTGTACGTGCTGGTGGAG<br>TACGCGGCCAAGGGTAACCTGCGGGAGTTTCTGCGGGCGCGGCGGCCCCCG<br>GGCCTGGACTACTCCTTCGACACCTGCAAGCCGCCCGAGGAGCAGCTCACC<br>TTCAAGGACCTGGTGTCCTGTGCCTACCAGGTGGCCCGGGGCATGGAGTAC<br>TTGGCCTCCCAGAAGTGCATCCACAGGGACCTGGCTGCCCGCAATGTGCTG<br>GTGACCGAGGACAACGTGATGAAGATCGCAGACTTCGGGCTGGCCCGGGA<br>CGTGCACAACCTCGACTACTACAAGAAGACGACCAACGGCCGGCTGCCCGT<br>GAAGTGGATGGCGCCTGAGGCCTTGTTTGACCGAGTCTACACTCACCAGAG<br>TGACGTCTGGTCCTTTGGGGTCCTGCTCTGGGAGATCTTCACGCTGGGGGG<br>CTCCCCGTACCCCGGCATCCCTGTGGAGGAGCTCTTCAAGCTGCTGAAGGA<br>GGGCCACCGCATGGACAAGCCCGCCAACTGCACACACGACCTGTACATGAT<br>CATGCGGGAGTGCTGGCATGCCGCGCCCTCCCAGAGGCCCACCTTCAAGCA<br>GCTGGTGGAGGACCTGGACCGTGTCCTTACCGTGACGTCCACCGACAATGT<br>TATGGAACAGTTCAATCCTGGGCTGCGAAATTTAATAAACCTGGGGAAAAA<br>TTATGAGAAAGCTGTAAACGCTATGATCCTGGCAGGAAAAGCCTACTACGA<br>TGGAGTGGCCAAGATCGGTGAGATTGCCACTGGGTCCCCCGTGTCAACTGA<br>ACTGGGACATGTCCTCATAGAGATTTCAAGTACCCACAAGAAACTCAACGA<br>GAGTCTTGATGAAAATTTTAAAAAATTCCACAAAGAGATTATCCATGAGCT<br>GGAGAAGAAGATAGAACTTGACGTGAAATATATGAACGCAACTCTAAAAA<br>GATACCAAACAGAACACAAGAATAAATTAGAGTCTTTGGAGAAATCCCAA<br>GCTGAGTTGAAGAAGATCAGAAGGAAAAGCCAAGGAAGCCGAAACGCACT<br>CAAATATGAACACAAAGAAATTGAGTATGTGGAGACCGTTACTTCTCGTCA<br>GAGTGAAATCCAGAAATTCATTGCAGATGGTTGCAAAGAGGCTCTGCTTGA<br>AGAGAAGAGGCGCTTCTGCTTTCTGGTTGATAAGCACTGTGGCTTTGCAAA<br>CCACATACATTATTATCACTTACAGTCTGCAGAACTACTGAATTCCAAGCTG<br>CCTCGGTGGCAGGAGACCTGTGTTGATGCCATCAAAGTGCCAGAGAAAATC<br>ATGAATATGATCGAAGAAATAAAGACCCCAGCCTCTACCCCCGTGTCTGGA<br>ACTCCTCAGGCTTCACCCATGATCGAGAGAAGCAATGTGGTTAGGAAAGAT<br>TACGACACCCTTTCTAAATGCTCACCAAAGATGCCCCCCGCTCCTTCAGGC<br>AGAGCATATACCAGTCCCTTGATCGATATGTTTAATAACCCAGCCACGGCT<br>GCCCCGAATTCACAAAGGGTAAATAATTCAACAGGTACTTCCGAAGATCCC<br>AGTTTACAGCGATCAGTTTCGGTTGCAACGGGACTGAACATGATGAAGAAG<br>CAGAAAGTGAAGACCATCTTCCCGCACACTGCGGGCTCCAACAAGACCTTA<br>CTCAGCTTTGCACAGGGAGATGTCATCACGCTGCTCATCCCCGAGGAGAAG<br>GATGGCTGGCTCTATGGAGAACACGACGTGTCCAAGGCGAGGGGTTGGTTC<br>CCGTCGTCGTACACGAAGTTGCTGGAAGAAAATGAGACAGAAGCAGTGAC<br>CGTGCCCACGCCAAGCCCCACACCAGTGAGAAGCATCAGCACCGTGAACTT<br>GTCTGAGAATAGCAGTGTTGTCATCCCCCCACCCGACTACTTGGAATGCTT |

TABLE 5-continued

| | |
|---|---|
| | GTCCATGGGGGCAGCTGCCGACAGGAGAGCAGATTCGGCCAGGACGACAT<br>CCACCTTTAAGGCCCCAGCGTCCAAGCCCGAGACCGCGGCTCCTAACGATG<br>CCAACGGGACTGCAAAGCCGCCTTTTCTCAGCGGAGAAAACCCCTTTGCCA<br>CTGTGAAACTCCGCCCGACTGTGACGAATGATCGCTCGGCACCCATCATTC<br>GATGA |
| FGFR2-BICC1<br>(4989 base pairs)<br>(SEQ ID NO: 36) | >ATGGTCAGCTGGGGTCGTTTCATCTGCCTGGTCGTGGTCACCATGGCAACC<br>TTGTCCCTGGCCCGGCCCTCCTTCAGTTTAGTTGAGGATACCACATTAGAGC<br>CAGAAGAGCCACCAACCAAATACCAAATCTCTCAACCAGAAGTGTACGTG<br>GCTGCGCCAGGGGAGTCGCTAGAGGTGCGCTGCCTGTTGAAAGATGCCGCC<br>GTGATCAGTTGGACTAAGGATGGGGTGCACTTGGGGCCCAACAATAGGAC<br>AGTGCTTATTGGGGAGTACTTGCAGATAAAGGGCGCCACGCCTAGAGACTC<br>CGGCCTCTATGCTTGTACTGCCAGTAGGACTGTAGACAGTGAAACTTGGTA<br>CTTCATGGTGAATGTCACAGATGCCATCTCATCCGGAGATGATGAGGATGA<br>CACCGATGGTGCGGAAGATTTTGTCAGTGAGAACAGTAACAACAAGAGAG<br>CACCATACTGGACCAACACAGAAAAGATGGAAAAGCGGCTCCATGCTGTG<br>CCTGCGGCCAACACTGTCAAGTTTCGCTGCCCAGCCGGGGGGAACCCAATG<br>CCAACCATGCGGTGGCTGAAAAACGGGAAGGAGTTTAAGCAGGAGCATCG<br>CATTGGAGGCTACAAGGTACGAAACCAGCACTGGAGCCTCATTATGGAAA<br>GTGTGGTCCCATCTGACAAGGGAAATTATACCTGTGTAGTGGAGAATGAAT<br>ACGGGTCCATCAATCACACGTACCACCTGGATGTTGTGGAGCGATCGCCTC<br>ACCGGCCCATCCTCCAAGCCGGACTGCCGGCAAATGCCTCCACAGTGGTCG<br>GAGGAGACGTAGAGTTTGTCTGCAAGGTTTACAGTGATGCCCAGCCCCACA<br>TCCAGTGGATCAAGCACGTGGAAAAGAACGGCAGTAAATACGGGCCCGAC<br>GGGCTGCCCTACCTCAAGGTTCTCAAGGCCGCCGGTGTTAACACCACGGAC<br>AAAGAGATTGAGGTTCTCTATATTCGGAATGTAACTTTTGAGGACGCTGGG<br>GAATATACGTGCTTGGCGGGTAATTCTATTGGGATATCCTTTCACTCTGCAT<br>GGTTGACAGTTCTGCCAGCGCCTGGAAGAGAAAAGGAGATTACAGCTTCCC<br>CAGACTACCTGGAGATAGCCATTTACTGCATAGGGGTCTTCTTAATCGCCT<br>GTATGGTGGTAACAGTCATCCTGTGCCGAATGAAGAACACGACCAAGAAG<br>CCAGACTTCAGCAGCCAGCCGGCTGTGCACAAGCTGACCAAACGTATCCCC<br>CTGCGGAGACAGGTAACAGTTTCGGCTGAGTCCAGCTCCTCCATGAACTCC<br>AACACCCCGCTGGTGAGGATAACAACACGCCTCTCTTCAACGGCAGACACC<br>CCCATGCTGGCAGGGGTCTCCGAGTATGAACTTCCAGAGGACCCAAAATGG<br>GAGTTTCCAAGAGATAAGCTGACACTGGGCAAGCCCCTGGGAGAAGGTTG<br>CTTTGGGCAAGTGGTCATGGCGGAAGCAGTGGGAATTGACAAAGACAAGC<br>CCAAGGAGGCGGTCACCGTGGCCGTGAAGATGTTGAAAGATGATGCCACA<br>GAGAAAGACCTTTCTGATCTGGTGTCAGAGATGGAGATGATGAAGATGATT<br>GGGAAACACAAGAATATCATAAATCTTCTTGGAGCCTGCACACAGGATGG<br>GCCTCTCTATGTCATAGTTGAGTATGCCTCTAAAGGCAACCTCCGAGAATA<br>CCTCCGAGCCCGGAGGCCACCCGGGATGGAGTACTCCTATGACATTAACCG<br>TGTTCCTGAGGAGCAGATGACCTTCAAGGACTTGGTGTCATGCACCTACCA<br>GCTGGCCAGAGGCATGGAGTACTTGGCTTCCCAAAAATGTATTCATCGAGA<br>TTTAGCAGCCAGAAATGTTTTGGTAACAGAAAACAATGTGATGAAAATAGC<br>AGACTTTGGACTCGCCAGAGATATCAACAATATAGACTATTACAAAAAGAC<br>CACCAATGGGCGGCTTCCAGTCAAGTGGATGGCTCCAGAAGCCCTGTTTGA<br>TAGAGTATACACTCATCAGAGTGATGTCTGGTCCTTCGGGGTGTTAATGTG<br>GGAGATCTTCACTTTAGGGGGCTCGCCCTACCCAGGGATTCCCGTGGAGGA<br>ACTTTTTAAGCTGCTGAAGGAAGGACACAGAATGGATAAGCCAGCCAACT<br>GCACCAACGAACTGTACATGATGATGAGGGACTGTTGGCATGCAGTGCCCT<br>CCCAGAGACCAACGTTCAAGCAGTTGGTAGAAGACTTGGATCGAATTCTCA<br>CTCTCACAACCAATGAGATCATGGAGGAAACAAATACGCAGATTGCTTGGC<br>CATCAAAACTGAAGATCGGAGCCAAATCCAAGAAAGATCCCCATATTAAG<br>GTTTCTGGAAAGAAAGAAGATGTTAAAGAAGCCAAGGAAATGATCATGTC<br>TGTCTTAGACACAAAAAGCAATCGAGTCACACTGAAGATGGATGTTTCACA<br>TACAGAACATTCACATGTAATCGGCAAAGGTGGCAACAATATTAAAAAAGT<br>GATGGAAGAAACCGGATGCCATATCCACTTTCCAGATTCCAACAGGAATAA<br>CCAAGCAGAAAAAAGCAACCAGGTATCTATAGCGGGACAACCAGCAGGAG<br>TAGAATCTGCCCGAGTTAGAATTCGGGAGCTGCTTCCTTTGGTGCTGATGTT<br>TGAGCTACCAATTGCTGGAATTCTTCAACCGGTTCCTGATCCTAATTCCCCC<br>TCTATTCAGCATATATCACAAACGTACAATATTTCAGTATCATTTAAACAGC<br>GTTCCCGAATGTATGGTGCTACTGTCATAGTACGAGGGTCTCAGAATAACA<br>CTAGTGCTGTGAAGGAAGGAACTGCCATGCTGTTAGAACATCTTGCTGGGA<br>GCTTAGCATCAGCTATTCCTGTGAGCACACAACTAGATATTGCAGCTCAAC<br>ATCATCTCTTTATGATGGGTCGAAATGGGAGCAACATCAAACATATCATGC<br>AGAGAACAGGTGCTCAGATCCACTTTCCTGATCCCAGTAATCCACAAAAGA<br>AATCTACCGTCTACCTCCAGGGCACCATTGAGTCTGTCTGTCTTGCAAGGCA<br>ATATCTCATGGGTTGTCTTCCTCTTGTGTTGATGTTTGATATGAAGGAAGAA<br>ATTGAAGTAGATCCACAATTCATTGCGCAGTTGATGGAACAGCTTGATGTC<br>TTCATCAGTATTAAACCAAAGCCCAAACAGCCAAGCAAGTCTGTGATTGTG<br>AAAAGTGTTGAGCGAAATGCCTTAAATATGTATGAAGCAAGGAAATGTCTC<br>CTCGGACTTGAAAGCAGTGGGGTTACCATAGCAACCAGTCCATCCCCAGCA<br>TCCTGCCCTGCCGGCCTGGCATGTCCCAGCCTGGATATCTTAGCTTCAGCAG<br>GCCTTGGACTCACTGGACTAGGTCTTTTGGGACCCACCACCTTATCTCTGAA<br>CACTTCAACAACCCCAAACTCACTCTTGAATGCTCTTAATAGCTCAGTCAGT<br>CCTTTGCAAAGTCCAAGTTCTGGTACACCCAGCCCCACATTATGGGCACCC<br>CCACTTGCTAATACTTCAAGTGCCACAGGTTTTTCTGCTATACCACACCTTA<br>TGATTCCATCTACTGCCCAAGCCACATTAACTAATATTTTGTTGTCTGGAGT<br>GCCCACCTATGGGCACACAGCTCCATCTCCCCCTCCTGGCTTGACTCCTGTT<br>GATGTCCATATCAACAGTATGCAGACCGAAGGCAAAAAAATCTCTGCTGCT |

TABLE 5-continued

| | |
|---|---|
| | TTAAATGGACATGCACAGTCTCCAGATATAAAATATGGTGCAATATCCACT<br>TCATCACTTGGAGAAAAAGTGCTGAGTGCAAATCACGGGGATCCGTCCATC<br>CAGACAAGTGGGTCTGAGCAGACATCTCCCAAATCAAGCCCCACTGAAGGT<br>TGTAATGATGCTTTTGTTGAAGTAGGCATGCCTCGAAGTCCTTCCCATTCTG<br>GGAATGCTGGTGACTTGAAACAGATGATGTGTCCCTCCAAGGTTTCCTGTG<br>CCAAAAGGCAGACAGTGGAACTATTGCAAGGCACGAAAAACTCACACTTA<br>CACAGCACTGACAGGTTGCTCTCAGACCCTGAACTGAGTGCTACCGAAAGC<br>CCTTTGGCTGACAAGAAGGCTCCAGGGAGTGAGCGCGCTGCAGAGAGGGC<br>AGCAGCTGCCCAGCAAAACTCCGAAAGGGCCCACCTTGCTCCACGGTCATC<br>ATATGTCAACATGCAGGCATTTGACTATGAACAGAAGAAGCTATTAGCCAC<br>CAAAGCTATGTTAAAGAAACCAGTGGTGACGGAGGTCAGAACGCCCACAA<br>ATACCTGGAGTGGCCTGGGTTTTTCTAAATCCATGCCAGCTGAAACTATCA<br>AGGAGTTGAGAAGGGCCAATCATGTGTCCTATAAGCCCACAATGACAACC<br>ACTTATGAGGGCTCATCCATGTCCCTTTCACGGTCCAACAGTCGTGAGCACT<br>TGGGAGGTGGAAGCGAATCTGATAACTGGAGAGACCGAAATGGAATTGGA<br>CCTGGAAGTCATAGTGAATTTGCAGCTTCTATTGGCAGCCCTAAGCGTAAA<br>CAAAACAAATCAACGGAACACTATCTCAGCAGTAGCAATTACATGGACTGC<br>ATTTCCTCGCTGACAGGAAGCAATGGCTGTAACTTAAATAGCTCTTTCAAA<br>GGTTCTGACCTCCCTGAGCTCTTCAGCAAACTGGGCCTGGGCAAATACACA<br>GATGTTTTCCAGCAACAAGAGATCGATCTTCAGACATTCCTCACTCTCACA<br>GATCAGGATCTGAAGGAGCTGGGAATAACTACTTTTGGTGCCAGGAGGAA<br>AATGCTGCTTGCAATTTCAGAACTAAATAAAAACCGAAGAAAGCTTTTTGA<br>ATCGCCAAATGCACGCACCTCTTTCCTGGAAGGTGGAGCGAGTGGAAGGCT<br>ACCCCGTCAGTATCACTCAGACATTGCTAGTGTCAGTGGCCGCTGGTAG |
| FGFR2-CASP7<br>(3213 base pairs)<br>(SEQ ID NO: 37) | >ATGGTCAGCTGGGGTCGTTTCATCTGCCTGGTCGTGGTCACCATGGCAACC<br>TTGTCCCTGGCCCGGCCCTCCTTCAGTTTAGTTGAGGATACCACATTAGAGC<br>CAGAAGAGCCACCAACCAAATACCAAATCTCTCAACCAGAAGTGTACGTG<br>GCTGCGCCAGGGGAGTCGCTAGAGGTGCGCTGCCTGTTGAAAGATGCCGCC<br>GTGATCAGTTGGACTAAGGATGGGGTGCACTTGGGGCCCAACAATAGGAC<br>AGTGCTTATTGGGGAGTACTTGCAGATAAAGGGCGCCACGCCTAGAGACTC<br>CGGCCTCTATGCTTGTACTGCCAGTAGGACTGTAGACAGTGAAACTTGGTA<br>CTTCATGGTGAATGTCACAGATGCCATCTCATCCGGAGATGATGAGGATGA<br>CACCGATGGTGCGGAAGATTTTGTCAGTGAGAACAGTAACAACAAGAGAG<br>CACCATACTGGACCAACACAGAAAAGATGGAAAAGCGGCTCCATGCTGTG<br>CCTGCGGCCAACACTGTCAAGTTTCGCTGCCCAGCCGGGGGGAACCCAATG<br>CCAACCATGCGGTGGCTGAAAAACGGGAAGGAGTTTAAGCAGGAGCATCG<br>CATTGGAGGCTACAAGGTACGAAACCAGCACTGGAGCCTCATTATGGAAA<br>GTGTGGTCCCATCTGACAAGGGAAATTATACCTGTGTAGTGGAGAATGAAT<br>ACGGGTCCATCAATCACACGTACCACCTGGATGTTGTGGAGCGATCGCCTC<br>ACCGGCCCATCCTCCAAGCCGGACTGCCGGCAAATGCCTCCACAGTGGTCG<br>GAGGAGACGTAGAGTTTGTCTGCAAGGTTTACAGTGATGCCCAGCCCCACA<br>TCCAGTGGATCAAGCACGTGGAAAAGAACGGCAGTAAATACGGGCCCGAC<br>GGGCTGCCCTACCTCAAGGTTCTCAAGGCCGCCGGTGTTAACACCACGGAC<br>AAAGAGATTGAGGTTCTCTATATTCGGAATGTAACTTTTGAGGACGCTGGG<br>GAATATACGTGCTTGGCGGGTAATTCTATTGGGATATCCTTTCACTCTGCAT<br>GGTTGACAGTTCTGCCAGCGCCTGGAAGAGAAAAGGAGATTACAGCTTCCC<br>CAGACTACCTGGAGATAGCCATTTACTGCATAGGGGTCTTCTTAATCGCCT<br>GTATGGTGGTAACAGTCATCCTGTGCCGAATGAAGAACACGACCAAGAAG<br>CCAGACTTCAGCAGCCAGCCGGCTGTGCACAAGCTGACCAAACGTATCCCC<br>CTGCGGAGACAGGTAACAGTTTCGGCTGAGTCCAGCTCCTCCATGAACTCC<br>AACACCCCGCTGGTGAGGATAACAACACGCCTCTCTTCAACGGCAGACACC<br>CCCATGCTGGCAGGGGTCTCCGAGTATGAACTTCCAGAGGACCCAAAATGG<br>GAGTTTCCAAGAGATAAGCTGACACTGGGCAAGCCCCTGGGAGAAGGTTG<br>CTTTGGGCAAGTGGTCATGGCGGAAGCAGTGGGAATTGACAAAGACAAGC<br>CCAAGGAGGCGGTCACCGTGGCCGTGAAGATGTTGAAAGATGATGCCACA<br>GAGAAAGACCTTTCTGATCTGGTGTCAGAGATGGAGATGATGAAGATGATT<br>GGGAAACACAAGAATATCATAAATCTTCTTGGAGCCTGCACACAGGATGG<br>GCCTCTCTATGTCATAGTTGAGTATGCCTCTAAAGGCAACCTCCGAGAATA<br>CCTCCGAGCCCGGAGGCCACCCGGGATGGAGTACTCCTATGACATTAACCG<br>TGTTCCTGAGGAGCAGATGACCTTCAAGGACTTGGTGTCATGCACCTACCA<br>GCTGGCCAGAGGCATGGAGTACTTGGCTTCCCAAAAATGTATTCATCGAGA<br>TTTAGCAGCCAGAAATGTTTTGGTAACAGAAAACAATGTGATGAAAATAGC<br>AGACTTTGGACTCGCCAGAGATATCAACAATATAGACTATTACAAAAAGAC<br>CACCAATGGGCGGCTTCCAGTCAAGTGGATGGCTCCAGAAGCCCTGTTTGA<br>TAGAGTATACACTCATCAGAGTGATGTCTGGTCCTTCGGGGTGTTAATGTG<br>GGAGATCTTCACTTTAGGGGGCTCGCCCTACCCAGGGATTCCCGTGGAGGA<br>ACTTTTTAAGCTGCTGAAGGAAGGACACAGAATGGATAAGCCAGCCAACT<br>GCACCAACGAACTGTACATGATGATGAGGGACTGTTGGCATGCAGTGCCCT<br>CCCAGAGACCAACGTTCAAGCAGTTGGTAGAAGACTTGGATCGAATTCTCA<br>CTCTCACAACCAATGAGATGGCAGATGATCAGGGCTGTATTGAAGAGCAG<br>GGGGTTGAGGATTCAGCAAATGAAGATTCAGTGGATGCTAAGCCAGACCG<br>GTCCTCGTTTGTACCGTCCCTCTTCAGTAAGAAGAAGAAAAATGTCACCAT<br>GCGATCCATCAAGACCACCCGGGACCGAGTGCCTACATATCAGTACAACAT<br>GAATTTTGAAAAGCTGGGCAAATGCATCATAATAAACAACAAGAACTTTGA<br>TAAAGTGACAGGTATGGGCGTTCGAAACGGAACAGACAAAGATGCCGAGG<br>CGCTCTTCAAGTGCTTCCGAAGCCTGGGTTTTGACGTGATTGTCTATAATGA<br>CTGCTCTTGTGCCAAGATGCAAGATCTGCTTAAAAAAGCTTCTGAAGAGGA<br>CCATACAAATGCCGCCTGCTTCGCCTGCATCCTCTTAAGCCATGGAGAAGA<br>AAATGTAATTTATGGGAAAGATGGTGTCACACCAATAAAGGATTTGACAGC |

TABLE 5-continued

| |
|---|
| CCACTTTAGGGGGGATAGATGCAAAACCCTTTTAGAGAAACCCAAACTCTT<br>CTTCATTCAGGCTTGCCGAGGGACCGAGCTTGATGATGGCATCCAGGCCGA<br>CTCGGGGCCCATCAATGACACAGATGCTAATCCTCGATACAAGATCCCAGT<br>GGAAGCTGACTTCCTCTTCGCCTATTCCACGGTTCCAGGCTATTACTCGTGG<br>AGGAGCCCAGGAAGAGGCTCCTGGTTTGTGCAAGCCCTCTGCTCCATCCTG<br>GAGGAGCACGGAAAAGACCTGGAAATCATGCAGATCCTCACCAGGGTGAA<br>TGACAGAGTTGCCAGGCACTTTGAGTCTCAGTCTGATGACCCACACTTCCA<br>TGAGAAGAAGCAGATCCCCTGTGTGGTCTCCATGCTCACCAAGGAACTCTA<br>CTTCAGTCAATAG |

EXAMPLES

These examples are provided for illustrative purposes only and not to limit the scope of the claims provided herein.

Example 1: Phase 2, Multi Center, Open-Label Study (NCT02365597)

A Phase 2, multicenter, open-label study was conducted to evaluate the efficacy and safety of erdafitinib in subjects with metastatic or surgically unresectable urothelial cancer harboring select FGFR genetic alterations (FGFR translocations or mutations).

The study comprises a Screening Phase (molecular screening at any time prior to first dose and study screening within 30 days of first dose), a treatment phase, and a post-treatment follow-up phase. The treatment phase comprises the period from first dose until the end-of-treatment visit. The follow-up phase extends until the subject has died, withdraws consent, is lost to follow-up, or the end of study, whichever comes first.

Study treatment was administered on 28-day cycles. Prior to interim analysis 1, there were 2 treatment regimens. Patients were randomized 1:1 to 28-day cycles to the following 2 regimens until a regimen was selected for further study: Regimen 1 (10 mg once daily intermittent (7 days on/7 days); Regimen 2 (6 mg once daily continuous). Randomization was stratified according to performance status (0 to 1 vs. 2), hemoglobin value (<10 vs. ≥10 g per dl), FGFR alteration type (mutation vs. fusion), prior treatment status (chemotherapy-resistant vs. chemotherapy naïve), and disease distribution (presence or absence of visceral [liver, lung, bone]metastases). Starting dose selection was based on phase 1 efficacy and tolerability.

Based on interim analysis and pharmacokinetic-pharmacodynamic modeling of serum phosphate levels, starting dose was increased to 8 mg per day continuous (Regimen 3). Thus, after interim analysis, this became a single-arm study. Dosing was further individualized through pharmacodynamically-guided uptitration to 9 mg per day in patients who did not reach target serum phosphate level (≥5.5 mg per dl was associated with improved response rate in phase 1) by day 14 and in whom no treatment-related adverse events were observed. Treatment continued until disease progression or unacceptable adverse event(s) per investigator. Patients with investigator-assessed disease progression could continue erdafitinib at the discretion of the investigator and sponsor. See FIG. 1 for the Phase 2 study scheme.

Objectives

Primary Objective

- To evaluate the objective response rate (complete response [CR]+ partial response [PR]) of the selected dose regimen in subjects with metastatic or surgically unresectable urothelial cancers that harbor specific FGFR genomic alterations.

Secondary Objectives

- To evaluate the objective response rate of the selected dose regimen in chemo-refractory subjects
- To evaluate progression-free survival (PFS), duration of response, and overall survival of the selected dose regimen in all and chemo-refractory subjects
- To evaluate the response rate in biomarker-specific subgroups (translocations versus mutations) with the selected dose regimen
- To evaluate the objective response rate, PFS, duration of response, and overall survival of the other dose regimens tested
- To evaluate the safety and pharmacokinetics of erdafitinib of all dose regimens Patients Included patients were adults with measurable urothelial cancer per Response Evaluation Criteria in Solid Tumors version 1.1.

Patients were required to have at least 1 FGFR2/FGFR3 mutation or fusion per central lab testing of RNA from formalin-fixed, paraffin-embedded tumor samples, using a custom reverse transcriptase polymerase chain reaction assay.

Patients had progressed during or following at least 1 line of prior systemic chemotherapy or within 12 months of receiving neoadjuvant or adjuvant chemotherapy.

Chemotherapy-naïve patients who were ineligible for cisplatin per protocol criteria were allowed. Ineligibility for cisplatin was based on impaired renal function, defined as 1) glomerular filtration rate <60 mL/min/1.73 $m^2$ by 24-hour urine measurement; 2) calculated by the Cockcroft-Gault equation; or 3) grade 2 or higher peripheral neuropathy (Common Terminology Criteria for Adverse Events [CTCAE] version 4.0 (National Cancer Institute. CTCAE v4.0. NCI, NIH, DHHS. May 29, 2009. NIH publication #09-7473: 2009.).

Eastern Cooperative Oncology Group (ECOG) performance status (five-point scale in which higher numbers reflect greater disability) 0-2 was required.

There was no limit on the number of prior treatment lines.

Prior immunotherapy (e.g., treatment with an immune checkpoint inhibitor) was allowed.

Patients were required to have adequate bone marrow, liver and renal (creatinine clearance ≥40 mL/min) function.

Patients with phosphate levels persistently above upper limit of normal despite medical management, uncontrolled cardiovascular disease, brain metastases, known hepatitis B or C, or known HIV infection were excluded.

Assessments

Patients were assessed for efficacy per RECIST v.1.1 using computed tomography or magnetic resonance imaging scan of chest, abdomen, and pelvis during screening, once every 6 weeks for the first 3 months, once every 12 weeks for the next 9 months, then once every 4 to 6 months until progression. All objective responses required confirmation by an additional investigator assessment within 4 to 6 weeks of first assessment. Disease evaluations for regimen 3 were also performed by an independent radiographic review committee. Patients were contacted every 12 weeks for survival assessment.

Safety was evaluated based on clinical laboratory tests, physical exams, electrocardiograms, and ophthalmology examinations. Adverse events and abnormalities were assessed by investigator and graded per NCI CTCAE v.4.0

End Points

The primary end point of this study is Objective Response Rate to the selected regimen (Regimen 3).

Secondary end points include progression-free survival (PFS), response duration, Overall Survival, safety, response rate in biomarker-specific subgroups, and pharmacokinetics.

Statistical Analysis

The study was designed to enroll 180 patients with specified FGFR alterations. Of these, ≥88 were required in the selected regimen. Primary hypothesis was that objective response rate (ORR) in regimen 3 would be >25%. The study had an 85% power to reject the null hypothesis that ORR was ≤25%, with one-sided a of 0.025, given true response rate of 42%. Responses were assessed by investigators and an independent radiological review committee. Progression-free survival and overall survival were estimated using Kaplan-Meier product limit method. Data from patients who were progression free and alive or with unknown status were censored at last tumor assessment. Efficacy end points were analysed at primary analysis cutoff.

Results

Patients 2214 patients were assessed for eligibility. Of 210 eligible/treated patients, 33 were enrolled in regimen 1, 78 in regimen 2, and 99 in the selected phase 2 dose regimen, regimen 3.

Among patients treated with regimen 3, at the cutoff date for primary analysis and after 40 deaths, median survival follow-up time was 11.0 months (interquartile range, 0.7+ to 17.4 [95% confidence interval (CI), 9.1 to 12.2]). Median number of monthly cycles received was 5.0 (range, 1 to 18); median treatment duration was 5.3 months. In regimen 3, 41 of 99 patients were uptitrated to 9 mg per day erdafitinib; 13 patients continued treatment for at least 4 weeks beyond progression, as allowed per protocol.

Among patients treated with regimen 1 or 2, at the cutoff date for the primary analysis, the median survival follow-up time was 22.9 months in the group receiving regimen 1 (interquartile range, 1.7+ to 25.3+ [95% CI, 20.5 to 24.5]) and 18.5 months (interquartile range, 0.4+ to 21.6 [95% CI, 15.0 to 19.4) in the group receiving regimen 2. The median numbers of cycles in regimens 1 and 2 were 5.0 (range, 1 to 25) and 4.5 (range, 1 to 22), respectively. Median treatment durations were 4.4 and 3.9 months in regimens 1 and 2, respectively.

Demographic and baseline disease characteristics of patients in regimens 1 through 3 are presented in Table 6.

TABLE 6

Demographic and Baseline Disease Characteristics

| | Regimen 1 10 mg intermittent dose (n = 33) | Regimen 2 6 mg continuous dose (n = 78) | Regimen 3 8 mg continuous dose (n = 99) |
|---|---|---|---|
| Age (year), median (range) | 68 (53-88) | 65 (42-88) | 68 (36-87) |
| Sex | | | |
| Male | 22 (67) | 54 (69) | 76 (77) |
| Female | 11 (33) | 24 (31) | 23 (23) |
| ECOG performance status | | | |
| 0 | 11 (33) | 22 (28) | 50 (51) |
| 1 | 15 (46) | 41 (53) | 42 (42) |
| 2 | 7 (21) | 15 (19) | 7 (7) |
| Pretreatment | | | |
| Chemotherapy-resistant[b] | 29 (88) | 73 (94) | 87 (88) |
| Chemotherapy-naïve[c] | 4 (12) | 5 (6) | 12 (12) |
| Prior immunotherapy | 3 (9) | 8 (10) | 22 (22) |
| Number of lines of prior treatment | | | |
| 0 | 3 (9) | 5 (6) | 11 (11) |
| 1 | 13 (39) | 35 (45) | 45 (46) |
| 2 | 12 (36) | 24 (31) | 29 (29) |
| 3 | 4 (12) | 12 (15) | 10 (10) |
| >3 | 1 (3) | 2 (3) | 4 (4) |
| Visceral metastases | | | |
| Present* | 24 (73) | 59 (76) | 78 (79) |
| Bone | 6 (18) | 15 (19) | 21 (21) |
| Liver | 11 (33) | 25 (32) | 20 (20) |
| Lung | 15 (46) | 41 (53) | 57 (58) |
| Absent | 9 (27) | 19 (24) | 21 (21) |
| Hemoglobin level | | | |
| ≥10 g/dl | 29 (88) | 62 (79) | 84 (85) |
| <10 g/dl | 4 (12) | 16 (21) | 15 (15) |
| Tumor Location | | | |
| Upper tract | 11 (33) | 22 (28) | 23 (23) |
| Lower tract | 22 (67) | 56 (72) | 76 (77) |
| Creatinine clearance rate | | | |
| <60 mL/min | 12 (36) | 41 (53) | 52 (53) |
| ≥60 mL/min | 21 (64) | 37 (47) | 47 (47) |
| FGFR alterations[d] | | | |
| FGFR2 or FGFR3 fusion | | | |
| FGFR2-BICC1 | 3 (9) | 12 (15) | 25 (25) |
| FGFR2-CASP7 | 0 | 1 (1) | 2 (2) |
| FGFR3-BAIAP 2L1 | 0 | 1 (1) | 3 (3) |
| FGFR3-TACC3 V1 | 1 (3) | 1 (1) | 1 (1) |
| FGFR3-TACC3 V3 | 2 (6) | 7 (9) | 11 (11) |
| FGFR2-BICC1/FGFR2-CASP7 | 0 | 0 | 6 (6) |
| FGFR2-CASP7/FGFR3-BAIAP2L1 | 0 | 1 (1) | 0 |
| FGFR2-CASP7/FGFR3-TACC3 V1 | 0 | 1 (1) | 0 |
| FGFR2-CASP7/FGFR3-TACC3 V3 | 0 | 0 | 1 (1) |
| FGFR3 mutation | 0 | 0 | 1 (1) |
| FGFR3 G370C | 27 (82) | 62 (80) | 74 (75) |
| FGFR3 R248C | 7 (21) | 11 (14) | 4 (4) |
| FGFR3 S249C | 5 (15) | 14 (18) | 13 (13) |
| FGFR3 Y373C | 8 (24) | 20 (26) | 45 (46) |
| FGFR3 G370C and FGFR3 S249C | 4 (12) | 15 (19) | 12 (12) |
| FGFR3 R48C and FGFR3 Y373C | 1 (3) | 1 (1) | 0 |
| FGFR3 S249C and FGFR3 Y373C | 1 (3) | 1 (1) | 0 |
| FGFR2/3 fusions and mutations | 1 (3) | 0 | 0 |
| FGFR3 G370C/FGFR2-BICC1 | 3 (9) | 4 (5) | 0 |
| FGFR3 G370C/FGFR3-TACC3 V1 | 0 | 1 (1) | 0 |
| FGFR3 R248C/FGFR3-TACC3 V1 | 0 | 1 (1) | 0 |
| FGFR3 S249C/FGFR3-BAIAP2L1 | 1 (3) | 1 (1) | 0 |

TABLE 6-continued

Demographic and Baseline Disease Characteristics

| | Regimen 1 10 mg intermittent dose (n = 33) | Regimen 2 6 mg continuous dose (n = 78) | Regimen 3 8 mg continuous dose (n = 99) |
|---|---|---|---|
| FGFR3 R248C & S249/ FGFR3-TACC3 V1 | 1 (3) | 0 | 0 |
| FGFR3 S249C & Y373C/FGFR2- | 0 | 1 (1) | 0 |
| CASP7/FGFR3- BAIAP2L1/FGFR3-TACC3 V1/FGFR3 TACC3 V3 | 1(3) | 0 | 0 |

All values are n (%) unless noted.

*Patients could have more than one visceral metastatic site.

[b]Chemotherapy-resistant patients were those who had progressed during or following ≥1 line of prior systemic chemotherapy or within 12 months of adjuvant or neoadjuvant chemotherapy.

[c]Chemotherapy-naïve patients were those who were ineligible for cisplatin. Ineligibility for cisplatin was based on impaired renal function defined as 1) glomerular filtration rate <60 mL/min/1.73 m2 by 24-hour urine measurement; 2) calculated by Cockcroft-Gault; or 3) grade 2 or higher peripheral neuropathy (CTCAE version 4.0).

[d]Patients could have more than 1 FGFR alteration.

Across all regimens, 184 patients had received first-line platinum-based chemotherapy, 83 had received second-line chemotherapy, and 24 had received third-line chemotherapy before study enrolment. Across all regimens, the best ORRs per investigator assessment were 35% (33 of 94) for first-line gemcitabine plus cisplatin; 25% (15 of 59) for first-line gemcitabine plus carboplatin; 23% (5/22) for first-line methotrexate, vinblastine, doxorubicin, and cisplatin (MVAC); 17% (8/46) for second-line docetaxel, vinflunine, or paclitaxel; and 15% (3/20) for third-line docetaxel, vinflunine, or paclitaxel.

Primary End Point

Figure 2:
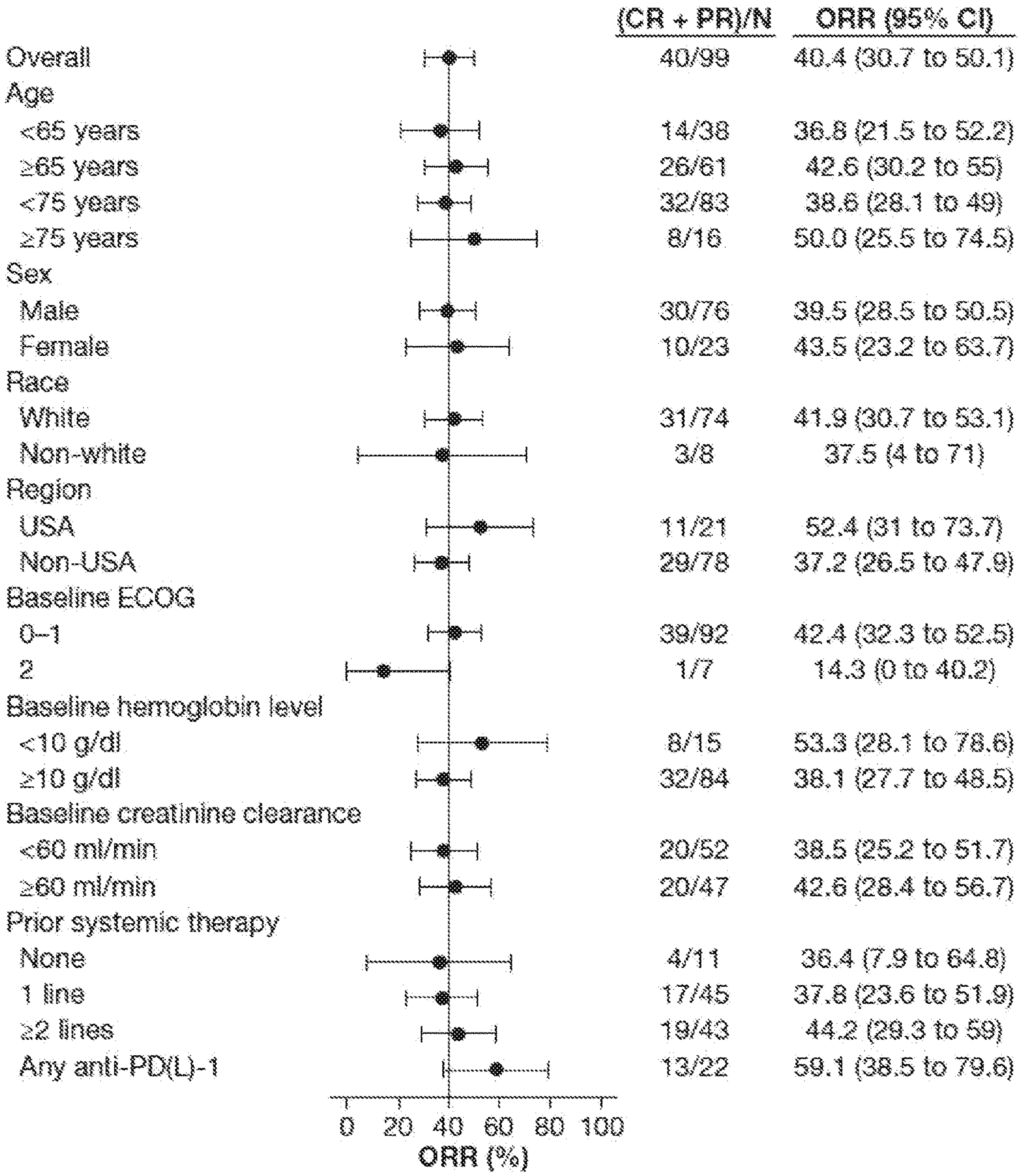
FIG. 2 shows patient responses to treatment with 8 mg per day continuous erdafitinib (Regimen 3): Objective response rates (ORRs) among patient subgroups.
Figure 3A:
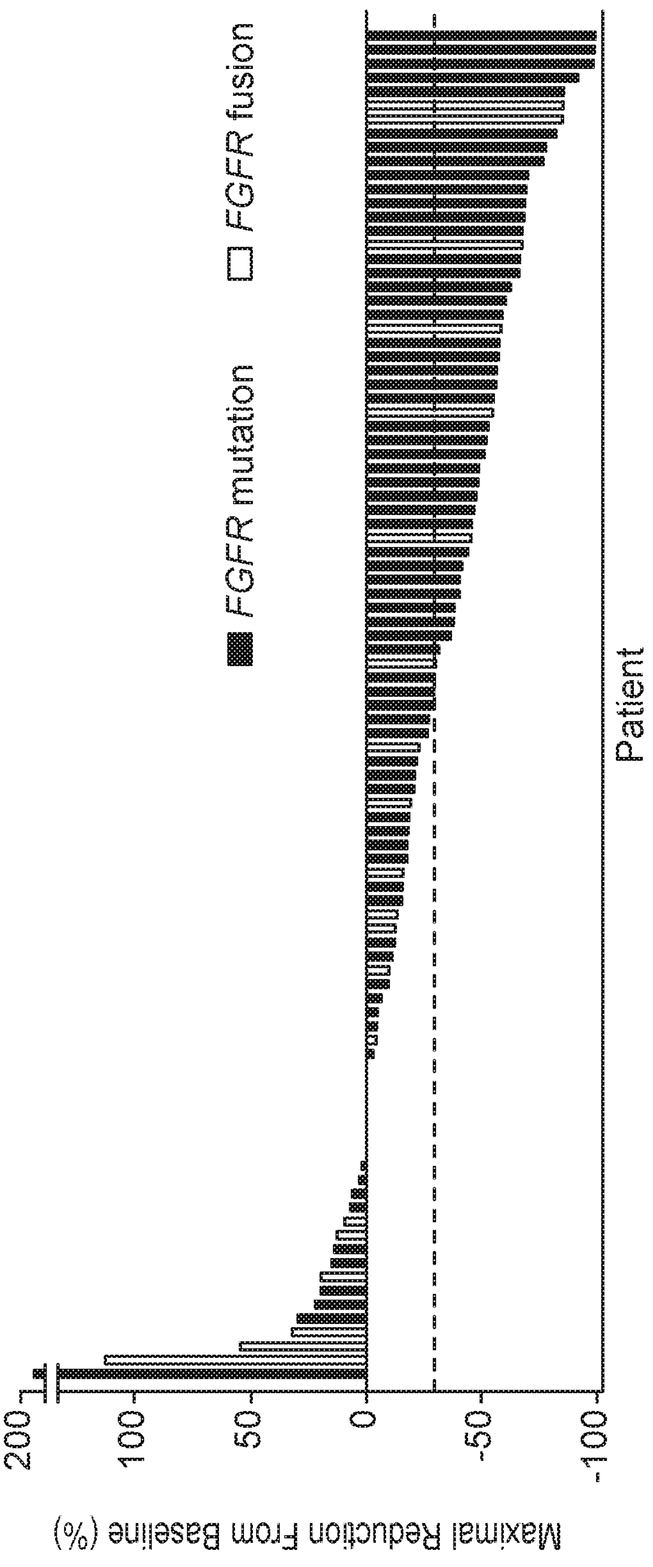
FIGS. 3A-C, shows waterfall plots of reduction in the sum of target lesion diameters after treatment with erdafitinib. Reductions in patients treated with (FIG. 3A) 8 mg per day continuous erdafitinib (regimen 3), (FIG. 3B) 10 mg intermittent erdafitinib (regimen 1), and (FIG. 3C) 6 mg per day continuous erdafitinib (regimen 2) among all treated patients.
Figure 3B:
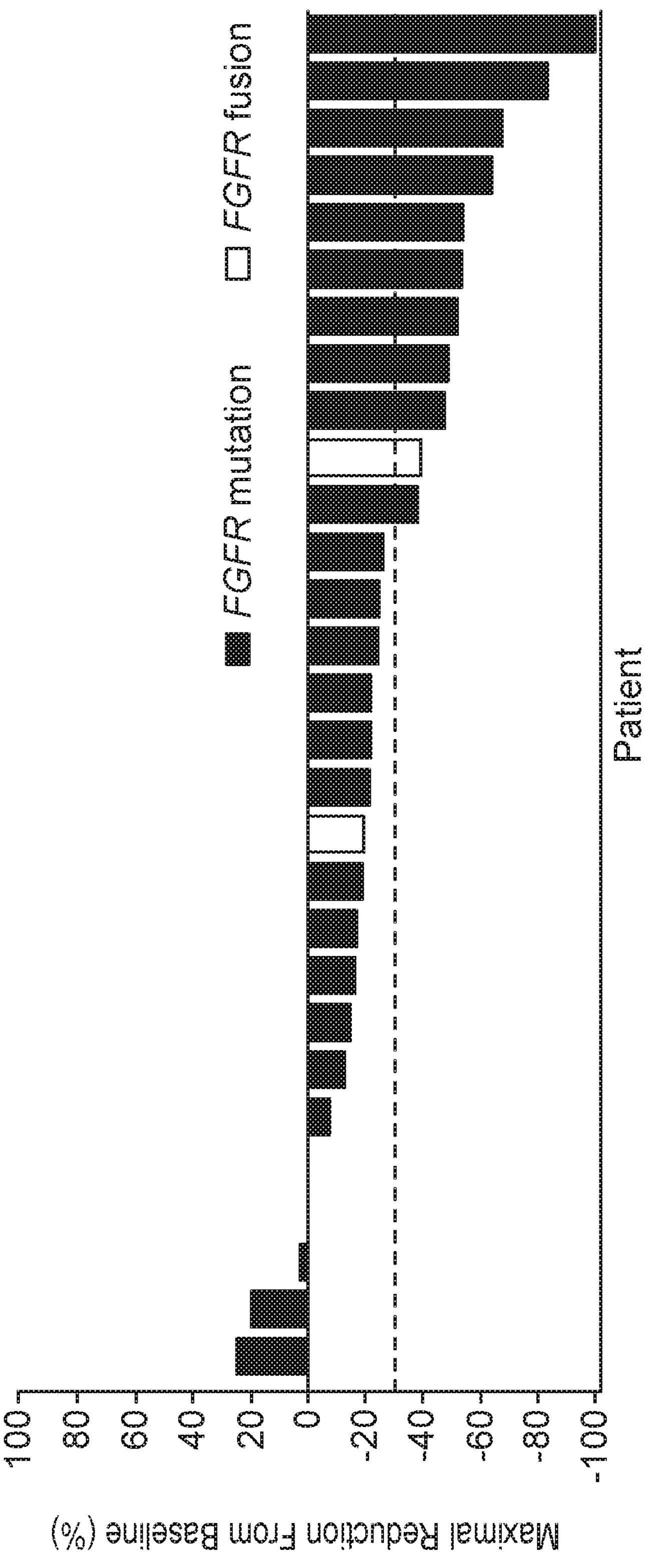
Figure 3C:
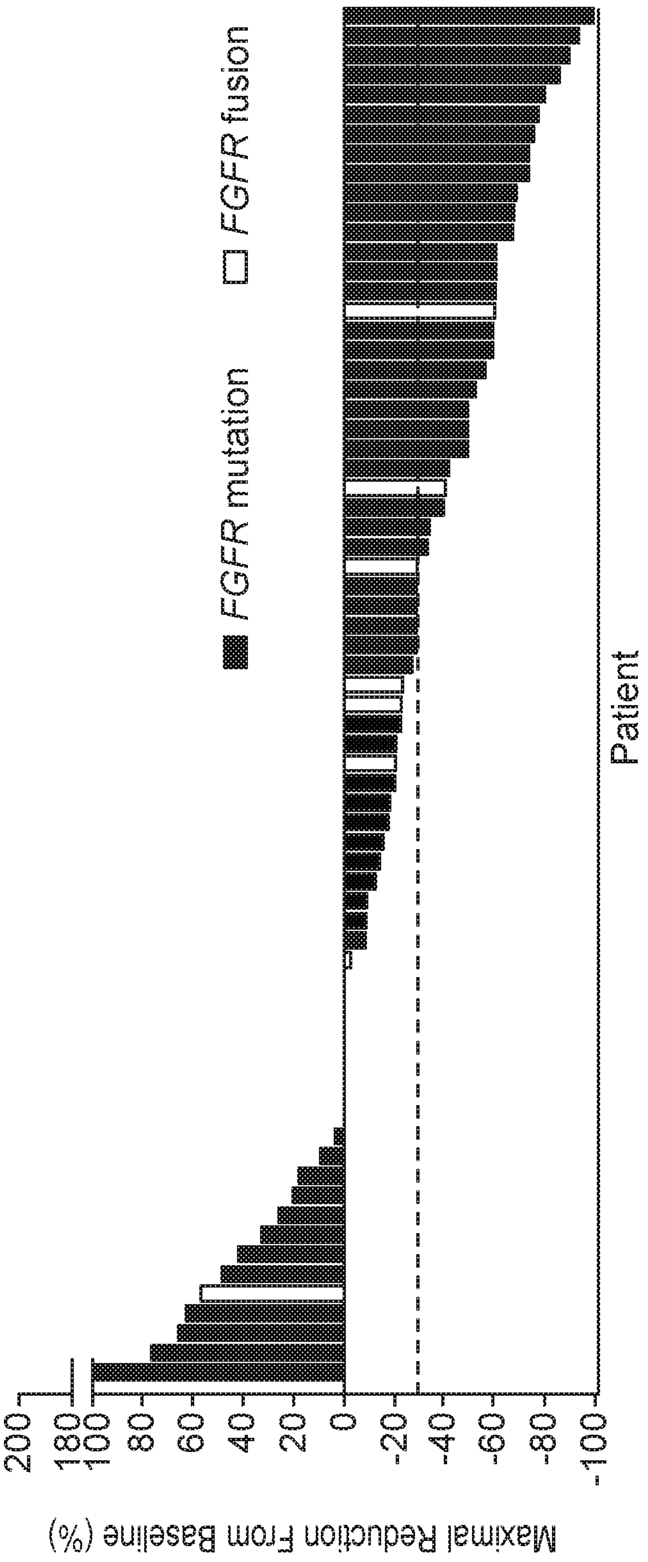

The confirmed ORR (40.4%, with a two-sided 95% CI of 30.7% to 50.1%) per investigator assessment and time to response among patients treated with regimen 3 are presented in Table 7. Because lower boundary of the confidence interval was >25%, the primary end point was achieved. An additional 39 (39%) patients had stable disease for ≥1 disease evaluation assessment (>36 days). Two patients had no postbaseline disease evaluations. ORRs were similar regardless of prior chemotherapy, number of prior treatment lines, presence of visceral metastases, or baseline characteristics such as age, sex, hemoglobin level, or renal function (Table 7, FIG. 2). Seventy-five (77%) of 97 patients with ≥1 postbaseline disease evaluation had reduction in sum of target lesion diameters, and 48 (49%) had maximum tumor reduction between 30% and 100% (FIG. 3A). ORR in regimen 3 per independent radiographic review was 34.3% (95% CI, 25% to 43.7%).

TABLE 7

Antitumor Activity of 3 Dose Regimens of Erdafitinib

| | Regimen 1 10 mg intermittent dose (n = 33) | Regimen 2 6 mg continuous dose (n = 78) | Regimen 3 8 mg continuous dose (n = 99) | (95% CI) |
|---|---|---|---|---|
| Patients—no. | — | — | 99 | |
| Response per investigator assessment*—no. (%) | | | | |
| Objective response rate | 7 (21) | 27 (35) | 40 (40.4) | (30.7 to 50.1) |
| Complete response | 1 (3) | 3 (4) | 3 (3.0) | |
| Partial response | 6 (18) | 24 (31) | 37 (37.4) | |
| Stable disease | 18 (55) | 30 (39) | 39 (39.4) | |
| Progressive disease | 6 (18) | 16 (21) | 18 (18.2) | |
| Not evaluable or unknown | 2 (6) | 5(6) | 2 (2.0) | |
| Median time to response—mo | 1.4 | 1.4 | 1.4 | |
| Median duration of response—mo | 13.4 | 4.9 | 5.6 | (4.2 to 7.2) |
| Patients—no. | — | — | 99 | |
| Response per independent radiographic review committee—no. (%) (performed only for Regimen 3) | | | | |
| Objective response rate | — | — | 34 (34.3) | (25.0 to 43.7) |
| Complete response rate | — | — | 3 (3.0) | |
| Partial response | — | — | 31 (31.3) | |
| Objective response rate per investigator assessment among patient subgroups—no. (%) | | | | |
| Chemotherapy-naïve | 1/4 (25) | 0/5 (0) | 5/12 (41.7) | |
| Progressed or relapsed after chemotherapy | 6/29 (21) | 27/73 (37) | 35/87 (40.2) | |
| Patients with prior anti-PD-(L)1 inhibitor | — | — | 13/22 (59.1) | |
| No. of lines of prior systemic therapy | | | | |
| 0 | — | — | 4/11 (36.4) | (7.9 to 64.8) |
| 1 | — | — | 17/45 (37.8) | (23.6 to 51.9) |
| 2 | — | — | 11/29 (37.9) | (20.3 to 55.6) |
| 3 | — | — | 6/10 (60.0) | (29.6 to 90.4) |
| >4 | — | — | 2/4 (50.0) | (1 to 99) |
| With visceral metastases | 7/24 (29) | 19/59 (32) | 30/78 (38.5) | (27.7 to 49.3) |
| Bone metastases | 1/6 (17) | 6/15 (40) | 7/22 (31.8) | (12.4 to 51.3) |
| Liver metastases | 3/11 (27) | 6/25 (24) | 7/20 (35.0) | (14.1 to 55.9) |
| Lung metastases | 4/15 (27) | 17/41 (41) | 23/57 (40.4) | (27.6 to 53.1) |
| Without visceral metastases | 0/9 (0) | 8/19 (42) | 10/21 (47.6) | (26.3 to 69) |

TABLE 7-continued

| Antitumor Activity of 3 Dose Regimens of Erdafitinib | | | | |
|---|---|---|---|---|
| | Regimen 1 10 mg inter-mittent dose (n = 33) | Regimen 2 6 mg con-tinuous dose (n = 78) | Regimen 3 8 mg continuous dose (n = 99) | (95% CI) |
| Lymph node metastases only | 0/4 (0) | 6/9 (67) | 4/12 (33.3) | (6.7 to 60) |
| Upper tract disease† | 5/11 (46) | 5/22 (23) | 10/23 (43.5) | (23.2 to 63.7) |
| Lower tract disease‡ | 2/22 (9) | 22/56 (39) | 30/76 (39.5) | (28.5 to 50.5) |
| Dose individualization | | | | |
| 8 mg non-uptitrated continuous dose regimen | — | — | 20/58 (34.5) | (22.3 to 46.7) |
| Patients—no. | — | — | 99 | |
| 8 mg uptitrated to 9 mg continuous dose regimen | — | — | 20/41 (48.8) | (33.5 to 64.1) |
| With FGFR3 mutations | 6/27 (22) | 22/62 (36) | 36/74 (48.6) | (37.3 to 60.0) |
| With FGFR2/3 fusions | 0/3 (0) | 2/12 (17) | 4/25 (16.0) | (1.6 to 30.4) |

*Confirmed with second scan at least 6 weeks after the initial observation of response.
†Upper tract included renal pelvis and ureter.
‡Lower tract included bladder, urethra, and prostatic urethra.

The ORR among patients treated on regimen 3 who had FGFR mutations (n=74) 10C-34, 1,M was 48.6% (Table 7). An additional 26 patients had stable disease for median 3.7 months (range, 0+ to 13.6 months). Responses were not affected by the particular mutation. Among 25 patients in regimen 3 with FGFR fusions, the ORR was 16.0% (Table 7). FGFR3-TACC3 V1 was the most common fusion (n=11; Table 6); and four (36.4%) of these patients responded.

In regimen 3, 22 patients received immunotherapy before study enrolment (Table 6); confirmed ORR to erdafitinib was 59% among these patients. Exploratory analysis determined that only one of these 22 (5%) patients had responded to prior immunotherapy per investigator assessment.

The ORRs for regimens 1 and 2 are also presented in Table 7.

Of the 99 patients treated with regimen 3, 87 patients had disease that had progressed on or after at least one prior chemotherapy (chemotherapy-relapsed/refractory disease) and that had at least 1 of the following gene alterations: FGFR3 gene mutations (R248C, S249C, G370C, Y373C) or FGFR gene fusions (FGFR3-TACC3, FGFR3-BAIAP2L1, FGFR2-BICC1, FGFR2-CASP7), as determined by a clinical trial assay performed at a central laboratory (Table 6). Among this population, the median age was 67 years (range: 36 to 87 years), 79% were male, and 74% were Caucasian. Most patients (92%) had a baseline Eastern Cooperative Oncology Group (ECOG) performance status of 0 or 1. Three (3%) patients had disease progression following prior platinum-containing neoadjuvant or adjuvant therapy only. Eighty-four (97%) patients received at least one of cisplatin or carboplatin previously. Fifty-six percent of patients only received prior cisplatin-based regimens, 29% received only prior carboplatin-based regimens, and 10% received both cisplatin and carboplatin-based regimens. Twenty-four percent of patients had been treated with prior anti PD-L1/PD-1 therapy. Seventy-nine percent of patients had visceral metastases (bone, liver or lung).

Among the 87 chemotherapy-refractory patients in regimen 3, overall response rate as assessed by investigator was 40.2%; results for this population of patients are presented in Table 8A. Responders included patients who had previously not responded to anti PD-L1/PD-1 therapy. The ORR by FGFR alteration is presented in Table 9A.

TABLE 8A

| Efficacy Results for Chemotherapy-Refractory Patients in Regimen 3 (N = 87) | |
|---|---|
| Endpoint | Investigator assessment N = 87 |
| ORR (%) 95% CI (%) | 40.2 (29.9, 50.5) |
| Complete response (CR) (%) | 3.4 |
| Partial response (PR) (%) | 36.8 |
| Median DoR (months) 95% CI (months) | 5.55 (4.21, 7.00) |

ORR = CR + PR
CI = Confidence Interval

TABLE 9A

| Efficacy Results by FGFR Genetic Alteration for Chemotherapy-Refractory Patients in Regimen 3 | |
|---|---|
| | Investigator assessment |
| FGFR3 Point Mutation | N = 64 |
| ORR (%) 95% CI (%) | 48.4 (36.2, 60.7) |
| FGFR Fusion | N = 23 |
| ORR (%) 95% CI (%) | 17.4 (1.9, 32.9) |

ORR = CR + PR
CI = Confidence Interval

Among the 87 chemotherapy-relapsed/refractory patients in regimen 3, overall response rate as assessed by blinded independent review committee was 32.2%; results for this population of patients are presented in Table 8B. Responders included patients who had previously not responded to anti PD-L1/PD-1 therapy. The ORR by FGFR alteration is presented in Table 9B.

TABLE 8B

| Efficacy Results for Chemotherapy-Refractory Patients in Regimen 3 | |
|---|---|
| Endpoint | BIRC[a] assessment N = 87 |
| ORR (%) 95% CI (%) | 32.2 (22.4, 42.0) |
| Complete response (CR) (%) | 2.3 |
| Partial response (PR) (%) | 29.9 |
| Median DoR (months) 95% CI (months) | 5.4 (4.2, 6.9) |

[a]BIRC: Blinded Independent Review Committee
ORR = CR + PR
CI = Confidence Interval

TABLE 9B

| Efficacy Results by FGFR Genetic Alteration for Chemotherapy-Refractory Patients in Regimen 3 | |
|---|---|
| | BIRC[a] assessment |
| FGFR3 Point Mutation | N = 64 |
| ORR (%) 95% CI (%) | 40.6 (28.6, 52.7) |
| FGFR3 Fusion [b,c] | N = 18 |
| ORR (%) 95% CI (%) | 11.1 (0, 25.6) |
| FGFR2 Fusion [c] | N = 6 |
| ORR (%) | 0 |

[a]BIRC: Blinded Independent Review Committee

[b] Both responders had FGFR3-TACC3_VI fusion

TABLE 9B-continued

| Efficacy Results by FGFR Genetic Alteration for Chemotherapy-Refractory Patients in Regimen 3 | |
|---|---|
| | BIRC[a] assessment |

[c] One patient with a FGFR2-CASP7/FGFR3-TACC3_V3 fusion is reported in both FGFR2 fusion and FGFR3 fusion above
ORR = CR + PR
CI = Confidence Interval Overall Response, Duration of Response, Progression-Free Survival and Overall Survival by FGFR Alterations/Co-Alterations, for Chemotherapy-Relapsed/Refractory Subjects The best overall response, the duration of response, progression-free survival and overall survical divided by FGFR alterations is provided in Tables 10-13.

TABLE 10

Best Overall Response by FGFR Alterations (Mutually Exclusive)-Investigator Assessment; Treated Chemo Relapsed/Refractory Subjects

| | 8 mg QD | 6 mg QD | 10 mg 7 on/7 off | Total |
|---|---|---|---|---|
| Any FGFR alterations | | | | |
| Total number of subjects | 87 | 73 | 29 | 189 |
| Objective response rate (CR + PR) | 35 (40.2%) | 27 (37.0%) | 6 (20.7%) | 68 (36.0%) |
| 95% CI | (29.9%, 50.5%) | (25.9%, 48.1%) | (5.9%, 35.4%) | (29.1%, 42.8%) |
| Disease control rate (CR + PR + SD) | 69 (79.3%) | 55 (75.3%) | 23 (79.3%) | 147 (77.8%) |
| 95% CI | (70.8%, 87.8%) | (65.5%, 85.2%) | (64.6%, 94.1%) | (71.9%, 83.7%) |
| Best overall response | | | | |
| Confirmed complete response (CR) | 3 (3.4%) | 3 (4.1%) | 1 (3.4%) | 7 (3.7%) |
| Confirmed partial response (PR) | 32 (36.8%) | 24 (32.9%) | 5 (17.2%) | 61 (32.3%) |
| Stable disease (SD) | 34 (39.1%) | 28 (38.4%) | 17 (58.6%) | 79 (41.8%) |
| Progressive disease (PD) | 16 (18.4%) | 14 (19.2%) | 4 (13.8%) | 34 (18.0%) |
| Inevaluable | 2 (2.3%) | 4 (5.5%) | 2 (6.9%) | 8 (4.2%) |
| FGFR mutations (excluding fusions) | | | | |
| Total number of subjects | 64 | 59 | 24 | 147 |
| Objective response rate (CR + PR) | 31 (48.4%) | 22 (37.3%) | 5 (20.8%) | 58 (39.5%) |
| 95% CI | (36.2%, 60.7%) | (24.9%, 49.6%) | (4.6%, 37.1%) | (31.6%, 47.4%) |
| Disease control rate (CR + PR + SD) | 54 (84.4%) | 43 (72.9%) | 20 (83.3%) | 117 (79.6%) |
| 95% CI | (75.5%, 93.3%) | (61.5%, 84.2%) | (68.4%, 98.2%) | (73.1%, 86.1%) |
| Best overall response | | | | |
| Confirmed complete response (CR) | 3 (4.7%) | 2 (3.4%) | 1 (4.2%) | 6 (4.1%) |
| Confirmed partial response (PR) | 28 (43.8%) | 20 (33.9%) | 4 (16.7%) | 52 (35.4%) |
| Stable disease (SD) | 23 (35.9%) | 21 (35.6%) | 15 (62.5%) | 59 (40.1%) |
| Progressive disease (PD) | 9 (14.1%) | 14 (23.7%) | 2 (8.3%) | 25 (17.0%) |
| Inevaluable | 1 (1.6%) | 2 (3.4%) | 2 (8.3%) | 5 (3.4%) |
| Mutation: FGFR3-G370C/FGFR3-S249C | | | | |
| Total number of subjects | 0 | 1 | 1 | 2 |
| Objective response rate (CR + PR) | 0 | 0 | 1 (100.0%) | 1 (50.0%) |
| 95% CI | (NE, NE) | (NE, NE) | (100%, 100%) | (0%, 100%) |
| Disease control rate (CR + PR + SD) | 0 | 1 (100.0%) | 1 (100.0%) | 2 (100.0%) |
| 95% CI | (NE, NE) | (100%, 100%) | (100%, 100%) | (100%, 100%) |
| Best overall response | | | | |
| Confirmed complete response (CR) | 0 | 0 | 0 | 0 |
| Confirmed partial response (PR) | 0 | 0 | 1 (100.0%) | 1 (50.0%) |
| Stable disease (SD) | 0 | 1 (100.0%) | 0 | 1 (50.0%) |
| Progressive disease (PD) | 0 | 0 | 0 | 0 |
| Inevaluable | 0 | 0 | 0 | 0 |
| Mutation: FGFR3-R248C/FGFR3-Y373C | | | | |
| Total number of subjects | 0 | 1 | 1 | 2 |
| Objective response rate (CR + PR) | 0 | 1 (100.0%) | 1 (100.0%) | 2 (100.0%) |
| 95% CI | (NE, NE) | (100%, 100%) | (100%, 100%) | (100%, 100%) |
| Disease control rate (CR + PR + SD) | 0 | 1 (100.0%) | 1 (100.0%) | 2 (100.0%) |
| 95% CI | (NE, NE) | (100%, 100%) | (100%, 100%) | (100%, 100%) |

TABLE 10-continued

Best Overall Response by FGFR Alterations (Mutually Exclusive)-Investigator Assessment; Treated Chemo Relapsed/Refractory Subjects

| | 8 mg QD | 6 mg QD | 10 mg 7 on/7 off | Total |
|---|---|---|---|---|
| Best overall response | | | | |
| Confirmed complete response (CR) | 0 | 0 | 0 | 0 |
| Confirmed partial response (PR) | 0 | 1 (100.0%) | 1 (100.0%) | 2 (100.0%) |
| Stable disease (SD) | 0 | 0 | 0 | 0 |
| Progressive disease (PD) | 0 | 0 | 0 | 0 |
| Inevaluable | 0 | 0 | 0 | 0 |
| Mutation: FGFR3-S249C/FGFR3-Y373C | | | | |
| Total number of subjects | 0 | 0 | 1 | 1 |
| Objective response rate (CR + PR) | 0 | 0 | 0 | 0 |
| 95% CI | (NE, NE) | (NE, NE) | (NE, NE) | (NE, NE) |
| Disease control rate (CR + PR + SD) | 0 | 0 | 1 (100.0%) | 1 (100.0%) |
| 95% CI | (NE, NE) | (NE, NE) | (100%, 100%) | (100%, 100%) |
| Best overall response | | | | |
| Confirmed complete response (CR) | 0 | 0 | 0 | 0 |
| Confirmed partial response (PR) | 0 | 0 | 0 | 0 |
| Stable disease (SD) | 0 | 0 | 1 (100.0%) | 1 (100.0%) |
| Progressive disease (PD) | 0 | 0 | 0 | 0 |
| Inevaluable | 0 | 0 | 0 | 0 |
| FGFR fusions (excluding mutations) | | | | |
| Total number of subjects | 23 | 10 | 2 | 35 |
| Objective response rate (CR + PR) | 4 (17.4%) | 2 (20.0%) | 0 | 6 (17.1%) |
| 95% CI | (1.9%, 32.9%) | (0%, 44.8%) | (NE, NE) | (4.7%, 29.6%) |
| Disease control rate (CR + PR + SD) | 15 (65.2%) | 9 (90.0%) | 1 (50.0%) | 25 (71.4%) |
| 95% CI | (45.8%, 84.7%) | (71.4%, 100%) | (0%, 100%) | (56.5%, 86.4%) |
| Best overall response | | | | |
| Confirmed complete response (CR) | 0 | 0 | 0 | 0 |
| Confirmed partial response (PR) | 4 (17.4%) | 2 (20.0%) | 0 | 6 (17.1%) |
| Stable disease (SD) | 11 (47.8%) | 7 (70.0%) | 1 (50.0%) | 19 (54.3%) |
| Progressive disease (PD) | 7 (30.4%) | 0 | 1 (50.0%) | 8 (22.9%) |
| Inevaluable | 1 (4.3%) | 1 (10.0%) | 0 | 2 (5.7%) |
| Fusion: FGFR2-CASP7/FGFR3-BAIAP2L1 | | | | |
| Total number of subjects | 0 | 1 | 0 | 1 |
| Objective response rate (CR + PR) | 0 | 0 | 0 | 0 |
| 95% CI | (NE, NE) | (NE, NE) | (NE, NE) | (NE, NE) |
| Disease control rate (CR + PR + SD) | 0 | 1 (100.0%) | 0 | 1 (100.0%) |
| 95% CI | (NE, NE) | (100%, 100%) | (NE, NE) | (100%, 100%) |
| Best overall response | | | | |
| Confirmed complete response (CR) | 0 | 0 | 0 | 0 |
| Confirmed partial response (PR) | 0 | 0 | 0 | 0 |
| Stable disease (SD) | 0 | 1 (100.0%) | 0 | 1 (100.0%) |
| Progressive disease (PD) | 0 | 0 | 0 | 0 |
| Inevaluable | 0 | 0 | 0 | 0 |
| Fusion: FGFR2-CASP7/FGFR3-TACC3 V3 | | | | |
| Total number of subjects | 1 | 0 | 0 | 1 |
| Objective response rate (CR + PR) | 0 | 0 | 0 | 0 |
| 95% CI | (NE, NE) | (NE, NE) | (NE, NE) | (NE, NE) |
| Disease control rate (CR + PR + SD) | 0 | 0 | 0 | 0 |
| 95% CI | (NE, NE) | (NE, NE) | (NE, NE) | (NE, NE) |
| Best overall response | | | | |
| Confirmed complete response (CR) | 0 | 0 | 0 | 0 |
| Confirmed partial response (PR) | 0 | 0 | 0 | 0 |
| Stable disease (SD) | 0 | 0 | 0 | 0 |
| Progressive disease (PD) | 0 | 0 | 0 | 0 |
| Inevaluable | 1 (100.0%) | 0 | 0 | 1 (100.0%) |
| FGFR mutations and fusions | | | | |
| Total number of subjects | 0 | 4 | 3 | 7 |
| Objective response rate (CR + PR) | 0 | 3 (75.0%) | 1 (33.3%) | 4 (57.1%) |
| 95% CI | (NE, NE) | (32.6%, 100%) | (0%, 86.7%) | (20.5%, 93.8%) |
| Disease control rate (CR + PR + SD) | 0 | 3 (75.0%) | 2 (66.7%) | 5 (71.4%) |
| 95% CI | (NE, NE) | (32.6%, 100%) | (13.3%, 100%) | (38%, 100%) |
| Best overall response | | | | |
| Confirmed complete response (CR) | 0 | 1 (25.0%) | 0 | 1 (14.3%) |
| Confirmed partial response (PR) | 0 | 2 (50.0%) | 1 (33.3%) | 3 (42.9%) |

TABLE 10-continued

Best Overall Response by FGFR Alterations (Mutually Exclusive)-Investigator Assessment; Treated Chemo Relapsed/Refractory Subjects

| | 8 mg QD | 6 mg QD | 10 mg 7 on/7 off | Total |
|---|---|---|---|---|
| Stable disease (SD) | 0 | 0 | 1 (33.3%) | 1 (14.3%) |
| Progressive disease (PD) | 0 | 0 | 1 (33.3%) | 1 (14.3%) |
| Inevaluable | 0 | 1 (25.0%) | 0 | 1 (14.3%) |
| Mutation and fusion: FGFR3-G370C/FGFR2-BICC1 | | | | |
| Total number of subjects | 0 | 1 | 0 | 1 |
| Objective response rate (CR + PR) | 0 | 1 (100.0%) | 0 | 1 (100.0%) |
| 95% CI | (NE, NE) | (100%, 100%) | (NE, NE) | (100%, 100%) |
| Disease control rate (CR + PR + SD) | 0 | 1 (100.0%) | 0 | 1 (100.0%) |
| 95% CI | (NE, NE) | (100%, 100%) | (NE, NE) | (100%, 100%) |
| Best overall response | | | | |
| Confirmed complete response (CR) | 0 | 1 (100.0%) | 0 | 1 (100.0%) |
| Confirmed partial response (PR) | 0 | 0 | 0 | 0 |
| Stable disease (SD) | 0 | 0 | 0 | 0 |
| Progressive disease (PD) | 0 | 0 | 0 | 0 |
| Inevaluable | 0 | 0 | 0 | 0 |
| Mutation and fusion: FGFR3-G370C/FGFR3-TACC3 V1 | | | | |
| Total number of subjects | 0 | 1 | 0 | 1 |
| Objective response rate (CR + PR) | 0 | 1 (100.0%) | 0 | 1 (100.0%) |
| 95% CI | (NE, NE) | (100%, 100%) | (NE, NE) | (100%, 100%) |
| Disease control rate (CR + PR + SD) | 0 | 1 (100.0%) | 0 | 1 (100.0%) |
| 95% CI | (NE, NE) | (100%, 100%) | (NE, NE) | (100%, 100%) |
| Best overall response | | | | |
| Confirmed complete response (CR) | 0 | 0 | 0 | 0 |
| Confirmed partial response (PR) | 0 | 1 (100.0%) | 0 | 1 (100.0%) |
| Stable disease (SD) | 0 | 0 | 0 | 0 |
| Progressive disease (PD) | 0 | 0 | 0 | 0 |
| Inevaluable | 0 | 0 | 0 | 0 |
| Mutation and fusion: FGFR3-R248C/FGFR3-TACC3 V1 | | | | |
| Total number of subjects | 0 | 1 | 1 | 2 |
| Objective response rate (CR + PR) | 0 | 0 | 1 (100.0%) | 1 (50.0%) |
| 95% CI | (NE, NE) | (NE, NE) | (100%, 100%) | (0%, 100%) |
| Disease control rate (CR + PR + SD) | 0 | 0 | 1 (100.0%) | 1 (50.0%) |
| 95% CI | (NE, NE) | (NE, NE) | (100%, 100%) | (0%, 100%) |
| Best overall response | | | | |
| Confirmed complete response (CR) | 0 | 0 | 0 | 0 |
| Confirmed partial response (PR) | 0 | 0 | 1 (100.0%) | 1 (50.0%) |
| Stable disease (SD) | 0 | 0 | 0 | 0 |
| Progressive disease (PD) | 0 | 0 | 0 | 0 |
| Inevaluable | 0 | 1 (100.0%) | 0 | 1 (50.0%) |
| Mutation and fusion: FGFR3-S249C/FGFR3-BAIAP2L1 | | | | |
| Total number of subjects | 0 | 0 | 1 | 1 |
| Objective response rate (CR + PR) | 0 | 0 | 0 | 0 |
| 95% CI | (NE, NE) | (NE, NE) | (NE, NE) | (NE, NE) |
| Disease control rate (CR + PR + SD) | 0 | 0 | 0 | 0 |
| 95% CI | (NE, NE) | (NE, NE) | (NE, NE) | (NE, NE) |
| Best overall response | | | | |
| Confirmed complete response (CR) | 0 | 0 | 0 | 0 |
| Confirmed partial response (PR) | 0 | 0 | 0 | 0 |
| Stable disease (SD) | 0 | 0 | 0 | 0 |
| Progressive disease (PD) | 0 | 0 | 1 (100.0%) | 1 (100.0%) |
| Inevaluable | 0 | 0 | 0 | 0 |
| Mutation and fusion: FGFR3-R248C/FGFR3-S249C/FGFR3-TACC3 V1 | | | | |
| Total number of subjects | 0 | 1 | 0 | 1 |
| Objective response rate (CR + PR) | 0 | 1 (100.0%) | 0 | 1 (100.0%) |
| 95% CI | (NE, NE) | (100%, 100%) | (NE, NE) | (100%, 100%) |
| Disease control rate (CR + PR + SD) | 0 | 1 (100.0%) | 0 | 1 (100.0%) |
| 95% CI | (NE, NE) | (100%, 100%) | (NE, NE) | (100%, 100%) |
| Best overall response | | | | |
| Confirmed complete response (CR) | 0 | 0 | 0 | 0 |
| Confirmed partial response (PR) | 0 | 1 (100.0%) | 0 | 1 (100.0%) |

TABLE 10-continued

Best Overall Response by FGFR Alterations (Mutually Exclusive)-Investigator Assessment; Treated Chemo Relapsed/Refractory Subjects

| | 8 mg QD | 6 mg QD | 10 mg 7 on/7 off | Total |
|---|---|---|---|---|
| Stable disease (SD) | 0 | 0 | 0 | 0 |
| Progressive disease (PD) | 0 | 0 | 0 | 0 |
| Inevaluable | 0 | 0 | 0 | 0 |
| Mutation and fusion: FGFR3-S249C/FGFR3-Y373C/FGFR2-CASP7/FGFR3-BAIAP2L1/FGFR3-TACC3 V1/FGFR3-TACC3 V3 | | | | |
| Total number of subjects | 0 | 0 | 1 | 1 |
| Objective response rate (CR + PR) | 0 | 0 | 0 | 0 |
| 95% CI | (NE, NE) | (NE, NE) | (NE, NE) | (NE, NE) |
| Disease control rate (CR + PR + SD) | 0 | 0 | 1 (100.0%) | 1 (100.0%) |
| 95% CI | (NE, NE) | (NE, NE) | (100%, 100%) | (100%, 100%) |
| Best overall response | | | | |
| Confirmed complete response (CR) | 0 | 0 | 0 | 0 |
| Confirmed partial response (PR) | 0 | 0 | 0 | 0 |
| Stable disease (SD) | 0 | 0 | 1 (100.0%) | 1 (100.0%) |
| Progressive disease (PD) | 0 | 0 | 0 | 0 |
| Inevaluable | 0 | 0 | 0 | 0 |

95% CI are 95% confidence interval calculated with normal approximation.

Specific FGFR alterations are mutually exclusive.

TABLE 11

Duration of Response by FGFR Alterations (Mutually Exclusive)-Investigator Assessment; Treated Chemo Relapsed/Refractory Subjects (Primary analysis cutoff date)

| | 8 mg QD | 6 mg QD | 10 mg 7 on/7 off | Total |
|---|---|---|---|---|
| FGFR mutations (excluding fusions) | | | | |
| Number of responders | 31 | 22 | 5 | 58 |
| Duration of response (months) | | | | |
| Median (95% CI) | 5.55 (4.21, 7.00) | 4.53 (4.01, 7.79) | 13.37 (4.17, 19.45) | 5.55 (4.21, 6.97) |
| Q1, Q3 | 4.21, 7.23 | 4.01, 9.10 | 11.86, 16.66 | 4.07, 9.66 |
| Range | (2.4, 14.3+) | (2.5, 17.5) | (4.2, 19.4) | (2.4, 19.4) |
| 6-month progression-free survival rate (95% CI) | 0.42 (0.24, 0.59) | 0.41 (0.21, 0.60) | 0.80 (0.20, 0.97) | 0.45 (0.32, 0.58) |
| 9-month progression-free survival rate (95% CI) | 0.19 (0.07, 0.37) | 0.27 (0.11, 0.46) | 0.80 (0.20, 0.97) | 0.29 (0.17, 0.42) |
| 12-month progression-free survival rate (95% CI) | 0.19 (0.07, 0.37) | 0.18 (0.06, 0.36) | 0.60 (0.13, 0.88) | 0.22 (0.12, 0.35) |
| FGFR fusions (excluding mutations) | | | | |
| Number of responders | 4 | 2 | 0 | 6 |
| Duration of response (months) | | | | |
| Median (95% CI) | NE (2.96, NE) | 9.20 (4.17, 14.23) | | 9.40 (2.96, 14.23) |
| Q1, Q3 | 3.76, NE | 4.17, 14.23 | | 4.17, 14.23 |
| Range | (3.0, 9.7+) | (4.2, 14.2) | | (3.0, 14.2) |
| 6-month progression-free survival rate (95% CI) | 0.50 (0.06, 0.84) | 0.50 (0.01, 0.91) | | 0.50 (0.11, 0.80) |
| 9-month progression-free survival rate (95% CI) | 0.50 (0.06, 0.84) | 0.50 (0.01, 0.91) | | 0.50 (0.11, 0.80) |
| 12-month progression-free survival rate (95% CI) | NE (NE, NE) | 0.50 (0.01, 0.91) | | 0.50 (0.11, 0.80) |
| FGFR mutations and fusions | | | | |
| Number of responders | 0 | 3 | 1 | 4 |
| Duration of response (months) | | | | |
| Median (95% CI) | | 11.27 (4.17, NE) | 4.34 (NE, NE) | 7.80 (4.17, NE) |
| Q1, Q3 | | 4.17, NE | 4.34, 4.34 | 4.25, NE |
| Range | | (4.2, 13.5+) | (4.3, 4.3) | (4.2, 13.5+) |
| 6-month progression-free survival rate (95% CI) | | 0.67 (0.05, 0.95) | 0 (NE, NE) | 0.50 (0.06, 0.84) |
| 9-month progression-free survival rate (95% CI) | | 0.67 (0.05, 0.95) | 0 (NE, NE) | 0.50 (0.06, 0.84) |
| 12-month progression-free survival rate (95% CI) | | 0.33 (0.01, 0.77) | 0 (NE, NE) | 0.25 (0.01, 0.67) |

Specific FGFR alterations are mutually exclusive.

Quartiles are estimated with Kaplan-Meier method.

+ indicates subjects censored.

TABLE 12

Progression-free Survival by FGFR Alterations (Mutually Exclusive)-Investigator Assessment; Treated Chemo Relapsed/Refractory Subjects (primary analysis cutoff date)

| | 8 mg QD | 6 mg QD | 10 mg 7 on/7 off | Total |
|---|---|---|---|---|
| FGFR mutations (excluding fusions) | | | | |
| Total number of subjects | 64 | 59 | 24 | 147 |
| Progression-free survival (months) | | | | |
| Median (95% CI) | 5.55 (4.83, 7.26) | 5.09 (2.83, 5.42) | 4.93 (2.73, 5.55) | 5.36 (4.21, 5.52) |
| Q1, Q3 | 2.83, 8.44 | 1.77, 5.55 | 2.69, 7.06 | 2.73, 8.25 |
| Range | (0.0+, 15.6+) | (0.5, 19.0) | (1.1, 20.8) | (0.0+, 20.8) |
| 6-month progression-free survival rate (95% CI) | 0.41 (0.29, 0.53) | 0.22 (0.12, 0.33) | 0.25 (0.10, 0.43) | 0.31 (0.24, 0.39) |
| 12-month progression-free survival rate (95% CI) | 0.15 (0.06, 0.27) | 0.07 (0.02, 0.16) | 0.17 (0.05, 0.34) | 0.12 (0.07, 0.19) |
| 18-month progression-free survival rate (95% CI) | NE (NE, NE) | 0.05 (0.01, 0.14) | 0.08 (0.01, 0.23) | 0.06 (0.03, 0.12) |
| FGFR fusions (excluding mutations) | | | | |
| Total number of subjects | 23 | 10 | 2 | 35 |
| Progression-free survival (months) | | | | |
| Median (95% CI) | 2.76 (1.51, 5.45) | 5.54 (0.46, 11.10) | 2.09 (1.41, 2.76) | 4.27 (2.56, 5.52) |
| Q1, Q3 | 1.35, 6.64 | 4.50, 11.10 | 1.41, 2.76 | 1.51, 7.00 |
| Range | (0.7, 14.0) | (0.5, 19.7) | (1.4, 2.8) | (0.5, 19.7) |
| 6-month progression-free survival rate (95% CI) | 0.25 (0.10, 0.44) | 0.40 (0.12, 0.67) | 0 (NE, NE) | 0.28 (0.15, 0.44) |
| 12-month progression-free survival rate (95% CI) | 0.15 (0.04, 0.33) | 0.20 (0.03, 0.47) | 0 (NE, NE) | 0.15 (0.05, 0.29) |
| 18-month progression-free survival rate (95% CI) | 0 (NE, NE) | 0.10 (0.01, 0.36) | 0 (NE, NE) | 0.05 (0.00, 0.19) |
| FGFR mutations and fusions | | | | |
| Total number of subjects | 0 | 4 | 3 | 7 |
| Progression-free survival (months) | | | | |
| Median (95% CI) | | 9.10 (0.39, NE) | 5.45 (1.45, 5.52) | 5.52 (0.39, 12.65) |
| Q1, Q3 | | 2.97, NE | 1.45, 5.52 | 1.45, 12.65 |
| Range | | (0.4, 15.1+) | (1.4, 5.5) | (0.4, 15.1+) |
| 6-month progression-free survival rate (95% CI) | | 0.50 (0.06, 0.84) | 0 (NE, NE) | 0.29 (0.04, 0.61) |
| 12-month progression-free survival rate (95% CI) | | 0.50 (0.06, 0.84) | 0 (NE, NE) | 0.29 (0.04, 0.61) |
| 18-month progression-free survival rate (95% CI) | | NE (NE, NE) | 0 (NE, NE) | NE (NE, NE) |

Quartiles are estimated with Kaplan-Meier method.
Specific FGFR alterations are mutually exclusive.
+ indicates subjects censored.

TABLE 13

Overall Survival by by FGFR Alterations (Mutually Exclusive); Treated Chemo Relapsed/Refractory Subjects (Primary analysis cutoff date)

| | 8 mg QD | 6 mg QD | 10 mg 7 on/7 off | Total |
|---|---|---|---|---|
| FGFR mutations (excluding fusions) | | | | |
| Total number of subjects | 64 | 59 | 24 | 147 |
| Overall survival (months) | | | | |
| Median (95% CI) | 12.02 (8.64, NE) | 8.31 (6.41, 9.63) | 7.39 (5.78, 10.71) | 9.10 (7.46, 11.86) |
| Q1, Q3 | 5.98, NE | 5.13, 14.82 | 5.55, 18.76 | 5.49, 18.76 |
| Range | (1.2+, 17.4+) | (0.5, 20.9+) | (1.7, 24.5+) | (0.5, 24.5+) |
| 6-month overall survival rate (95% CI) | 0.74 (0.61, 0.83) | 0.68 (0.54, 0.79) | 0.70 (0.47, 0.84) | 0.71 (0.63, 0.78) |
| 12-month overall survival rate (95% CI) | 0.54 (0.38, 0.68) | 0.30 (0.18, 0.43) | 0.31 (0.14, 0.50) | 0.39 (0.30, 0.48) |
| 18-month overall survival rate (95% CI) | NE (NE, NE) | 0.21 (0.11, 0.33) | 0.26 (0.11, 0.45) | 0.29 (0.20, 0.39) |
| 24-month overall survival rate (95% CI) | NE (NE, NE) | NE (NE, NE) | 0.22 (0.08, 0.40) | 0.24 (0.15, 0.35) |
| FGFR fusions (excluding mutations) | | | | |
| Total number of subjects | 23 | 10 | 2 | 35 |
| Overall survival (months) | | | | |
| Median (95% CI) | 10.32 (6.05, NE) | 9.33 (0.46, NE) | 10.37 (7.72, 13.01) | 9.33 (7.72, 18.96) |
| Q1, Q3 | 6.05, 14.03 | 7.92, 18.96 | 7.72, 13.01 | 6.97, 18.96 |
| Range | (0.7, 14.5+) | (0.5, 21.6+) | (7.7, 13.0) | (0.5, 21.6+) |
| 6-month overall survival rate (95% CI) | 0.77 (0.54, 0.90) | 0.80 (0.41, 0.95) | 1.00 (1.00, 1.00) | 0.80 (0.62, 0.90) |

TABLE 13-continued

Overall Survival by by FGFR Alterations (Mutually Exclusive); Treated Chemo Relapsed/Refractory Subjects (Primary analysis cutoff date)

| | 8 mg QD | 6 mg QD | 10 mg 7 on/7 off | Total |
|---|---|---|---|---|
| 12-month overall survival rate (95% CI) | 0.46 (0.24, 0.66) | 0.46 (0.14, 0.73) | 0.50 (0.01, 0.91) | 0.46 (0.28, 0.62) |
| 18-month overall survival rate (95% CI) | NE (NE, NE) | 0.46 (0.14, 0.73) | 0 (NE, NE) | 0.31 (0.12, 0.52) |
| 24-month overall survival rate (95% CI) | NE (NE, NE) | NE (NE, NE) | 0 (NE, NE) | NE (NE, NE) |
| FGFR mutations and fusions | | | | |
| Total number of subjects | 0 | 4 | 3 | 7 |
| Overall survival (months) | | | | |
| Median (95% CI) | | 12.65 (0.39, NE) | 6.21 (3.98, 9.10) | 9.10 (0.39, NE) |
| Q1, Q3 | | 6.52, NE | 3.98, 9.10 | 3.98, 12.65 |
| Range | | (0.4, 19.2+) | (4.0, 9.1) | (0.4, 19.2+) |
| 6-month overall survival rate (95% CI) | | 0.75 (0.13, 0.96) | 0.67 (0.05, 0.95) | 0.71 (0.26, 0.92) |
| 12-month overall survival rate (95% CI) | | 0.75 (0.13, 0.96) | 0 (NE, NE) | 0.43 (0.10, 0.73) |
| 18-month overall survival rate (95% CI) | | 0.38 (0.01, 0.81) | 0 (NE, NE) | 0.21 (0.01, 0.59) |
| 24-month overall survival rate (95% CI) | | NE (NE, NE) | 0 (NE, NE) | NE (NE, NE) |

Quartiles are estimated with Kaplan-Meier method.
Specific FGFR alterations are mutually exclusive.
+ indicates subjects censored.

Secondary End Points

Figure 4:
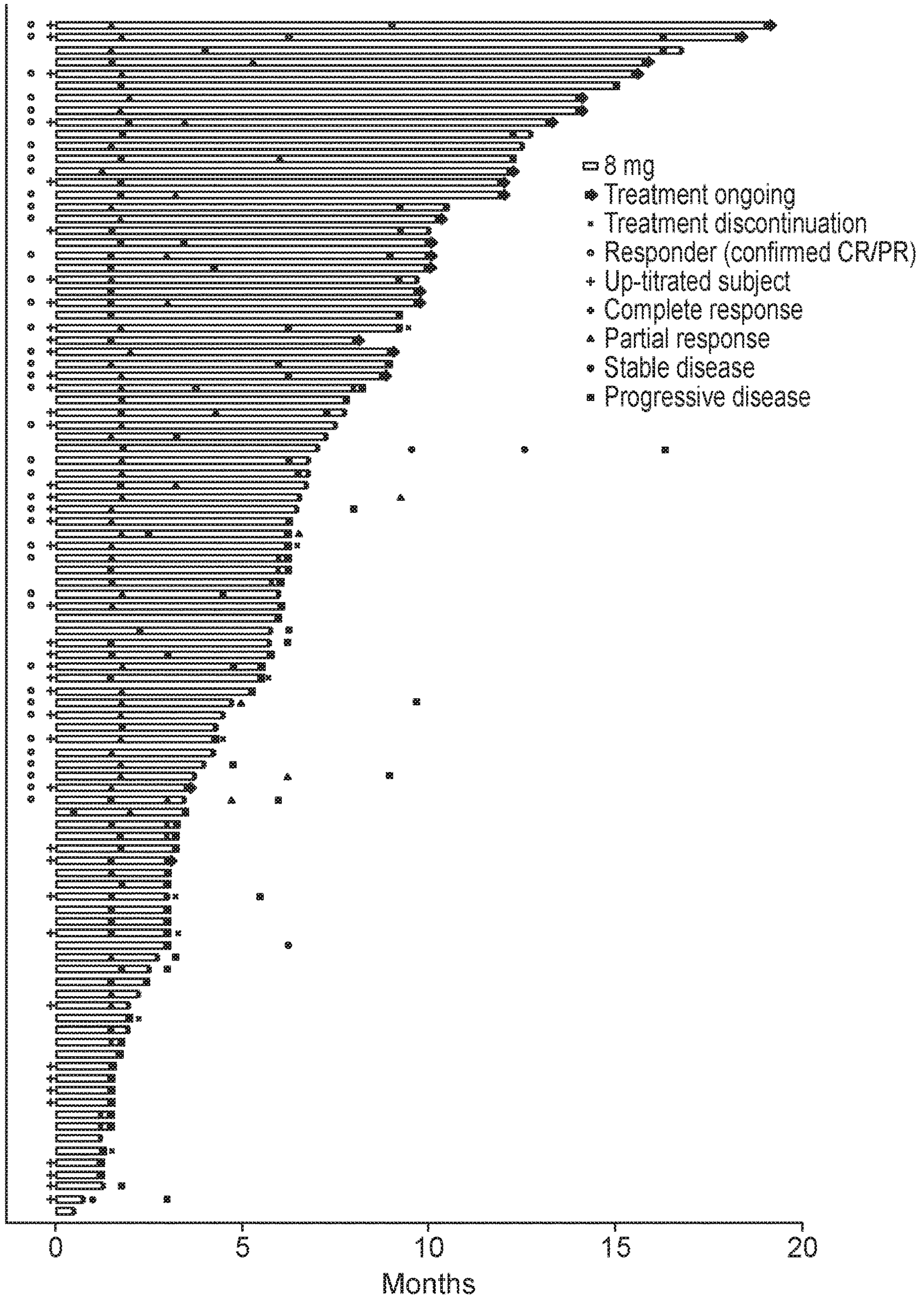
FIG. 4 is a swimmer plot of responses to treatment with erdafitinib among all patients treated with 8 mg per day continuous erdafitinib. Responses per investigator assessment FIG. 5, which comprises

Response duration among patients receiving regimen 3 is presented in Table 7; roughly 30% of responses were maintained for >12 months. Among 39 patients with stable disease, 13 (33%) had disease stabilization lasting >6 months (FIG. 4). Twenty-one percent of patients remained on treatment at the time of data cutoff.

Figure 5A:
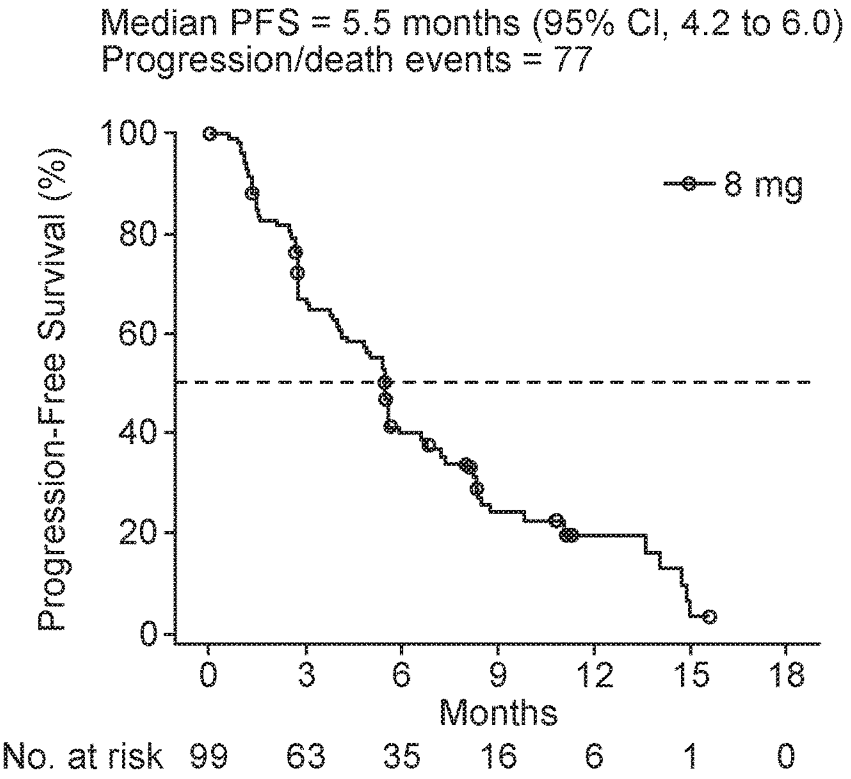
FIGS. 5A-5B, depicts progression-free survival and overall survival among patients treated with 8 mg per day continuous erdafitinib (Regimen 3). Kaplan-Meier curve of (FIG. 5A) progression-free survival and (FIG. 5B) overall survival after treatment with 8 mg continuous erdafitinib.
Figure 5B:
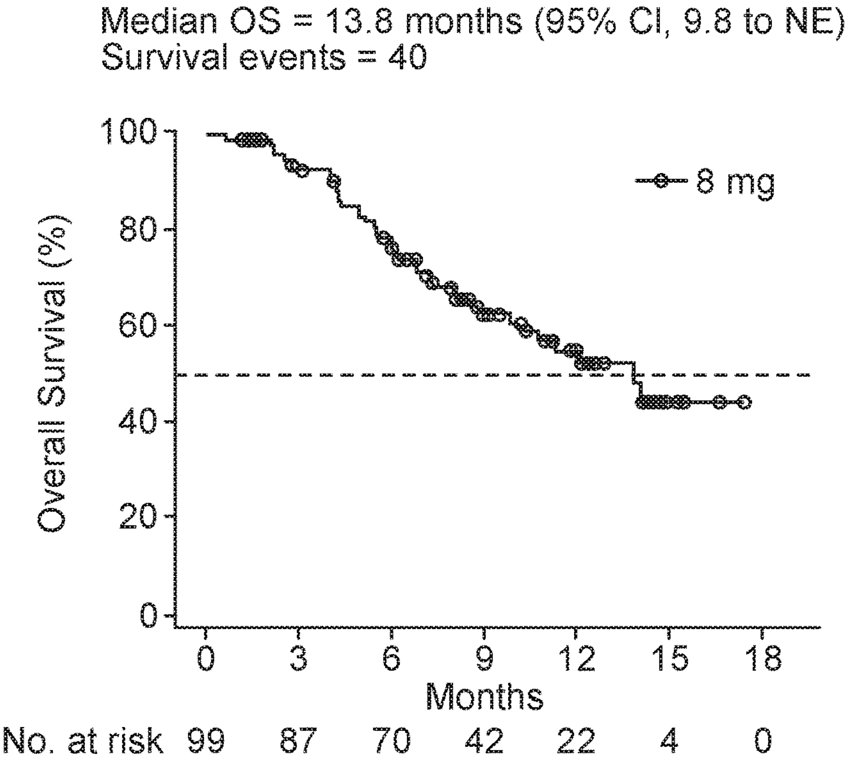

Median progression-free survival per investigator assessment at median follow-up of 11.2 months in patients receiving regimen 3 is presented in FIG. 5A. Progression-free survival rate (95% CI) at 12 months was 19% (11% to 29%). Median overall survival at median 11.0 months' follow-up for survival is presented in FIG. 5B. Survival rate at 12 months was 55% (43% to 66%).

Among 99 patients receiving regimen 3, 34 (34%) went on to subsequent therapy, 25 (25%) of whom received one subsequent line and nine (9%) of whom received two subsequent lines. Nineteen (19%) received chemotherapy, and 15 (15%) received immunotherapy as first subsequent therapy. No patient had objective response to first subsequent chemotherapy; one patient had partial response to first subsequent immunotherapy.

Figure 6A:
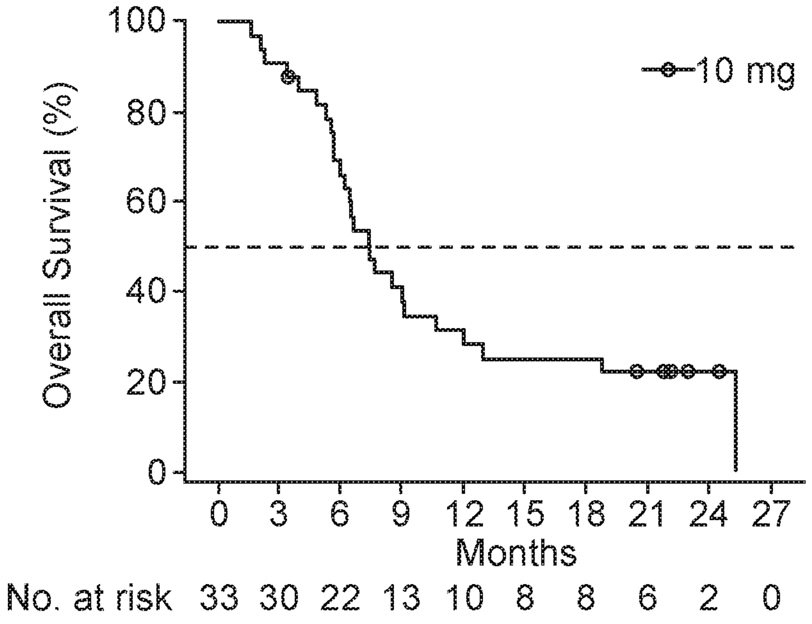
FIGS. 6A-6B, depicts overall survival among patients treated with 10 mg intermittent and 6 mg per day continuous erdafitinib. Kaplan-Meier curves of overall survival after treatment with (FIG. 6A) 10 mg intermittent erdafitinib (regimen 1) and (FIG. 6B) 6 mg per day continuous erdafitinib (regimen 2).
Figure 6B:
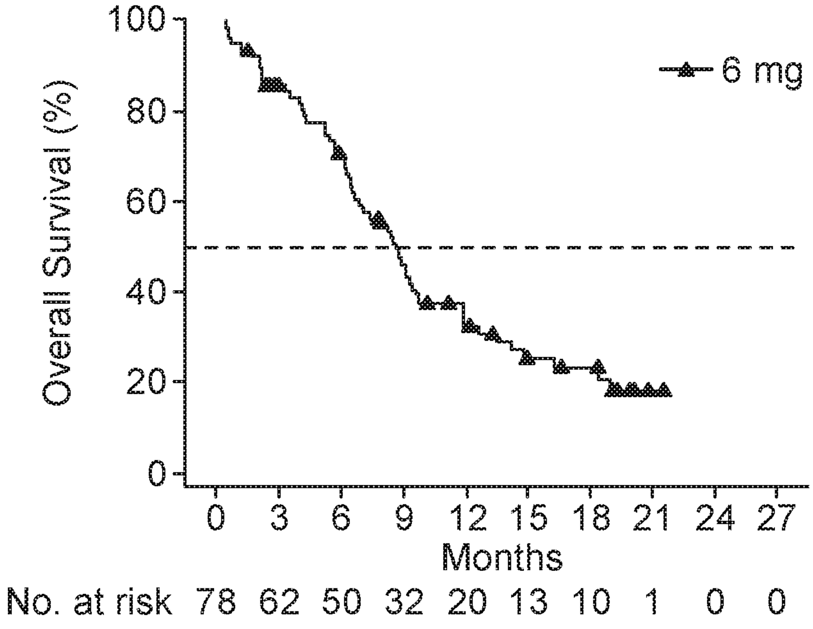

Response durations for patients treated with regimens 1 and 2 are also presented in Table 7. Progression-free survival and overall survival among patients receiving regimens 1 and 2 are presented in FIG. 6A-6B.

Median (95% CI) progression-free survival per investigator assessment was 4.8 (2.7 to 5.5) months and 5.3 (4.1 to 5.5) months among patients receiving regimens 1 and 2, respectively. Progression-free survival rates (95% CI) at 12 months in regimens 1 and 2 were 18% (7% to 33%) and 11% (5% to 19%), respectively. Median overall survival (95% CI) of patients receiving regimens 1 and 2 was 7.5 (6.0 to 10.7) months and 8.6 (6.5 to 9.7) months, respectively (FIG. 6A-6B), at a median follow-up for survival of 22.9 months in regimen 1 and 18.5 months in regimen 2. The overall survival rates (95% CI) at 12 months were 31% (16% to 48%) and 33% (22% to 44%) among patients in regimens 1 and 2, respectively.

Prophylactic Measures

Prophylactic measures were taken to minimize risk of common adverse events related to FGFR inhibition. To reduce risk of hyperphosphatemia, a low-phosphate diet was recommended for all patients (600 to 800 mg of dietary phosphate intake per day). To reduce the risk of skin effects, the application of alcohol-free emollient moisturizing cream and avoidance of unnecessary exposure to sunlight, soap, perfumed products, and hot baths was recommended. Patients were asked to keep their fingers and toes clean and nails trimmed to reduce risk of nail effects.

As central serious retinopathy, a retinal disorder that is reversible upon temporary drug interruption, has been reported with kinase inhibitors and FGFR inhibitors, patients were tested at baseline and routinely monitored for this ocular adverse event with in-office Amsler grid testing and ophthalmology examination including fundoscopy and, if available, optic coherence tomography. Additional ophthalmology examinations were performed if clinically indicated.

Safety

All patients in regimen 3 reported treatment-emergent adverse events (Table 19); 67% were grade 3 or 4. Serious treatment-emergent adverse events were reported in 39 patients (39%) (Table 15). Disease progression was the most common reason for treatment discontinuation in 62 patients (63%). Thirteen patients (13%) discontinued due to treatment-emergent-adverse events, including retinal pigment epithelium detachment, hand-foot syndrome, and dry mouth and skin/nail events (n=2 each). Fifty-five patients (56%) required dose reduction; the most common treatment-emergent adverse events leading to dose reduction were stomatitis in 16 patients (16%) and hyperphosphatemia in nine patients (9%). The safety profile allowed uptitration to 9 mg per day continuous erdafitinib in 41 patients in the 8 mg regimen who had not reached 5.5 mg per dl target serum phosphate by day 14. Among these 41 patients, 24 (59%) required ≥1 dose reduction. Similar percentages of patients in the 8 mg per day continuous group who were uptitrated to 9 mg per day reported grade ≥3 treatment-emergent adverse events compared with the overall trial population (68% and 66%, respectively). Common treatment-emergent and treatment-related adverse events were similar among all regimens (Table 16 and Table 17). One patient died as a result of an adverse event (myocardial infarction considered unrelated to treatment). Treatment-related adverse events of special interest or clinical importance and their management are presented in Table 18. Seventy-six percent of central serious retinopathy events resolved; all unresolved events were grade 1 or 2.

Treatment-Emergent, All-causality Adverse Events Reported in ≥ 10% of Patients in Any Group Treated With Erdafitinib

| | 10 mg Intermittent, Regimen 1 (n = 33) | | | | 6 mg Continuous, Regimen 2 (n = 78) | |
|---|---|---|---|---|---|---|
| Patients with adverse events- no. (%) | Any grade | Grade 1 | Grade 2 | Grade ≥ 3 | Any grade | Grade 1 |
| Hyperphosphatemia | 16 (48) | 15 (46) | 1 (3) | 0 | 52 (67) | 44 (56) |
| Stomatitis | 16 (48) | 9 (27) | 6 (18) | 1 (3) | 33 (42) | 13 (17) |
| Dry mouth | 16 (48) | 15 (46) | 1 (3) | 0 | 31 (40) | 23 (30) |
| Diarrhea | 14 (42) | 7 (21) | 6 (18) | 1 (3) | 39 (50) | 24 (31) |
| Decreased appetite | 11 (33) | 4 (12) | 6 (18) | 1 (3) | 29 (37) | 12 (15) |
| Dysgeusia | 10 (30) | 7 (21) | 3 (9) | 0 | 10 (13) | 6 (8) |
| Fatigue | 6 (18) | 4 (12) | 2 (6) | 0 | 20 (26) | 8 (10) |
| Dry skin | 9 (27) | 8 (24) | 1 (3) | 0 | 18 (23) | 10 (13) |
| Alopecia | 4 (12) | 2 (6) | 2 (6) | 0 | 10 (13) | 9 (12) |
| Constipation | 14 (42) | 8 (24) | 6 (18) | 0 | 20 (26) | 10 (13) |
| Hand-foot syndrome | 2 (6) | 0 | 2 (6) | 0 | 13 (17) | 4 (5) |
| Anemia | 8 (24) | 1 (3) | 1 (3) | 6 (18) | 13 (17) | 0 |
| Asthenia | 10 (30) | 5 (15) | 3 (9) | 2 (6) | 18 (23) | 5 (6) |
| Nausea | 5 (15) | 3 (9) | 2 (6) | 0 | 16 (21) | 11 (14) |
| Dry eye | 3 (9) | 2 (6) | 1 (3) | 0 | 6 (8) | 3 (4) |
| Abdominal pain | 5 (15) | 2 (6) | 2 (6) | 1 (3) | 14 (18) | 7 (9) |
| Onycholysis | 7 (21) | 3 (9) | 3 (9) | 1 (3) | 13 (17) | 2 (3) |
| Alanine aminotransferase increased | 1 (3) | 0 | 1 (3) | 0 | 9 (12) | 7 (9) |
| Paronychia | 2 (6) | 0 | 2 (6) | 0 | 12 (15) | 2 (3) |
| Vision blurred | 5 (15) | 4 (12) | 1 (3) | 0 | 5 (6) | 3 (4) |
| Nail dystrophy | 2 (6) | 2 (6) | 0 | 0 | 7 (9) | 6 (8) |
| Urinary tract infection | 4 (12) | 0 | 2 (6) | 2 (6) | 13 (17) | 0 |
| Weight decreased | 3 (9) | 1 (3) | 2 (6) | 0 | 8 (10) | 4 (5) |
| Peripheral edema | 5 (15) | 1 (3) | 4 (12) | 0 | 6 (8) | 2 (3) |
| Back pain | 5 (15) | 1 (3) | 1 (3) | 3 (9) | 11 (14) | 6 (8) |
| Pyrexia | 5 (15) | 5 (15) | 0 | 0 | 14 (18) | 8 (10) |
| Conjunctivitis | 4 (12) | 3 (9) | 1 (3) | 0 | 7 (9) | 4 (5) |
| Vomiting | 9 (27) | 7 (21) | 2 (6) | 0 | 11 (14) | 9 (12) |
| Hyponatremia | 2 (6) | 0 | 0 | 2 (6) | 7 (9) | 2 (3) |
| Pain in extremity | 5 (15) | 3 (9) | 1 (3) | 1 (3) | 9 (12) | 2 (3) |
| Dyspepsia | 3 (9) | 2 (6) | 1 (3) | 0 | 9 (12) | 6 (8) |
| Lacrimation increased | 6 (18) | 5 (15) | 1 (3) | 0 | 13 (17) | 10 (13) |
| Nail discoloration | 1 (3) | 0 | 1 (3) | 0 | 8 (10) | 6 (8) |
| Aspartate aminotransferase increased | 2 (6) | 2 (6) | 0 | 0 | 9 (12) | 7 (9) |
| Blood creatinine increased | 4 (12) | 3 (9) | 1 (3) | 0 | 6 (8) | 3 (4) |
| Hematuria | 3 (9) | 1 (3) | 2 (6) | 0 | 6 (8) | 5 (6) |
| Hypomagnesemia | 2 (6) | 2 (6) | 0 | 0 | 6 (8) | 6 (8) |
| Insomnia | 3 (9) | 0 | 3 (9) | 0 | 8 (10) | 4 (5) |
| Onychomadesis | 1 (3) | 1 (3) | 0 | 0 | 8 (10) | 2 (3) |
| Oropharyngeal pain | 0 | 0 | 0 | 0 | 8 (10) | 5 (6) |
| Retinal detachment | 2 (6) | 1 (3) | 1 (3) | 0 | 8 (10) | 5 (6) |
| Dyspnea | 8 (24) | 3 (9) | 2 (6) | 3 (9) | 6 (7) | 1 (1) |
| Arthralgia | 7 (21) | 3 (9) | 2 (6) | 2 (6) | 8 (10) | 5 (6) |

| | 6 mg Continuous, Regimen 2 (n = 78) | | 8 mg Continuous, Selected Regimen 3 (n = 99) | | | |
|---|---|---|---|---|---|---|
| Patients with adverse events- no. (%) | Grade 2 | Grade ≥ 3 | Any grade | Grade 1 | Grade 2 | Grade ≥ 3 |
| Hyperphosphatemia | 8 (10) | 0 | 76 (77) | 53 (54) | 21 (21) | 2 (2) |
| Stomatitis | 13 (17) | 7 (9) | 57 (58) | 21 (21) | 26 (26) | 10 (10) |
| Dry mouth | 6 (8) | 2 (3) | 45 (46) | 34 (34) | 11 (11) | 0 |
| Diarrhea | 15 (19) | 0 | 50 (51) | 31 (31) | 15 (15) | 4 (4) |
| Decreased appetite | 13 (17) | 4 (5) | 38 (38) | 18 (18) | 20 (20) | 0 |
| Dysgeusia | 4 (5) | 0 | 37 (37) | 23 (23) | 13 (13) | 1 (1) |
| Fatigue | 8 (10) | 4 (5) | 32 (32) | 12 (12) | 18 (18) | 2 (2) |
| Dry skin | 8 (10) | 0 | 32 (32) | 24 (24) | 8 (8) | 0 |
| Alopecia | 1 (1) | 0 | 29 (29) | 23 (23) | 6 (6) | 0 |
| Constipation | 10 (13) | 0 | 28 (28) | 19 (19) | 8 (8) | 1 (1) |
| Hand-foot syndrome | 9 (12) | 0 | 23 (23) | 6 (6) | 12 (12) | 5 (5) |
| Anemia | 8 (10) | 5 (6) | 20 (20) | 9 (9) | 7 (7) | 4 (4) |
| Asthenia | 4 (5) | 9 (12) | 20 (20) | 2 (2) | 11 (11) | 7 (7) |
| Nausea | 4 (5) | 1 (1) | 20 (20) | 13 (13) | 6 (6) | 1 (1) |
| Dry eye | 2 (3) | 1 (1) | 19 (19) | 14 (14) | 4 (4) | 1 (1) |
| Abdominal pain | 5 (6) | 2 (3) | 8 (8) | 5 (5) | 2 (2) | 1 (1) |
| Onycholysis | 6 (8) | 5 (6) | 18 (18) | 6 (6) | 10 (10) | 2 (2) |

-continued

Treatment-Emergent, All-causality Adverse Events Reported in ≥ 10% of Patients in Any Group Treated With Erdafitinib

| | | | | | | |
|---|---|---|---|---|---|---|
| Alanine aminotransferase increased | 2 (3) | 0 | 17 (17) | 13 (13) | 2 (2) | 2 (2) |
| Paronychia | 10 (13) | 0 | 17 (17) | 3 (3) | 11 (11) | 3 (3) |
| Vision blurred | 1 (1) | 1 (1) | 17 (17) | 10 (10) | 7 (7) | 0 |
| Nail dystrophy | 1 (1) | 0 | 16 (16) | 5 (5) | 5 (5) | 6 (6) |
| Urinary tract infection | 9 (12) | 4 (5) | 16 (16) | 0 | 11 (11) | 5 (5) |
| Weight decreased | 2 (3) | 2 (3) | 15 (15) | 7 (7) | 8 (8) | 0 |
| Peripheral edema | 3 (4) | 1 (1) | 9 (9) | 5 (5) | 3 (3) | 1 (1) |
| Back pain | 3 (4) | 2 (3) | 5 (5) | 4 (4) | 1 (1) | 0 |
| Pyrexia | 3 (4) | 3 (4) | 13 (13) | 8 (8) | 5 (5) | 0 |
| Conjunctivitis | 2 (3) | 1 (1) | 13 (13) | 6 (6) | 7 (7) | 0 |
| Vomiting | 2 (3) | 0 | 13 (13) | 10 (10) | 1 (1) | 2 (2) |
| Hyponatremia | 0 | 5 (6) | 12 (12) | 1 (1) | 0 | 11 (11) |
| Pain in extremity | 6 (8) | 1 (1) | 12 (12) | 10 (10) | 2 (2) | 0 |
| Dyspepsia | 3 (4) | 0 | 11 (11) | 10 (10) | 1 (1) | 0 |
| Lacrimation increased | 3 (4) | 0 | 11 (11) | 8 (8) | 3 (3) | 0 |
| Nail discoloration | 2 (3) | 0 | 11 (11) | 8 (8) | 3 (3) | 0 |
| Aspartate aminotransferase increased | 2 (3) | 0 | 10 (10) | 8 (8) | 2 (2) | 0 |
| Blood creatinine increased | 3 (4) | 0 | 10 (10) | 5 (5) | 5 (5) | 0 |
| Hematuria | 0 | 1 (1) | 10 (10) | 7 (7) | 1 (1) | 2 (2) |
| Hypomagnesemia | 0 | 0 | 10 (10) | 9 (9) | 1 (1) | 0 |
| Insomnia | 2 (3) | 2 (3) | 7 (7) | 4 (4) | 3 (3) | 0 |
| Onychomadesis | 6 (8) | 0 | 7 (7) | 2 (2) | 5 (5) | 0 |
| Oropharyngeal pain | 3 (4) | 0 | 10 (10) | 8 (8) | 1 (1) | 1 (1) |
| Retinal detachment | 3 (4) | 0 | 5 (5) | 3 (3) | 2 (2) | 0 |
| Dyspnea | 3 (4) | 2 (3) | 8 (8) | 4 (4) | 2 (2) | 2 (2) |
| Arthralgia | 2 (3) | 1 (1) | 8 (8) | 5 (5) | 3 (3) | 0 |

TABLE 15

Serious Treatment-Emergent Adverse Events Reported in ≥2% of Patients

| Patients With Serious Treatment-Emergent Adverse Events-no. (%) | 10 mg Intermittent, Regimen 1 (n = 33) | 6 mg Continuous, Regimen 2 (n = 78) | 8 mg Continuous, Selected Regimen 3 (n = 99) |
|---|---|---|---|
| Total number of patients with serious treatment-emergent adverse events | 14 (42) | 39 (50) | 39 (39) |
| Infections and infestations | 2 (6) | 13 (17) | 9 (9) |
| Urinary tract infection | 0 | 4 (5) | 3 (3) |
| Urosepsis | 0 | 3 (4) | 2 (2) |
| Gastrointestinal disorders | 2 (6) | 8 (10) | 8 (8) |
| General disorders/ administration site conditions | 1 (3) | 7 (9) | 8 (8) |
| General physical health deterioration | 1 (3) | 2 (3) | 3 (3) |
| Renal and urinary disorders | 1 (3) | 5 (6) | 10 (10) |
| Eye disorders | 1 (3) | 3 (4) | 9 (9) |
| Respiratory, thoracic, mediastinal disorders | 4 (12) | 3 (4) | 3 (3) |
| Dyspnea | 2 (6) | 1 (1) | 2 (2) |
| Metabolism and nutrition disorders | 1 (3) | 3 (4) | 2 (2) |
| Musculoskeletal and connective tissue disorders | 2 (6) | 4 (5) | 0 |
| Nervous system disorders | 0 | 5 (6) | 1 (1) |

TABLE 16

Treatment-Related Adverse Events Reported in ≥10% of Patients Treated with 8 mg per day Continuous Erdafitinib

| | 8 mg Continuous Erdafitinib (n = 99) | | | |
|---|---|---|---|---|
| Patients with Adverse Events-no. (%) | Any Grade | Grade 1 | Grade 2 | Grade 3 |
| Hyperphosphatemia | 72 (73) | 49 (50) | 21 (21) | 2 (2) |
| Stomatitis | 54 (55) | 19 (19) | 26 (26) | 9 (9) |
| Dry mouth | 43 (43) | 32 (32) | 11 (11) | 0 |
| Diarrhea | 37 (37) | 21 (21) | 12 (12) | 4 (4) |
| Dysgeusia | 35 (35) | 22 (22) | 12 (12) | 1 (1) |
| Dry skin | 32 (32) | 24 (24) | 8 (8) | 0 |
| Alopecia | 27 (27) | 21 (21) | 6 (6) | 0 |
| Decreased appetite | 25 (25) | 11 (11) | 14 (14) | 0 |
| Hand-foot syndrome | 22 (22) | 5 (5) | 12 (12) | 5 (5) |
| Fatigue | 21 (21) | 8 (8) | 11 (11) | 2 (2) |
| Dry eye | 19 (19) | 14 (14) | 4 (4) | 1 (1) |
| Nail dystrophy | 16 (16) | 5 (5) | 5 (5) | 6 (6) |
| Onycholysis | 16 (16) | 4 (4) | 10 (10) | 2 (2) |
| Vision blurred | 16 (16) | 10 (10) | 6 (6) | 0 |
| Paronychia | 14 (14) | 1 (1) | 10 (10) | 3 (3) |
| Asthenia | 13 (13) | 2 (2) | 9 (9) | 2 (2) |
| Alanine aminotransferase increased | 12 (12) | 9 (9) | 2 (2) | 1 (1) |
| Lacrimation increased | 11 (11) | 8 (8) | 3 (3) | 0 |
| Nail discoloration | 11 (11) | 8 (8) | 3 (3) | 0 |
| Weight decreased | 10 (10) | 5 (5) | 5 (5) | 0 |

TABLE 17

Treatment-Related Adverse Events Reported in ≥ 10% of Patients Treated With 10 mg Intermittent and 6 mg per Day Continuous Erdafitinib

| | 10 mg Intermittent, Regimen 1 (n = 33) | | | | 6 mg Continuous, Regimen 2 (n = 78) | | | |
|---|---|---|---|---|---|---|---|---|
| Patients with adverse events- no. (%) | Any grade | Grade 1 | Grade 2 | Grade ≥3 | Any grade | Grade 1 | Grade 2 | Grade ≥3 |
| Hyperphosphatemia | 15 (46) | 14 (42) | 1 (3) | 0 | 49 (63) | 41 (53) | 8 (10) | 0 |
| Stomatitis | 16 (49) | 9 (27) | 6 (18) | 1 (3) | 33 (42) | 13 (17) | 13 (17) | 7 (9) |
| Dry mouth | 14 (42) | 13 (39) | 1 (3) | 0 | 31 (40) | 23 (30) | 6 (8) | 2 (3) |
| Diarrhea | 13 (39) | 7 (21) | 5 (15) | 1 (3) | 29 (37) | 16 (21) | 13 (17) | 0 |
| Dysgeusia | 10 (30) | 7 (21) | 3 (9) | 0 | 10 (13) | 6 (8) | 4 (5) | 0 |
| Dry skin | 8 (24) | 7 (21) | 1 (3) | 0 | 16 (21) | 8 (10) | 8 (10) | 0 |
| Decreased appetite | 6 (18) | 2 (6) | 4 (12) | 0 | 18 (23) | 7 (9) | 9 (12) | 2 (3) |
| Onycholysis | 6 (18) | 2 (6) | 3 (9) | 1 (3) | 13 (17) | 2 (3) | 6 (8) | 5 (6) |
| Hand-foot syndrome | 2 (6) | 0 | 2 (6) | 0 | 12 (15) | 4 (5) | 8 (10) | 0 |
| Fatigue | 4 (12) | 2 (6) | 2 (6) | 0 | 12 (15) | 5 (6) | 6 (8) | 1 (1) |
| Lacrimation increased | 4 (12) | 4 (12) | 0 | 0 | 12 (15) | 9 (12) | 3 (4) | 0 |
| Nausea | 5 (15) | 3 (9) | 2 (6) | 0 | 6 (8) | 4 (5) | 2 (3) | 0 |
| Vision blurred | 5 (15) | 4 (12) | 1 (3) | 0 | 5 (6) | 3 (4) | 1 (1) | 1 (1) |
| Asthenia | 6 (18) | 2 (6) | 2 (6) | 2 (6) | 11 (14) | 3 (4) | 4 (5) | 4 (5) |
| Paronychia | 2 (6) | 0 | 2 (6) | 0 | 11 (14) | 1 (1) | 10 (13) | 0 |
| Conjunctivitis | 4 (12) | 3 (9) | 1 (3) | 0 | 2 (3) | 2 (3) | 0 | 0 |
| Alopecia | 3 (9) | 1 (3) | 2 (6) | 0 | 8 (10) | 8 (10) | 0 | 0 |
| Nail discoloration | 1 (3) | 0 | 1 (3) | 0 | 8 (10) | 6 (8) | 2 (3) | 0 |
| Onychomadesis | 1 (3) | 1 (3) | 0 | 0 | 8 (10) | 2 (3) | 6 (8) | 0 |
| Retinal detachment | 2 (6) | 1 (3) | 1 (3) | 0 | 8 (10) | 5 (6) | 3 (4) | 0 |

TABLE 18

Treatment-related Adverse Events of Special Interest or Clinical Importance Among Patients Treated With 8 mg per day Continuous Erdafitinib (Regimen 3).

| | 8 mg Continuous Erdafitinib (n = 99) | |
|---|---|---|
| Patients with adverse events-no. (%) | Any grade | Grade ≥3 |
| Hyperphosphatemia | 72 (73) | 2 (2) |
| Skin events | 48 (49) | 6 (6) |
| Dry skin | 32 (32) | 0 (0) |
| Hand-foot syndrome | 22 (22) | 5 (5) |
| Nail events | 51 (52) | 14 (14) |
| Onycholysis | 16 (16) | 2 (2) |
| Paronychia | 14 (14) | 3 (3) |
| Nail dystrophy | 16 (16) | 6 (6) |
| Central serous retinopathy* | 21 (21) | 3 (3) |
| Ocular events other than central serous retinopathy† | 51 (52) | 5 (5) |
| Arrhythmia-related events | 0 | 0 |

*Central serous retinopathy was an adverse event of special interest grouped term including the following individual preferred terms: retinal detachment, vitreous detachment, retinal edema, retinopathy, chorioretinopathy, detachment of retinal pigment epithelium, and detachment of macular retinal pigment epithelium.

†Most common ocular events other than central serous retinopathy included dry eye (19%), blurry vision (16%), increased lacrimation (11%), and conjunctivitis (9%).

TABLE 19

Treatment-Emergent, All-causality Adverse Events Reported in >15% of Patients or Grade ≥3 in More Than 1 Patient Treated With 8 mg Continuous Erdafitinib (Regimen 3).

| | 8 mg Continuous, Selected Regimen 3 (n = 99) | | | |
|---|---|---|---|---|
| Patients with adverse events-no. (%) | Any grade | Grade 1 | Grade 2 | Grade ≥3 |
| Hyperphosphatemia | 76 (77) | 53 (54) | 21 (21) | 2 (2) |
| Stomatitis | 57 (58) | 21 (21) | 26 (26) | 10 (10) |
| Dry mouth | 45 (46) | 34 (34) | 11 (11) | 0 |
| Diarrhea | 50 (51) | 31 (31) | 15 (15) | 4 (4) |
| Decreased appetite | 38 (38) | 18 (18) | 20 (20) | 0 |
| Dysgeusia | 37 (37) | 23 (23) | 13 (13) | 1 (1) |
| Fatigue | 32 (32) | 12 (12) | 18 (18) | 2 (2) |
| Dry skin | 32 (32) | 24 (24) | 8 (8) | 0 |
| Alopecia | 29 (29) | 23 (23) | 6 (6) | 0 |
| Constipation | 28 (28) | 19 (19) | 8 (8) | 1 (1) |
| Hand-foot syndrome | 23 (23) | 6 (6) | 12 (12) | 5 (5) |
| Anemia | 20 (20) | 9 (9) | 7 (7) | 4 (4) |
| Asthenia | 20 (20) | 2 (2) | 11 (11) | 7 (7) |
| Nausea | 20 (20) | 13 (13) | 6 (6) | 1 (1) |
| Dry eye | 19 (19) | 14 (14) | 4 (4) | 1 (1) |
| Abdominal pain | 8 (8) | 5 (5) | 2 (2) | 1 (1) |
| Onycholysis | 18 (18) | 6 (6) | 10 (10) | 2 (2) |
| Alanine aminotransferase increased | 17 (17) | 13 (13) | 2 (2) | 2 (2) |
| Paronychia | 17 (17) | 3 (3) | 11 (11) | 3 (3) |
| Vision blurred | 17 (17) | 10 (10) | 7 (7) | 0 |
| Nail dystrophy | 16 (16) | 5 (5) | 5 (5) | 6 (6) |
| Urinary tract infection | 16 (16) | 0 | 11 (11) | 5 (5) |

Treatment-related adverse events that were considered of special interest/clinical importance were hyperphosphatemia, skin effects, nail effects, and eye disorders, including central serous retinopathy (CSR) and other non-CSR ocular events (Table 18). Treatment-related hyperphosphatemia and effects on the skin and on the nails were reported in 73%, 49%, and 52%, respectively, of patients treated with 8 mg per day continuous erdafitinib. Most events were mild to moderate. In this group, the most common treatment-related effects on the skin were dry skin (32%) and hand-foot syndrome (22%), and the most common treatment-related nail effects were nail dystrophy and onycholysis in 16% of patients each. Overall, 63% of patients treated with 8 mg per day continuous erdafitinib and 54% of patients overall experienced some type of eye disorder, regardless of whether it was deemed related to treatment. Among patients with eye disorders (n=62), most (n=52, 84%) experienced grade 1 or 2 events. Twenty-one patients (21%) who received 8 mg per day continuous erdafitinib had treatment-related CSR, a preferred term that included chorioretinopathy, retinal detachment, and detachment of retinal pigment epithelium; only three of these patients (3%) had grade ≥3 events. Most patients with CSR events were able to continue treatment after management through dose interruption or reduction. CSR led to discontinuation in three patients; no patient had retinal vein or artery occlusion.

Management of Adverse Events

Hyperphosphatemia, the most common treatment-related adverse event (Table 16, 14, 16), was managed by dose interruption (23%), dose reduction (9%), and treatment with phosphate binders when medically warranted. Phosphate elevation typically peaked 6 weeks after erdafitinib initiation and normalized by cycle 5. One patient discontinued treatment due to grade 1 hyperphosphatemia. Dry skin was managed with additional topical ointments such as ammonium lactate, salicylic acid, or zinc oxide creams. Nail effects were managed with topical nail strengthener, and antibiotics or silver nitrate were applied in severe cases.

Discussion

This study met its primary objective, with a 40% confirmed ORR after treatment with 8 mg per day continuous erdafitinib, demonstrating antitumor activity in patients with locally advanced and unresectable/metastatic urothelial carcinoma who have certain FGFR genetic alterations compared with currently available treatment options. Responses to erdafitinib were rapid and independent of the number of prior lines and types of therapy, presence of visceral metastases, or tumor location.

Importantly, median progression-free and overall survival were 5.5 months (FIG. 5A) and 13.8 months (FIG. 5B), respectively, including patients with visceral metastases and poor kidney function who had progressed on or after multiple lines of therapy. As allowed by protocol, 13 patients continued treatment beyond progression, which was either limited progression in a target lesion or appearance of a small new lesion while the patient was assessed to have ongoing clinical benefit. The safety profile allowed 8 mg continuous daily dosing, with uptitration to 9 mg daily dosing guided by serum phosphate levels. Uptitration did not increase adverse event severity, as percentages of grade ≥3 events were similar across both groups. Hyperphosphatemia, a known class effect of FGFR inhibitors, was reported in 77% (regimen 3) and was typically manageable and reversible. Ocular events such as central serous retinopathy are known class effects of inhibitors of the mitogen-activated protein kinase pathway. Although ocular adverse events were common with erdafitinib treatment, these were mostly mild to moderate and resolved with dose interruption or reduction.

Patients with FGFR mutations or fusions may be less likely to respond to immunotherapy. In our study, only 1 of 22 (5%) patients had responded to prior immunotherapy, and 59% of those patients responded to erdafitinib after failure of immunotherapy. This observation was also noted in a study of rogaratinib in which nine of 10 patients (90%) had disease progression with prior immunotherapy, and 30% responded to rogaratinib These results indicate that the pan-FGFR inhibitor erdafitinib had measurable benefit in patients with advance urothelial carcinoma with FGFR alterations.

Example 2: Pharmacodynamics and Pharmacokinetics

Pharmacodynamics

Cardiac Electrophysiology

Based on evaluation of QTc interval in an open-label, dose escalation and dose expansion study in 187 patients with cancer, erdafitinib had no large effect (i.e., >20 ms) on the QTc interval.

Serum Phosphate

Erdafitinib increased serum phosphate level as a consequence of FGFR inhibition. Erdafitinib should be increased to the maximum recommended dose to achieve target serum phosphate levels of 5.5-7.0 mg/dL in early cycles with continuous daily dosing In erdafitinib clinical trials, the use of drugs which can increase serum phosphate levels, such as potassium phosphate supplements, vitamin D supplements, antacids, phosphate-containing enemas or laxatives, and medications known to have phosphate as an excipient were prohibited unless no alternatives exist. To manage phosphate elevation, phosphate binders were permitted. Avoid concomitant use with agents that can alter serum phosphate levels before the initial dose increase period based on serum phosphate levels.

Pharmacokinetics

Following administration of 8 mg once daily, the mean (coefficient of variation [CV %]) erdafitinib steady-state maximum observed plasma concentration (Cmax), area under the curve (AUCtau), and minimum observed plasma concentration (Cmin) were 1399 ng/mL (51%), 29268 ng h/mL (60%), and 936 ng/mL (65%), respectively.

Following single and repeat once daily dosing, erdafitinib exposure (maximum observed plasma concentration [Cmax] and area under the plasma concentration time curve [AUC]) increased proportionally across the dose range of 0.5 to 12 mg (0.06 to 1.3 times the maximum approved recommended dose). Steady state was achieved after 2 weeks with once daily dosing and the mean accumulation ratio was 4-fold.

Absorption

Median time to achieve peak plasma concentration (tmax) was 2.5 hours (range: 2 to 6 hours).

Effect of Food

No clinically meaningful differences with erdafitinib pharmacokinetics were observed following administration of a high-fat and high-calorie meal (800 calories to 1,000 calories with approximately 50% of total caloric content of the meal from fat) in healthy subjects.

Distribution

The mean apparent volume of distribution of erdafitinib was 29 L in patients. Erdafitinib protein binding was 99.8% in patients, primarily to alpha-1-acid glycoprotein.

Elimination

The mean total apparent clearance (CL/F) of erdafitinib was 0.362 L/h in patients.

The mean effective half-life of erdafitinib was 59 hours in patients.

Metabolism

Erdafitinib is primarily metabolized by CYP2C9 and CYP3A4. The contribution of CYP2C9 and CYP3A4 in the total clearance of erdafitinib is estimated to be 39% and 20% respectively. Unchanged erdafitinib was the major drug-related moiety in plasma, there were no circulating metabolites.

Excretion

Following a single oral dose of radiolabeled erdafitinib, approximately 69% of the dose was recovered in feces (19% as unchanged) and 19% in urine (13% as unchanged).

Specific Populations

No clinically meaningful trends in the pharmacokinetics of erdafitinib were observed based on age (21-88 years), sex, race, body weight (36-132 kg), mild (eGFR [estimated glomerular filtration rate, using modification of diet in renal disease equation] 60 to 89 mL/min/1.73 $m^2$) or moderate (eGFR 30-59 mL/min/1.73 $m^2$) renal impairment or mild hepatic impairment (total bilirubin≤ULN and AST≥ULN, or total bilirubin >1.0–1.5×ULN and any AST).

The pharmacokinetics of erdafitinib in patients with severe renal impairment, renal impairment requiring dialysis, moderate or severe hepatic impairment is unknown.

The examples and embodiments described herein are for illustrative purposes only and various modifications or changes suggested to persons skilled in the art are to be included within the spirit and purview of this application and scope of the appended claims.

What is claimed:

1. A method of treating urothelial carcinoma harboring at least two FGFR3 mutations comprising FGFR3 G370C and FGFR3 S249C: FGFR3 R248C and FGFR3 Y373C: or FGFR3 S249C and FGFR3 Y373C, in a patient, the method comprising administering a FGFR inhibitor to the patient.

2. The method of claim 1 further comprising evaluating a biological sample from the patient for the presence of the at least two FGFR3 mutations prior to administering the FGFR inhibitor.

3. The method of claim 1, wherein the urothelial carcinoma is locally advanced or metastatic.

4. The method of claim 2, wherein the biological sample is blood, lymph fluid, bone marrow, a solid tumor sample, or any combination thereof.

5. The method of claim 1, wherein the FGFR inhibitor is erdafitinib.

6. The method of claim 5, wherein erdafitinib is administered daily.

7. The method of claim 5, wherein erdafitinib is administered orally.

8. The method of claim 5, comprising administering erdafitinib orally at a dose of about 8 mg once daily.

9. The method of claim 8, wherein the dose of erdafitinib is increased from 8 mg once daily to 9 mg once daily at 14 to 21 days after initiating treatment if:

(a) the patient exhibits a serum phosphate (PO4) level that is less than 5.5 mg/dL at 14-21 days after initiating treatment; and (b) administration of erdafitinib at 8 mg once daily resulted in no ocular disorder or administration of erdafitinib at 8 mg once daily resulted in no Grade 2 or greater adverse reaction.

10. The method of claim 5, wherein erdafitinib is administered in the form of a tablet.

11. The method of claim 1, wherein the FGFR inhibitor is erdafitinib or a pharmaceutically acceptable salt thereof.

12. The method of claim 1, wherein the at least two FGFR3 mutations comprise FGFR3 G370C and FGFR3 S249C.

13. The method of claim 1, wherein the at least two FGFR3 mutations comprise FGFR3 R248C and FGFR3 Y373C.

14. The method of claim 1, wherein the at least two FGFR3 mutations comprise FGFR3 S249C and FGFR3 Y373C.

15. The method of claim 8, wherein the at least two FGFR3 mutations comprise FGFR3 G370C and FGFR3 S249C.

16. The method of claim 8, wherein the at least two FGFR3 mutations comprise FGFR3 R248C and FGFR3 Y373C.

17. The method of claim 8, wherein the at least two FGFR3 mutations comprise FGFR3 S249C and FGFR3 Y373C.

18. The method of claim 9, wherein the at least two FGFR3 mutations comprise FGFR3 G370C and FGFR3 S249C.

19. The method of claim 9, wherein the at least two FGFR3 mutations comprise FGFR3 R248C and FGFR3 Y373C.

20. The method of claim 9, wherein the at least two FGFR3 mutations comprise FGFR3 S249C and FGFR3 Y373C.

21. The method of claim 3, wherein the FGFR inhibitor is erdafitinib and the method comprises administering erdafitinib orally at a dose of about 8 mg once daily.

22. The method of claim 21, wherein the dose of erdafitinib is increased from 8 mg once daily to 9 mg once daily at 14 to 21 days after initiating treatment if:

(a) the patient exhibits a serum phosphate (PO4) level that is less than 5.5 mg/dL at 14-21 days after initiating treatment; and (b) administration of erdafitinib at 8 mg once daily resulted in no ocular disorder or administration of erdafitinib at 8 mg once daily resulted in no Grade 2 or greater adverse reaction.

23. The method of claim 21, wherein the at least two FGFR3 mutations comprise FGFR3 G370C and FGFR3 S249C.

24. The method of claim 21, wherein the at least two FGFR3 mutations comprise FGFR3 R248C and FGFR3 Y373C.

25. The method of claim 21, wherein the at least two FGFR3 mutations comprise FGFR3 S249C and FGFR3 Y373C.

26. The method of claim 22, wherein the at least two FGFR3 mutations comprise FGFR3 G370C and FGFR3 S249C.

27. The method of claim 22, wherein the at least two FGFR3 mutations comprise FGFR3 R248C and FGFR3 Y373C.

28. The method of claim 22, wherein the at least two FGFR3 mutations comprise FGFR3 S249C and FGFR3 Y373C.

* * * * *